（12） United States Patent
Marmur et al.

(10) Patent No.: US 10,603,197 B2
(45) Date of Patent: Mar. 31, 2020

(54) STENT SYSTEM WITH RADIAL-EXPANSION LOCKING

(71) Applicant: ENDOSPAN LTD., Herzilyia Pituach (IL)

(72) Inventors: Yaniv Marmur, Yokneam Moshava (IL); Or Zigelboim, Giv'atayim (IL); Nir Shalom Nae, Ra'anana (IL)

(73) Assignee: ENDOSPAN LTD., Herzliya Pituach (IL)

( * ) Notice: Subject to any disclaimer, the term of this patent is extended or adjusted under 35 U.S.C. 154(b) by 752 days.

(21) Appl. No.: 15/037,804

(22) PCT Filed: Nov. 6, 2014

(86) PCT No.: PCT/IL2014/050973
§ 371 (c)(1),
(2) Date: May 19, 2016

(87) PCT Pub. No.: WO2015/075708
PCT Pub. Date: May 28, 2015

(65) Prior Publication Data
US 2016/0302950 A1 Oct. 20, 2016

Related U.S. Application Data

(60) Provisional application No. 61/926,533, filed on Jan. 13, 2014, provisional application No. 61/906,014, filed on Nov. 19, 2013.

(51) Int. Cl.
*A61F 2/966* (2013.01)
*A61F 2/07* (2013.01)
(Continued)

(52) U.S. Cl.
CPC ................ *A61F 2/966* (2013.01); *A61F 2/07* (2013.01); *A61F 2002/061* (2013.01);
(Continued)

(58) Field of Classification Search
CPC ....... A61F 2/07; A61F 2/966; A61F 2002/061
See application file for complete search history.

(56) References Cited

U.S. PATENT DOCUMENTS 4,180,613 A 12/1979 Vassiliou
4,355,426 A 10/1982 MacGregor
(Continued)

FOREIGN PATENT DOCUMENTS

CA 2 497 704 3/2004
CN 1194577 9/1998
(Continued)

OTHER PUBLICATIONS

An Office Action dated Jul. 17, 2017, which issued during the prosecution of U.S. Appl. No. 14/759,736.
"E-vita® open plus" product brochure (JOTEC GmbH, Hechingen, Germany), 2010.
Fonseca A et al., "Intravascular ultrasound assessment of the novel AngioSculpt scoring balloon catheter for the treatment of complex coronary lesions," J Invasive Cardiol 20(1):21-7 (Jan. 2008).
(Continued)

*Primary Examiner* — Vy Q Bui
(74) *Attorney, Agent, or Firm* — Sughrue Mion, PLLC

(57) ABSTRACT

A deployment system (10, 410) includes an inner shaft (36, 436), removably disposed in a self-expanding stent-graft (40), and shaped so as to define (a) at least one conduit therealong (50, 450), which is (i) not coaxial with the inner shaft (36, 436), and (ii) shaped so as to define at least first (52, 452) and second enclosed longitudinal segments (54, 454), and (b) a restraining longitudinal portion (56, 456) that is longitudinally disposed between the first (52, 452) and second enclosed longitudinal segments (54, 454). The deployment system (10, 410) is configured such that (a) when a restraining wire (60, 460) thereof is removably disposed in the first (52, 452) and second enclosed longitu-
(Continued)

dinal segments (54, 454), a portion (62, 463) of the restraining wire (60, 460) disposed alongside the restraining longitudinal portion (56, 456) prevents full radial expansion of a longitudinal portion (70, 470) of the stent-graft (40) by physically engaging the stent-graft longitudinal portion (70, 470), and (b) when the restraining wire (60, 460) has been withdrawn from at least the first enclosed longitudinal segment (52, 452), the restraining wire (60, 460) does not prevent the full radial expansion of the stent-graft longitudinal portion (70, 470).

11 Claims, 34 Drawing Sheets

(51) Int. Cl.
A61F 2/06 (2013.01)
A61F 2/95 (2013.01)

(52) U.S. Cl.
CPC . A61F 2002/065 (2013.01); A61F 2002/9517 (2013.01); A61F 2002/9665 (2013.01); A61F 2250/006 (2013.01)

(56) References Cited

U.S. PATENT DOCUMENTS

| | | |
|---|---|---|
| 4,505,767 A | 3/1985 | Quin |
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,816,339 A | 3/1989 | Tu et al. |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,129,910 A | 7/1992 | Phan et al. |
| 5,133,732 A | 7/1992 | Wiktor |
| 5,192,256 A | 3/1993 | Ryan |
| 5,192,286 A | 3/1993 | Phan et al. |
| 5,234,448 A | 8/1993 | Wholey et al. |
| 5,383,926 A | 1/1995 | Lock et al. |
| 5,425,739 A | 6/1995 | Jessen |
| 5,425,765 A | 6/1995 | Tiefenbrun et al. |
| 5,439,446 A | 8/1995 | Barry |
| 5,456,694 A | 10/1995 | Marin et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,575,818 A | 11/1996 | Pinchuk |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,693,084 A | 12/1997 | Chuter |
| 5,728,134 A | 3/1998 | Barak |
| 5,749,825 A | 5/1998 | Fischell et al. |
| 5,749,879 A | 5/1998 | Middleman et al. |
| 5,755,770 A | 5/1998 | Ravenscroft |
| 5,755,771 A | 5/1998 | Penn et al. |
| 5,755,774 A | 5/1998 | Pinchuk |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,792,172 A | 8/1998 | Fischell et al. |
| 5,824,040 A | 10/1998 | Cox et al. |
| 5,824,055 A | 10/1998 | Spiridigliozzi et al. |
| 5,827,321 A | 10/1998 | Roubin |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,925,076 A | 7/1999 | Inoue |
| 5,944,750 A | 8/1999 | Tanner et al. |
| 5,948,018 A | 9/1999 | Dereume et al. |
| 5,968,091 A | 10/1999 | Pinchuk et al. |
| 5,976,178 A | 11/1999 | Goldsteen et al. |
| 5,980,552 A | 11/1999 | Pinchasik |
| 5,984,955 A | 11/1999 | Wisselink |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,723 A | 3/2000 | Anidjar et al. |
| 6,036,725 A | 3/2000 | Avellanet |
| 6,049,824 A | 4/2000 | Simonin |
| 6,051,021 A | 4/2000 | Frid |
| 6,059,824 A | 5/2000 | Taheri |
| 6,077,298 A | 6/2000 | Tu et al. |
| 6,099,497 A | 8/2000 | Adams et al. |
| 6,099,548 A | 8/2000 | Taheri |
| 6,117,145 A | 9/2000 | Wood et al. |
| 6,129,738 A | 10/2000 | Lashinski et al. |
| 6,132,457 A | 10/2000 | Chobotov |
| 6,152,956 A | 11/2000 | Pierce |
| 6,156,064 A | 12/2000 | Chouinard |
| 6,159,228 A | 12/2000 | Frid et al. |
| 6,168,615 B1 | 1/2001 | Ken et al. |
| 6,176,875 B1 | 1/2001 | Lenker et al. |
| 6,179,878 B1 | 1/2001 | Duerig et al. |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,287,335 B1 | 9/2001 | Drasler et al. |
| 6,290,720 B1 | 9/2001 | Khosravi et al. |
| 6,296,661 B1 | 10/2001 | Davila et al. |
| 6,312,458 B1 | 11/2001 | Golds |
| 6,319,287 B1 | 11/2001 | Frimberger |
| 6,325,819 B1 | 12/2001 | Pavcnik et al. |
| 6,325,823 B1 | 12/2001 | Horzewski et al. |
| 6,344,056 B1 | 2/2002 | Dehdashtian |
| 6,395,018 B1 | 5/2002 | Castaneda |
| 6,406,420 B1 | 6/2002 | McCarthy |
| 6,428,565 B1 | 8/2002 | Wisselink |
| 6,451,048 B1 | 9/2002 | Berg et al. |
| 6,451,051 B2 | 9/2002 | Drasler et al. |
| 6,471,722 B1 | 10/2002 | Inoue |
| 6,506,211 B1 | 1/2003 | Skubitz et al. |
| 6,520,988 B1 | 2/2003 | Colombo et al. |
| 6,544,279 B1 | 4/2003 | Hopkins et al. |
| 6,565,597 B1 | 5/2003 | Fearnot et al. |
| 6,576,009 B2 | 6/2003 | Ryan et al. |
| 6,613,075 B1 | 9/2003 | Healy et al. |
| 6,613,078 B1 | 9/2003 | Barone |
| 6,635,083 B1 | 10/2003 | Cheng et al. |
| 6,645,242 B1 | 11/2003 | Quinn |
| 6,648,901 B2 | 11/2003 | Fleischman et al. |
| 6,648,911 B1 | 11/2003 | Sirhan |

(56) References Cited

U.S. PATENT DOCUMENTS

| | | |
|---|---|---|
| 6,652,567 B1 | 11/2003 | Deaton |
| 6,652,571 B1 | 11/2003 | White et al. |
| 6,656,214 B1 | 12/2003 | Fogarty et al. |
| 6,673,080 B2 | 1/2004 | Reynolds et al. |
| 6,692,520 B1 | 2/2004 | Gambale et al. |
| 6,695,833 B1 | 2/2004 | Frantzen |
| 6,695,875 B2 | 2/2004 | Stelter et al. |
| 6,699,277 B1 | 3/2004 | Freidberg et al. |
| 6,716,238 B2 | 4/2004 | Elliot |
| 6,729,356 B1 | 5/2004 | Baker et al. |
| 6,730,117 B1 | 5/2004 | Tseng et al. |
| 6,733,523 B2 | 5/2004 | Shaolian et al. |
| 6,743,195 B2 | 6/2004 | Zucker |
| 6,748,953 B2 | 6/2004 | Sherry et al. |
| 6,752,826 B2 | 6/2004 | Wholey et al. |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,843,803 B2 | 1/2005 | Ryan et al. |
| 6,846,321 B2 | 1/2005 | Zucker |
| 6,860,900 B2 | 3/2005 | Clerc et al. |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,953,469 B2 | 10/2005 | Ryan |
| 6,964,679 B1 | 11/2005 | Marcade et al. |
| 6,986,774 B2 | 1/2006 | Middleman et al. |
| 7,008,441 B2 | 3/2006 | Zucker |
| 7,018,400 B2 | 3/2006 | Lashinski et al. |
| 7,022,131 B1 | 4/2006 | DeRowe et al. |
| 7,044,962 B2 | 5/2006 | Elliott |
| 7,083,822 B2 | 8/2006 | Brightbill |
| 7,105,015 B2 | 9/2006 | Goshgarian |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,122,052 B2 | 10/2006 | Greenhalgh |
| 7,131,991 B2 | 11/2006 | Zarins et al. |
| 7,144,421 B2 | 12/2006 | Carpenter et al. |
| 7,160,318 B2 | 1/2007 | Greenberg et al. |
| 7,175,651 B2 | 2/2007 | Kerr |
| 7,198,638 B2 | 4/2007 | Dong |
| 7,201,772 B2 | 4/2007 | Schwammenthal et al. |
| 7,220,274 B1 | 5/2007 | Quinn |
| 7,223,266 B2 | 5/2007 | Lindenbaum et al. |
| 7,261,733 B1 | 8/2007 | Brown et al. |
| 7,270,675 B2 | 9/2007 | Chun et al. |
| 7,279,003 B2 | 10/2007 | Berra et al. |
| 7,294,145 B2 | 11/2007 | Ward |
| 7,294,147 B2 | 11/2007 | Hartley |
| 7,306,623 B2 | 12/2007 | Watson |
| 7,341,598 B2 | 3/2008 | Davidson et al. |
| 7,393,357 B2 | 7/2008 | Stelter et al. |
| 7,396,363 B2 | 7/2008 | Frid |
| 7,399,313 B2 | 7/2008 | Brown et al. |
| 7,407,509 B2 | 8/2008 | Greenberg et al. |
| 7,413,573 B2 | 8/2008 | Hartley et al. |
| 7,425,219 B2 | 9/2008 | Quadri |
| 7,429,269 B2 | 9/2008 | Schwammenthal et al. |
| 7,438,721 B2 | 10/2008 | Doig et al. |
| 7,442,204 B2 | 10/2008 | Schwammenthal et al. |
| 7,473,272 B2 | 1/2009 | Pryor |
| 7,491,231 B2 | 2/2009 | Nazzaro et al. |
| 7,537,606 B2 | 5/2009 | Hartley et al. |
| 7,537,609 B2 | 5/2009 | Davidson et al. |
| 7,540,881 B2 | 6/2009 | Meyer et al. |
| 7,544,160 B2 | 6/2009 | Gross |
| 7,575,590 B2 | 8/2009 | Watson |
| 7,616,997 B2 | 11/2009 | Kieval et al. |
| 7,637,939 B2 | 12/2009 | Tischler |
| 7,645,298 B2 | 1/2010 | Hartley et al. |
| 7,655,036 B2 | 2/2010 | Goodson |
| 7,662,161 B2 | 2/2010 | Briganti et al. |
| 7,662,168 B2 | 2/2010 | McGuckin, Jr. et al. |
| 7,670,369 B2 | 3/2010 | Schaeffer |
| 7,678,141 B2 | 3/2010 | Greenan et al. |
| 7,699,885 B2 | 4/2010 | Leonhardt et al. |
| 7,708,704 B2 | 5/2010 | Mitelberg |
| 7,722,626 B2 | 5/2010 | Middleman et al. |
| 7,731,732 B2 | 6/2010 | Ken |
| 7,766,955 B2 | 8/2010 | Vardi et al. |
| 7,771,465 B2 | 8/2010 | Zukowski |
| 7,789,903 B2 | 9/2010 | Spiridigliozzi et al. |
| 7,803,177 B2 | 9/2010 | Hartley et al. |
| 7,803,178 B2 | 9/2010 | Whirley |
| 7,806,923 B2 | 10/2010 | Moloney |
| 7,815,673 B2 | 10/2010 | Bloom et al. |
| 7,833,259 B2 | 11/2010 | Boatman |
| 7,846,194 B2 | 12/2010 | Hartley et al. |
| 7,850,725 B2 | 12/2010 | Vardi et al. |
| 7,867,270 B2 | 1/2011 | Hartley et al. |
| 7,887,575 B2 | 2/2011 | Kujawski |
| 7,914,572 B2 | 3/2011 | Hartley et al. |
| 7,955,373 B2 | 6/2011 | Sowinski et al. |
| 7,955,374 B2 | 6/2011 | Erickson et al. |
| 7,959,662 B2 | 6/2011 | Erbel et al. |
| 7,959,669 B2 | 6/2011 | Chalekian et al. |
| 7,998,186 B2 | 8/2011 | Hartley |
| 7,998,187 B2 | 8/2011 | Hartley et al. |
| 8,012,193 B2 | 9/2011 | Hartley et al. |
| 8,016,853 B2 | 9/2011 | Griffen et al. |
| 8,021,412 B2 | 9/2011 | Hartley et al. |
| 8,021,418 B2 | 9/2011 | Gerberding et al. |
| 8,021,419 B2 | 9/2011 | Hartley et al. |
| 8,043,365 B2 | 10/2011 | Thramann |
| 8,048,139 B2 | 11/2011 | Frid et al. |
| 8,048,140 B2 | 11/2011 | Purdy |
| 8,048,147 B2 | 11/2011 | Adams |
| 8,052,736 B2 | 11/2011 | Doig et al. |
| 8,052,741 B2 | 11/2011 | Bruszewski et al. |
| 8,066,755 B2 | 11/2011 | Zacharias |
| 8,080,026 B2 | 12/2011 | Konstantino et al. |
| 8,080,053 B2 | 12/2011 | Satasiya |
| 8,100,960 B2 | 1/2012 | Bruszewski |
| 8,118,854 B2 | 2/2012 | Bowe |
| 8,133,267 B2 | 3/2012 | Leonhardt et al. |
| 8,157,810 B2 | 4/2012 | Case et al. |
| 8,157,852 B2 | 4/2012 | Bloom et al. |
| 8,167,926 B2 | 5/2012 | Hartley et al. |
| 8,172,892 B2 | 5/2012 | Chuter |
| 8,172,895 B2 | 5/2012 | Anderson et al. |
| 8,197,475 B2 | 6/2012 | Bruszewski et al. |
| 8,197,533 B2 | 6/2012 | Kujawski |
| 8,211,158 B2 | 7/2012 | Wolf |
| 8,216,298 B2 | 7/2012 | Wright et al. |
| 8,221,494 B2 | 7/2012 | Schreck et al. |
| 8,226,706 B2 | 7/2012 | Hartley et al. |
| 8,236,040 B2 | 8/2012 | Mayberry et al. |
| 8,251,963 B2 | 8/2012 | Chin et al. |
| 8,257,423 B2 | 9/2012 | Kerr |
| 8,262,719 B2 | 9/2012 | Erickson et al. |
| 8,273,115 B2 | 9/2012 | Hamer et al. |
| 8,287,586 B2 | 10/2012 | Schaeffer et al. |
| 8,292,885 B2 | 10/2012 | Bruszewski et al. |
| 8,292,941 B2 | 10/2012 | Muzslay |
| 8,292,949 B2 | 10/2012 | Berra et al. |
| 8,292,951 B2 | 10/2012 | Muzslay |
| 8,333,800 B2 | 12/2012 | Bruszewski et al. |
| 8,337,546 B2 | 12/2012 | Bruszewski |
| 8,353,898 B2 | 1/2013 | Lutze et al. |
| 8,357,192 B2 | 1/2013 | Mayberry et al. |
| 8,361,134 B2 | 1/2013 | Hartley et al. |
| 8,394,136 B2 | 3/2013 | Hartley et al. |
| 8,425,585 B2 | 4/2013 | Melsheimer et al. |
| 8,470,018 B2 | 6/2013 | Hartley et al. |
| 8,475,513 B2 | 7/2013 | Sithian |
| 8,480,726 B2 | 7/2013 | Cunningham et al. |
| 8,486,131 B2 | 7/2013 | Shalev |
| 8,491,646 B2 | 7/2013 | Schreck |
| 8,506,622 B2 | 8/2013 | Bruszewski et al. |
| 8,728,148 B2 | 5/2014 | Roeder et al. |

(56) References Cited

U.S. PATENT DOCUMENTS

| | | |
|---|---|---|
| 8,808,355 B2 | 8/2014 | Barrand |
| 8,945,203 B2 | 2/2015 | Shalev et al. |
| 8,968,384 B2 | 3/2015 | Pearson et al. |
| 9,101,457 B2 | 8/2015 | Benary |
| 9,168,123 B2 | 10/2015 | Barrand |
| 9,254,209 B2 | 2/2016 | Shalev |
| 9,278,018 B2 * | 3/2016 | Roeder .................. A61F 2/966 |
| 9,526,638 B2 | 12/2016 | Shalev et al. |
| 9,597,204 B2 | 3/2017 | Benary et al. |
| 2001/0000188 A1 | 4/2001 | Lenker et al. |
| 2001/0003161 A1 | 6/2001 | Vardi et al. |
| 2001/0004705 A1 | 6/2001 | Killion |
| 2001/0010006 A1 | 7/2001 | Bachinski et al. |
| 2001/0014823 A1 | 8/2001 | Resseman et al. |
| 2001/0034550 A1 | 10/2001 | Buirge |
| 2001/0037142 A1 | 11/2001 | Stelter et al. |
| 2001/0044647 A1 | 11/2001 | Pinchuk et al. |
| 2001/0044651 A1 | 11/2001 | Steinke |
| 2001/0044652 A1 | 11/2001 | Moore |
| 2001/0047198 A1 | 11/2001 | Drasler |
| 2001/0049550 A1 | 12/2001 | Martin et al. |
| 2001/0053930 A1 | 12/2001 | Kugler et al. |
| 2002/0040236 A1 | 4/2002 | Lau |
| 2002/0052643 A1 | 5/2002 | Wholey et al. |
| 2002/0052644 A1 | 5/2002 | Shaolian et al. |
| 2002/0072790 A1 | 6/2002 | McGuckin et al. |
| 2002/0099438 A1 | 7/2002 | Furst |
| 2002/0099441 A1 | 7/2002 | Dehdashtian |
| 2002/0107564 A1 | 8/2002 | Cox |
| 2002/0111667 A1 | 8/2002 | Girton et al. |
| 2002/0123791 A1 | 9/2002 | Harrison |
| 2002/0156495 A1 | 10/2002 | Brenneman et al. |
| 2002/0156517 A1 | 10/2002 | Prouse et al. |
| 2002/0173809 A1 | 11/2002 | Fleischman et al. |
| 2002/0183783 A1 | 12/2002 | Shadduck |
| 2002/0193864 A1 | 12/2002 | Khosravi et al. |
| 2002/0198585 A1 | 12/2002 | Wisselink |
| 2003/0033005 A1 | 2/2003 | Houser et al. |
| 2003/0040791 A1 | 2/2003 | Oktay |
| 2003/0040804 A1 | 2/2003 | Stack et al. |
| 2003/0057156 A1 | 3/2003 | Peterson et al. |
| 2003/0065345 A1 | 4/2003 | Weadock |
| 2003/0065386 A1 | 4/2003 | Weadock |
| 2003/0074055 A1 | 4/2003 | Haverkost |
| 2003/0093145 A1 | 5/2003 | Lawrence-Brown et al. |
| 2003/0114061 A1 | 6/2003 | Matsuda et al. |
| 2003/0125796 A1 | 7/2003 | Dong |
| 2003/0130720 A1 | 7/2003 | DePalma et al. |
| 2003/0139802 A1 | 7/2003 | Wulfman et al. |
| 2003/0139805 A1 | 7/2003 | Holmberg et al. |
| 2003/0144725 A1 | 7/2003 | Lombardi |
| 2003/0153944 A1 | 8/2003 | Phung et al. |
| 2003/0153968 A1 | 8/2003 | Geis et al. |
| 2003/0163187 A1 | 8/2003 | Weber |
| 2003/0171771 A1 | 9/2003 | Anderson et al. |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0204236 A1 | 10/2003 | Letort |
| 2003/0204242 A1 | 10/2003 | Zarins et al. |
| 2003/0204243 A1 | 10/2003 | Shiu |
| 2003/0208192 A1 | 11/2003 | Truckai et al. |
| 2003/0212449 A1 | 11/2003 | Cox |
| 2003/0233117 A1 | 12/2003 | Adams et al. |
| 2003/0236567 A1 | 12/2003 | Elliot |
| 2004/0015227 A1 | 1/2004 | Vardi et al. |
| 2004/0015229 A1 | 1/2004 | Fulkerson |
| 2004/0073289 A1 | 4/2004 | Hartley |
| 2004/0098091 A1 | 5/2004 | Erbel |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0138735 A1 | 7/2004 | Shaolian et al. |
| 2004/0162606 A1 | 8/2004 | Thompson |
| 2004/0171978 A1 | 9/2004 | Shalaby |
| 2004/0176832 A1 | 9/2004 | Hartley et al. |
| 2004/0181149 A1 | 9/2004 | Langlotz et al. |
| 2004/0215319 A1 | 10/2004 | Berra et al. |
| 2004/0215320 A1 | 10/2004 | Machek |
| 2004/0215327 A1 | 10/2004 | Doig et al. |
| 2004/0215332 A1 | 10/2004 | Frid |
| 2004/0260383 A1 | 12/2004 | Stelter et al. |
| 2005/0010246 A1 | 1/2005 | Streeter et al. |
| 2005/0033406 A1 | 2/2005 | Barnhart et al. |
| 2005/0049678 A1 | 3/2005 | Cocks et al. |
| 2005/0059923 A1 | 3/2005 | Gamboa |
| 2005/0065545 A1 | 3/2005 | Wallace |
| 2005/0070995 A1 | 3/2005 | Zilla et al. |
| 2005/0085900 A1 | 4/2005 | Case |
| 2005/0102018 A1 | 5/2005 | Carpenter et al. |
| 2005/0102021 A1 | 5/2005 | Osborne |
| 2005/0131512 A1 | 6/2005 | Vonderwalde |
| 2005/0131517 A1 | 6/2005 | Hartley et al. |
| 2005/0137682 A1 | 6/2005 | Justino |
| 2005/0143802 A1 | 6/2005 | Soykan et al. |
| 2005/0149166 A1 | 7/2005 | Schaeffer et al. |
| 2005/0154448 A1 | 7/2005 | Cully |
| 2005/0159803 A1 | 7/2005 | Lad et al. |
| 2005/0165480 A1 | 7/2005 | Jordan et al. |
| 2005/0171598 A1 | 8/2005 | Schaeffer et al. |
| 2005/0171599 A1 | 8/2005 | White |
| 2005/0177132 A1 | 8/2005 | Lentz et al. |
| 2005/0177222 A1 | 8/2005 | Mead |
| 2005/0177224 A1 | 8/2005 | Fogarty et al. |
| 2005/0203606 A1 | 9/2005 | VanCamp |
| 2005/0216018 A1 | 9/2005 | Sennett et al. |
| 2005/0222649 A1 | 10/2005 | Capuano |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0228480 A1 | 10/2005 | Douglas et al. |
| 2005/0234542 A1 | 10/2005 | Melsheimer |
| 2005/0266042 A1 | 12/2005 | Tseng |
| 2005/0273155 A1 | 12/2005 | Bahler et al. |
| 2005/0283188 A1 | 12/2005 | Loshakove et al. |
| 2006/0015170 A1 | 1/2006 | Jones et al. |
| 2006/0030911 A1 | 2/2006 | Letort |
| 2006/0030921 A1 | 2/2006 | Chu |
| 2006/0052799 A1 | 3/2006 | Middleman et al. |
| 2006/0069426 A1 | 3/2006 | Weinberger |
| 2006/0095104 A1 | 5/2006 | Magers et al. |
| 2006/0095114 A1 | 5/2006 | Hartley et al. |
| 2006/0100684 A1 | 5/2006 | Elliott |
| 2006/0106406 A1 | 5/2006 | Weinberger |
| 2006/0116748 A1 | 6/2006 | Kaplan et al. |
| 2006/0142703 A1 | 6/2006 | Carter et al. |
| 2006/0142836 A1 | 6/2006 | Hartley et al. |
| 2006/0149360 A1 | 7/2006 | Schwammenthal et al. |
| 2006/0155358 A1 | 7/2006 | LaDuca et al. |
| 2006/0155359 A1 | 7/2006 | Watson |
| 2006/0155366 A1 | 7/2006 | LaDuca et al. |
| 2006/0167476 A1 | 7/2006 | Burdulis, Jr. et al. |
| 2006/0173528 A1 | 8/2006 | Feld et al. |
| 2006/0173530 A1 | 8/2006 | Das |
| 2006/0178733 A1 | 8/2006 | Pinchuk et al. |
| 2006/0190070 A1 | 8/2006 | Dieck et al. |
| 2006/0193892 A1 | 8/2006 | Furst et al. |
| 2006/0212113 A1 | 9/2006 | Shaolian et al. |
| 2006/0229709 A1 | 10/2006 | Morris et al. |
| 2006/0241740 A1 | 10/2006 | Vardi et al. |
| 2006/0271166 A1 | 11/2006 | Thill et al. |
| 2006/0276882 A1 | 12/2006 | Case et al. |
| 2006/0281966 A1 | 12/2006 | Peacock, III |
| 2007/0016281 A1 | 1/2007 | Melsheimer |
| 2007/0021822 A1 | 1/2007 | Boatman |
| 2007/0027526 A1 | 2/2007 | Demetriades et al. |
| 2007/0043425 A1 | 2/2007 | Hartley et al. |
| 2007/0050011 A1 | 3/2007 | Klein |
| 2007/0055326 A1 | 3/2007 | Farley et al. |
| 2007/0055350 A1 | 3/2007 | Erickson et al. |
| 2007/0055358 A1 | 3/2007 | Krolik et al. |
| 2007/0055360 A1 | 3/2007 | Hanson et al. |
| 2007/0060989 A1 | 3/2007 | Deem et al. |

(56) References Cited

U.S. PATENT DOCUMENTS

| | | |
|---|---|---|
| 2007/0061002 A1 | 3/2007 | Paul, Jr. |
| 2007/0067014 A1 | 3/2007 | Ke et al. |
| 2007/0073373 A1 | 3/2007 | Bonsignore |
| 2007/0088425 A1 | 4/2007 | Schaeffer |
| 2007/0106368 A1 | 5/2007 | Vonderwalde |
| 2007/0112344 A1 | 5/2007 | Keilman |
| 2007/0135677 A1 | 6/2007 | Miller et al. |
| 2007/0135904 A1 | 6/2007 | Eidenschink |
| 2007/0142896 A1 | 6/2007 | Anderson et al. |
| 2007/0150051 A1 | 6/2007 | Arnault de la et al. |
| 2007/0156167 A1 | 7/2007 | Connors et al. |
| 2007/0162104 A1 | 7/2007 | Frid |
| 2007/0167898 A1 | 7/2007 | Peters et al. |
| 2007/0167955 A1 | 7/2007 | Arnault De La Menardiere et al. |
| 2007/0168013 A1 | 7/2007 | Douglas |
| 2007/0168018 A1 | 7/2007 | Amplatz |
| 2007/0179598 A1 | 8/2007 | Duerig |
| 2007/0185565 A1 | 8/2007 | Schwammenthal et al. |
| 2007/0208410 A1 | 9/2007 | Berra et al. |
| 2007/0213805 A1 | 9/2007 | Schaeffer et al. |
| 2007/0213807 A1 | 9/2007 | Roubin |
| 2007/0219610 A1 | 9/2007 | Israel |
| 2007/0219614 A1 | 9/2007 | Hartley |
| 2007/0219627 A1 | 9/2007 | Chu |
| 2007/0225797 A1 | 9/2007 | Krivoruhko |
| 2007/0233220 A1* | 10/2007 | Greenan .................. A61F 2/07 623/1.11 |
| 2007/0233229 A1 | 10/2007 | Berra et al. |
| 2007/0237973 A1 | 10/2007 | Purdy et al. |
| 2007/0239256 A1 | 10/2007 | Weber et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0015682 A1 | 1/2008 | Majercak et al. |
| 2008/0033527 A1 | 2/2008 | Nunez et al. |
| 2008/0058918 A1 | 3/2008 | Watson |
| 2008/0064957 A1 | 3/2008 | Spence |
| 2008/0086193 A1 | 4/2008 | Thramann |
| 2008/0097578 A1 | 4/2008 | Erickson et al. |
| 2008/0109058 A1 | 5/2008 | Greenberg et al. |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0114446 A1 | 5/2008 | Hartley et al. |
| 2008/0140178 A1 | 6/2008 | Rasmussen et al. |
| 2008/0147173 A1 | 6/2008 | McIff et al. |
| 2008/0167704 A1 | 7/2008 | Wright et al. |
| 2008/0176271 A1 | 7/2008 | Silver et al. |
| 2008/0195190 A1 | 8/2008 | Bland et al. |
| 2008/0195191 A1 | 8/2008 | Luo |
| 2008/0215134 A1 | 9/2008 | Lawrence-Brown |
| 2008/0249598 A1 | 10/2008 | Sherry |
| 2008/0262595 A1 | 10/2008 | Chu et al. |
| 2008/0262598 A1 | 10/2008 | Elmaleh |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz |
| 2008/0312732 A1 | 12/2008 | Hartley et al. |
| 2008/0319528 A1 | 12/2008 | Yribarren et al. |
| 2009/0005863 A1 | 1/2009 | Goetz et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang |
| 2009/0069881 A1 | 3/2009 | Chalekian et al. |
| 2009/0069882 A1 | 3/2009 | Venturelli |
| 2009/0082841 A1 | 3/2009 | Zacharias |
| 2009/0082847 A1 | 3/2009 | Zacharias et al. |
| 2009/0099640 A1 | 4/2009 | Weng |
| 2009/0099647 A1 | 4/2009 | Glimsdale et al. |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0157014 A1 | 6/2009 | Osborne et al. |
| 2009/0164001 A1 | 6/2009 | Biggs et al. |
| 2009/0171437 A1 | 7/2009 | Brocker et al. |
| 2009/0182270 A1 | 7/2009 | Nanavati |
| 2009/0182405 A1 | 7/2009 | Arnault De La Menardiere et al. |
| 2009/0227997 A1 | 9/2009 | Wang |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2009/0319022 A1 | 12/2009 | Hartley et al. |
| 2010/0004728 A1 | 1/2010 | Rao |
| 2010/0029608 A1 | 2/2010 | Finley |
| 2010/0057186 A1 | 3/2010 | West et al. |
| 2010/0063575 A1 | 3/2010 | Shalev |
| 2010/0070019 A1 | 3/2010 | Shalev |
| 2010/0082091 A1 | 4/2010 | Berez |
| 2010/0161025 A1 | 6/2010 | Kuppurathanam et al. |
| 2010/0161026 A1 | 6/2010 | Brocker et al. |
| 2010/0161028 A1 | 6/2010 | Chuter et al. |
| 2010/0168838 A1 | 7/2010 | Hartley et al. |
| 2010/0211159 A1 | 8/2010 | Schmid |
| 2010/0249899 A1 | 9/2010 | Chuter et al. |
| 2010/0256725 A1 | 10/2010 | Rasmussen |
| 2010/0262227 A1 | 10/2010 | Rangwala et al. |
| 2010/0268327 A1 | 10/2010 | Bruszewski et al. |
| 2010/0274187 A1 | 10/2010 | Argentine |
| 2010/0274345 A1 | 10/2010 | Rust |
| 2010/0292774 A1 | 11/2010 | Shalev |
| 2010/0312326 A1 | 12/2010 | Chuter et al. |
| 2010/0318171 A1 | 12/2010 | Porter |
| 2010/0318180 A1 | 12/2010 | Porter |
| 2011/0022149 A1 | 1/2011 | Cox et al. |
| 2011/0022153 A1 | 1/2011 | Schreck et al. |
| 2011/0040366 A1 | 2/2011 | Goetz et al. |
| 2011/0093002 A1 | 4/2011 | Rucker et al. |
| 2011/0125251 A1 | 5/2011 | Cottone |
| 2011/0152998 A1 | 6/2011 | Berez et al. |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0218609 A1 | 9/2011 | Chobotov et al. |
| 2011/0218617 A1 | 9/2011 | Nguyen et al. |
| 2011/0319983 A1 | 9/2011 | Zhu et al. |
| 2011/0257720 A1 | 10/2011 | Peterson et al. |
| 2011/0257725 A1 | 10/2011 | Argentine et al. |
| 2011/0262684 A1 | 10/2011 | Wintsch et al. |
| 2011/0264184 A1 | 10/2011 | Heltai |
| 2011/0264192 A1 | 10/2011 | Hartley et al. |
| 2011/0270385 A1 | 11/2011 | Muzslay |
| 2011/0288622 A1 | 11/2011 | Chan et al. |
| 2011/0301702 A1 | 12/2011 | Rust et al. |
| 2012/0143317 A1 | 6/2012 | Cam et al. |
| 2012/0150274 A1 | 6/2012 | Shalev et al. |
| 2012/0158038 A1 | 6/2012 | Leschinsky |
| 2012/0172929 A1 | 7/2012 | Shalev |
| 2012/0172965 A1 | 7/2012 | Kratzberg et al. |
| 2012/0179236 A1 | 7/2012 | Benary et al. |
| 2012/0185031 A1 | 7/2012 | Ryan et al. |
| 2012/0271401 A1 | 10/2012 | Bruszewski et al. |
| 2012/0310324 A1 | 12/2012 | Benary et al. |
| 2012/0316634 A1 | 12/2012 | Shalev et al. |
| 2012/0323305 A1 | 12/2012 | Benary et al. |

(56) References Cited

U.S. PATENT DOCUMENTS

| | | |
|---|---|---|
| 2012/0330399 A1 | 12/2012 | Shalev et al. |
| 2013/0013050 A1 | 1/2013 | Shalev et al. |
| 2013/0013051 A1 | 1/2013 | Benary |
| 2013/0035751 A1 | 2/2013 | Shalev |
| 2013/0090722 A1 | 4/2013 | Shalev et al. |
| 2013/0116773 A1 | 5/2013 | Roeder et al. |
| 2013/0116775 A1 | 5/2013 | Roeder et al. |
| 2013/0131783 A1 | 5/2013 | Shalev et al. |
| 2013/0158646 A1 | 6/2013 | Roeder |
| 2013/0197454 A1 | 8/2013 | Shibata et al. |
| 2013/0204311 A1 | 8/2013 | Kunis |
| 2013/0204343 A1 | 8/2013 | Shalev |
| 2013/0261994 A1 | 10/2013 | Raz et al. |
| 2013/0274866 A1 | 10/2013 | Cox et al. |
| 2013/0289587 A1 | 10/2013 | Shalev |
| 2013/0289691 A1* | 10/2013 | Argentine .............. A61F 2/966 623/1.11 |
| 2013/0297005 A1 | 11/2013 | Shalev |
| 2013/0338753 A1 | 12/2013 | Geusen |
| 2013/0338787 A1 | 12/2013 | Hopkins et al. |
| 2014/0005764 A1 | 1/2014 | Schroeder |
| 2014/0052236 A1 | 2/2014 | Shalev |
| 2014/0148888 A1 | 5/2014 | Barrand |
| 2014/0172072 A1 | 6/2014 | Shalev |
| 2014/0180378 A1 | 6/2014 | Roeder |
| 2014/0288634 A1 | 9/2014 | Shalev |
| 2014/0288635 A1 | 9/2014 | Shalev |
| 2014/0316510 A1 | 10/2014 | Berra |
| 2014/0324154 A1 | 10/2014 | Shalev |
| 2014/0350658 A1 | 11/2014 | Benary et al. |
| 2014/0364930 A1 | 12/2014 | Strauss et al. |
| 2015/0073534 A1 | 3/2015 | Roeder et al. |
| 2015/0105851 A1 | 4/2015 | Shalev et al. |
| 2015/0142096 A1 | 5/2015 | Shalev |
| 2015/0196301 A1 | 7/2015 | Bodewadt et al. |
| 2015/0202065 A1 | 7/2015 | Shalev et al. |
| 2015/0351943 A1 | 12/2015 | Shalev et al. |
| 2015/0374383 A1 | 12/2015 | Bodewadt et al. |
| 2016/0030209 A1 | 2/2016 | Shalev et al. |
| 2016/0157990 A1 | 6/2016 | Shalev et al. |
| 2016/0193029 A1 | 7/2016 | Shalev |
| 2016/0262880 A1 | 9/2016 | Li et al. |

FOREIGN PATENT DOCUMENTS

| | | |
|---|---|---|
| CN | 2453960 | 10/2001 |
| CN | 1748660 | 3/2006 |
| CN | 2817770 | 9/2006 |
| CN | 101045022 | 10/2007 |
| CN | 201058061 | 5/2008 |
| CN | 101980670 | 2/2011 |
| CN | 101998845 | 3/2011 |
| DE | 10213055 | 9/2002 |
| EP | 0893108 | 1/1999 |
| EP | 1 177 779 | 2/2002 |
| EP | 1 177 780 | 2/2002 |
| EP | 1 325 716 | 7/2003 |
| EP | 1470797 | 10/2004 |
| EP | 1759666 | 3/2007 |
| EP | 1961401 | 8/2008 |
| EP | 2266509 | 12/2010 |
| EP | 2298248 | 3/2011 |
| JP | 2000-279533 | 10/2000 |
| JP | 2002-253682 | 9/2002 |
| WO | 1996/039104 | 12/1996 |
| WO | 98/06355 | 2/1998 |
| WO | 1998/027895 | 7/1998 |
| WO | 99/13808 | 3/1999 |
| WO | 1999/025273 | 5/1999 |
| WO | 99/34748 | 7/1999 |
| WO | 1999/051165 | 10/1999 |
| WO | 00/28923 | 5/2000 |
| WO | 2000/074595 | 12/2000 |
| WO | 2000/076423 | 12/2000 |
| WO | 2002/083038 | 10/2002 |
| WO | 2003/034948 | 5/2003 |
| WO | 03/099108 | 12/2003 |
| WO | 2004/017868 | 3/2004 |
| WO | 2004/045463 | 6/2004 |
| WO | 2004/100836 | 11/2004 |
| WO | 05/002466 | 1/2005 |
| WO | 2005/034809 | 4/2005 |
| WO | 2005/037138 | 4/2005 |
| WO | 2005/041781 | 5/2005 |
| WO | 2005/041783 | 5/2005 |
| WO | 2005/046524 | 5/2005 |
| WO | 2005/046526 | 5/2005 |
| WO | 2006/007389 | 1/2006 |
| WO | 2006/028925 | 3/2006 |
| WO | 2006/036690 | 4/2006 |
| WO | 06/070372 | 7/2006 |
| WO | 2006/088905 | 8/2006 |
| WO | 2006/130755 | 12/2006 |
| WO | 2007/022495 | 2/2007 |
| WO | 2007/039587 | 4/2007 |
| WO | 2007/084547 | 7/2007 |
| WO | 2007/115017 | 10/2007 |
| WO | 2007/144782 | 12/2007 |
| WO | 08/008291 | 1/2008 |
| WO | 2008/021557 | 2/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/051704 | 5/2008 |
| WO | 2008/053469 | 5/2008 |
| WO | 2008/066923 | 6/2008 |
| WO | 2008/107885 | 9/2008 |
| WO | 2008/140796 | 11/2008 |
| WO | 2009/078010 | 6/2009 |
| WO | 2009/082444 | 7/2009 |
| WO | 2009/104000 | 8/2009 |
| WO | 2009/116041 | 9/2009 |
| WO | 2009/116042 | 9/2009 |
| WO | 09/118733 | 10/2009 |
| WO | 2010/024869 | 3/2010 |
| WO | 2010/024879 | 3/2010 |
| WO | 2010/027704 | 3/2010 |
| WO | 2010/031060 | 3/2010 |
| WO | 2010/042210 | 4/2010 |
| WO | 2010/045238 | 4/2010 |
| WO | 2010/062355 | 6/2010 |
| WO | 10/088776 | 8/2010 |
| WO | 2010/111583 | 9/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2001/052776 | 7/2011 |
| WO | 2011/080738 | 7/2011 |
| WO | 2011/095979 | 8/2011 |
| WO | 2011/100290 | 8/2011 |
| WO | 2011/106532 | 9/2011 |
| WO | 2011/106533 | 9/2011 |
| WO | 2011/106544 | 9/2011 |
| WO | 2011/116307 | 9/2011 |
| WO | 2011/136930 | 11/2011 |
| WO | 2012/039748 | 3/2012 |
| WO | 2012/049679 | 4/2012 |
| WO | 2012/104842 | 8/2012 |
| WO | 2012/111006 | 8/2012 |
| WO | 2012/117395 | 9/2012 |
| WO | 2012/176187 | 12/2012 |
| WO | 2013/005207 | 1/2013 |
| WO | 2013/021374 | 2/2013 |
| WO | 2013/030818 | 3/2013 |
| WO | 2013/030819 | 3/2013 |
| WO | 2013/065040 | 5/2013 |
| WO | 2013/069019 | 5/2013 |

(56) References Cited

FOREIGN PATENT DOCUMENTS

| WO | 2013/084235 | 6/2013 |
|---|---|---|
| WO | 2013/171730 | 11/2013 |
| WO | 2014/020609 | 2/2014 |
| WO | 2014/108895 | 7/2014 |
| WO | 2014/141232 | 9/2014 |
| WO | 2014/188412 | 11/2014 |

OTHER PUBLICATIONS

Khlif H et al., "Contribution to the Improvement of Textile Vascular Prostheses Crimping," Trends in Applied Sciences Research 6(9):1019-1027 (2011).
An International Search Report dated Sep. 29, 2008, which issued during the prosecution of Applicant's PCT/IL08/000287.
A Written Opinion dated Sep. 29, 2008, which issued during the prosecution of Applicant's PCT/IL08/000287.
An International Search Report & Written Opinion both dated Nov. 26, 2013, which issued during the prosecution of Applicant's PCT/IL2013/050656.
An International Search Report dated Feb. 4, 2011, which issued during the prosecution of Applicant's PCT/IB2010/052861.
A Written Opinion dated Feb. 4, 2011, which issued during the prosecution of Applicant's PCT/IB2010/052861.
An International Search Report dated Dec. 3, 2010, which issued during the prosecution of Applicant's PCT/IL2010/000564.
A Written Opinion dated Dec. 3, 2010, which issued during the prosecution of Applicant's PCT/IL2010/000564.
An International Search Report dated Nov. 5, 2010, which issued during the prosecution of Applicant's PCT/IL2010/000549.
A Written Opinion dated Nov. 5, 2010, which issued during the prosecution of Applicant's PCT/IL2010/000549.
An International Search Report dated Aug. 4, 2011, which issued during the prosecution of Applicant's PCT/IL2010/000999.
An International Search Report dated Mar. 10, 2011, which issued during the prosecution of Applicant's PCT/IL2010/000917.
An International Search Report together with Written Opinion both dated Mar. 30 2011, which issued during the prosecution of Applicant's PCT/IL2010/001018.
An International Search Report dated Apr. 18, 2011, which issued during the prosecution of Applicant's PCT/IL2010/001037.
An International Search Report dated May 23, 2011, which issued during the prosecution of Applicant's PCT/IL2010/001087.
An International Search Report dated Jun. 28, 2011, which issued during the prosecution of Applicant's PCT/IL2011/000135.
An International Search Report dated Jun. 30, 2009, which issued during the prosecution of Applicant's PCT/IL2008/001621.
A Written Opinion dated Jun. 30, 2009, which issued during the prosecution of Applicant's PCT/IL2008/001621.
An International Search Report dated Mar. 11, 2009, which issued during the prosecution of Applicant's PCT/IL2007/001312.
A Written Opinion dated Mar. 11, 2009, which issued during the prosecution of Applicant's PCT/IL2007/001312.
An English translation of an Office Action dated Aug. 25, 2011, which issued during the prosecution of Chinese Patent Application No. 200880014919.9.
An Office Action dated Nov. 12, 2010, which issued during the prosecution of U.S. Appl. No. 12/447,684.
An Office Action dated Apr. 27, 2011, which issued during the prosecution of U.S. Appl. No. 12/447,684.
An Office Action dated Feb. 25, 2013, which issued during the prosecution of U.S. Appl. No. 13/031,871.
An Office Action dated Feb. 27, 2013, which issued during the prosecution of U.S. Appl. No. 12/808,037.
An Extended European Search Report dated Dec. 13, 2012, which issued during the prosecution of Applicant's European App No. 08719912.1.
An International Search Report together with Written Opinion both dated Sep. 6, 2012, which issued during the prosecution of Applicant's PCT/IL2012/000190.
An International Search Report together with Written Opinion both dated Aug. 31, 2012, which issued during the prosecution of Applicant's PCT/IL2012/000148.
An Office Action dated Oct. 11, 2012, which issued during the prosecution of U.S. Appl. No. 13/031,871.
An Office Action dated Jun. 19, 2012, which issued during the prosecution of U.S. Appl. No. 12/808,037.
An International Search Report together with Written Opinion both dated Sep. 24, 2012, which issued during the prosecution of Applicant's PCT/IL2012/000060.
An International Search Report together with Written Opinion both dated Oct. 1, 2012, which issued during the prosecution of Applicant's PCT/IL2012/000241.
An International Search Report together with Written Opinion both dated Oct. 4, 2012, which issued during the prosecution of Applicant's PCT/IL2012/000269.
An International Search Report together with Written Opinion both dated Nov. 27, 2012, which issued during the prosecution of Applicant's PCT/IL2012/000300.
An Office Action dated Jul. 22, 2016, which issued during the prosecution of Chinese Patent Application No. 201480012648.9.
An Office Action dated Oct. 28, 2011, which issued during the prosecution of U.S. Appl. No. 12/529,936.
An Office Action dated Mar. 24, 2011, which issued during the prosecution of U.S. Appl. No. 12/529,936.
An International Search Report and a Written Opinion both dated Jun. 14, 2013, which issued during the prosecution of Applicant's PCT/IL2012/050506.
Van Prehn J et al., "Oversizing of aortic stent grafts for abdominal aneurysm repair: a systematic review of the benefits and risks," Eur J Vase Endovase Surg. Jul. 2009;38(1):42-53. Epub May 9, 2009 (abstract only).
Fattori et al., Degenerative aneurysm of the descending aorta. Endovascular Treatment. pp. 1-11, 2007, European Association for Cardio-Thoracic Surgery.
An Office Action dated Jan. 12, 2016, which issued during the prosecution of U.S. Appl. No. 14/362,194.
European Search Report dated Aug. 31, 2016, which issued during the prosecution of Applicant's European App No. 14762507.3.
An Office Action dated Feb. 5, 2015, which issued during the prosecution of U.S. Appl. No. 13/384,075.
An Office Action dated Feb. 23, 2015, which issued during the prosecution of U.S. Appl. No. 13/513,397.
European Search Report dated Feb. 26, 2015, which issued during the prosecution of Applicant's European App No. 12806964.8.
An International Search Report and a Written Opinion both dated Mar. 18, 2015, which issued during the prosecution of Applicant's PCT/IL2014/050973.
An English translation of an Office Action dated Mar. 19, 2015, which issued during the prosecution of Chinese Patent Application No. 201080036970.7.
An English translation of an Office Action dated Oct. 8, 2014, which issued during the prosecution of Chinese Patent Application No. 201080036970.7.
European Search Report dated May 23, 2016, which issued during the prosecution of Applicant's European App No. 10832752.9.
An Office Action dated Mar. 26, 2015, which issued during the prosecution of U.S. Appl. No. 13/514,240.
European Search Report dated Mar. 20, 2015, which issued during the prosecution of Applicant's European App No. 08861980.4.
An International Search Report and a Written Opinion both dated Jun. 21, 2016, which issued during the prosecution of Applicant's PCT/IL2016/050014.
An Office Action dated Aug. 12, 2015, which issued during the prosecution of U.S. Appl. No. 13/513,397.
European Search Report dated Sep. 22, 2016, which issued during the prosecution of Applicant's European App No. 10834308.8.
An Office Action dated Aug. 3, 2016, which issued during the prosecution of U.S. Appl. No. 14/241,793.
An Office Action dated Sep. 22, 2016, which issued during the prosecution of Canadian Patent Application No. 2,782,513.
An Office Action dated Sep. 23, 2015, which issued during the prosecution of U.S. Appl. No. 13/384,075.

(56) References Cited

OTHER PUBLICATIONS

An Office Action dated Oct. 2, 2015, which issued during the prosecution of U.S. Appl. No. 13/577,161.
European Search Report dated Apr. 22, 2015, which issued during the prosecution of Applicant's European App No. 12828495.7.
An Office Action dated Apr. 14, 2015, which issued during the prosecution of U.S. Appl. No. 14/130,213.
European Search Report dated Jan. 18, 2016 which issued during the prosecution of Applicant's European App No. 10799521.9.
European Search Report dated Oct. 27, 2015 which issued during the prosecution of Applicant's European App No. 10835608.0.
An Office Action dated Feb. 23, 2016, which issued during the prosecution of U.S. Appl. No. 14/416,236.
An Office Action dated Mar. 7, 2016, which issued during the prosecution of U.S. Appl. No. 14/240,600.
An Office Action dated Feb. 1, 2016, which issued during the prosecution of U.S. Appl. No. 14/241,793.
An Office Action dated Feb. 19, 2016, which issued during the prosecution of U.S. Appl. No. 13/807,880.
An International Search Report and a Written Opinion both dated Feb. 17, 2016, which issued during the prosecution of Applicant's PCT/IL2015/051221.
European Search Report dated Mar. 11, 2016 which issued during the prosecution of Applicant's European App No. 11739497.3.
European Search Report dated Mar. 15, 2016 which issued during the prosecution of Applicant's European App No. 13825456.0.
An Office Action dated Mar. 28, 2016, which issued during the prosecution of U.S. Appl. No. 14/362,194.
An Invitation to pay additional fees dated Apr. 12, 2016, which issued during the prosecution of Applicant's PCT/IL2016/050014.
An International Search Report and a Written Opinion both dated Apr. 22, 2016, which issued during the prosecution of Applicant's PCT/IL2016/050049.
Scurr et al., "Fenestrated Aortic Stent Grafts," Semin Intervent Radiol. Jun. 2007; 24(2): 211-220.
European Search Report dated Oct. 27, 2016 whoch issued during the prosecution of Applicant's European App No. 14801036.6.
U.S. Appl. No. 61/265,793, filed Dec. 2, 2009.
An International Search Report and a Written Opinion both dated Jul. 30, 2014, which issued during the prosecution of Applicant's PCT/IL2014/050174.
European Search Report dated Jun. 12, 2014, which issued during the prosecution of Applicant's European App No. 12855964.8.
An Office Action dated Feb. 3, 2015, which issued during the prosecution of U.S. Appl. No. 12/447,684.
Invitation to Pay Additional Fees dated May 13, 2014, which issued during the prosecution of Applicant's PCT/IL2014/050019.
U.S. Appl. No. 61/826,544, filed May 23, 2013.
U.S. Appl. No. 61/566,654, filed Dec. 4, 2011.
U.S. Appl. No. 61/014,031, filed Dec. 15, 2007.
U.S. Appl. No. 61/448,199, filed Mar. 2, 2011.
Invitation to Pay Additional Fees dated May 8, 2014, which issued during the prosecution of Applicant's PCT/IL2014/050174.
An Office Action dated Mar. 28, 2014, which issued during the prosecution of U.S. Appl. No. 13/519,971.
An International Search Report and a Written Opinion both dated Apr. 28, 2014, which issued during the prosecution of Applicant's PCT/IL2014/050019.
An Office Action dated Aug. 15, 2014, which issued during the prosecution of U.S. Appl. No. 13/512,778.
An Office Action dated Feb. 28, 2014, which issued during the prosecution of U.S. Appl. No. 13/512,778.
An Office Action dated Dec. 27, 2016, which issued during the prosecution of Chinese Patent Application No. 201510685240.4.
An Office Action dated Dec. 7, 2016, which issued during the prosecution of U.S. Appl. No. 14/400,699.
An Office Action dated Jan. 12, 2017, which issued during the prosecution of U.S. Appl. No. 14/518,542.
Aortic Aneurysm O'Gara, Patrick T. Circulation. 2003; 107:e43-e45.
An International Search Report and a Written Opinion both dated Jan. 19, 2017, which issued during the prosecution of Applicant's PCT/IL2016/051207.
An Office Action dated Mar. 6, 2017, which issued during the prosecution of U.S. Appl. No. 13/979,551.
An Office Action dated Jan. 26, 2017, which issued during the prosecution of U.S. Appl. No. 14/572,156.
Notice of Allowance dated Feb. 9, 2017, which issued during the prosecution of U.S. Appl. No. 14/772,016.
An International Preliminary Report on Patentability dated Jan. 7, 2014, which issued during the prosecution of Applicant's PCT/IL2012/000269.
An International Preliminary Report on Patentability dated Jan. 4, 2012, which issued during the prosecution of Applicant's PCT/IB2010/052861.
An International Preliminary Report on Patentability dated Dec. 23, 2013, which issued during the prosecution of Applicant's PCT/IL2012/000241.
An International Preliminary Report on Patentability dated Aug. 6, 2013, which issued during the prosecution of Applicant's PCT/IL2012/000060.
U.S. Appl. No. 61/438,977, filed Feb. 3, 2011.
Notice of Allowance dated Dec. 19, 2014, which issued during the prosecution of U.S. Appl. No. 13/512,778.
An Office Action dated Jul. 30, 2015, which issued during the prosecution of U.S. Appl. No. 14/240,600.
An Office Action dated Sep. 11, 2015, which issued during the prosecution of U.S. Appl. No. 14/001,641.
An Office Action dated May 15, 2015, which issued during the prosecution of U.S. Appl. No. 13/577,161.
An Office Action dated May 28, 2015, which issued during the prosecution of U.S. Appl. No. 14/240,600.
An Advisory Action dated Feb. 13, 2014, which issued during the prosecution of U.S. Appl. No. 13/807,880.
An Office Action dated May 20, 2013, which issued during the prosecution of U.S. Appl. No. 13/807,880.
Notice of Allowance dated Nov. 25, 2016, which issued during the prosecution of U.S. Appl. No. 13/807,880.
Notice of Allowance dated Sep. 27, 2016, which issued during the prosecution of U.S. Appl. No. 13/807,880.
Notice of Allowance dated Aug. 15, 2016, which issued during the prosecution of U.S. Appl. No. 13/807,880.
An Office Action dated Dec. 2, 2013, which issued during the prosecution of U.S. Appl. No. 13/807,880.
An Office Action dated Mar. 2, 2016, which issued during the prosecution of Chinese Patent Application No. 201480012648.9.
An Office Action dated Jan. 16, 2015, which issued during the prosecution of Chinese Patent Application No. 201080062714.5.
An Office Action dated Jun. 3, 2015, which issued during the prosecution of Chinese Patent Application No. 201080062714.5.
Notice of Allowance dated Aug. 5, 2015, which issued during the prosecution of Chinese Patent Application No. 201080062714.5.
An Office Action dated Jul. 2, 2014, which issued during the prosecution of Chinese Patent Application No. 201080062714.5.
Notice of Allowance dated Nov. 7, 2014, which issued during the prosecution of U.S. Appl. No. 13/512,778.
Notice of Allowance dated Oct. 8, 2014, which issued during the prosecution of U.S. Appl. No. 13/512,778.
An Office Action dated Jun. 18, 2013, which issued during the prosecution of U.S. Appl. No. 13/512,778.
Notice of Allowance dated Nov. 10, 2016, which issued during the prosecution of U.S. Appl. No. 14/362,194.
European Search Report dated Jun. 30, 2014, which issued during the prosecution of Applicant's European App No. 12741804.4.
An International Search Report and a Written Opinion both dated Jul. 17, 2012, which issued during the prosecution of Applicant's PCT/IL2012/000095.
An International Search Report and a Written Opinion both dated Jul. 13, 2012, which issued during the prosecution of Applicant's PCT/IL2012/000083.
An International Preliminary Report on Patentability dated Sep. 3, 2013, which issued during the prosecution of Applicant's PCT/IL2012/000095.

(56) References Cited

OTHER PUBLICATIONS

An International Search Report and a Written Opinion both dated Mar. 15, 2013, which issued during the prosecution of Applicant's PCT/IL2012/050424.
An English translation of an Office Action dated Jan. 28, 2014, which issued during the prosecution of Chinese Patent Application No. 201080036970.7.
An Office Action dated Apr. 28, 2014, which issued during the prosecution of Applicant's U.S. Appl. No. 13/939,798.
An Office Action dated Apr. 10, 2014, which issued during the prosecution of Applicant's U.S. Appl. No. 13/807,906.
An Office Action dated Apr. 24, 2014, which issued during the prosecution of Applicant's U.S. Appl. No. 13/380,278.
Supplementary European Search Report dated Feb. 17, 2014, which issued during the prosecution of Applicant's European App No. 12803376.8.
An Office Action dated Jul. 24, 2014, which issued during the prosecution of Canadian Patent Application No. 2768228.
U.S. Appl. No. 61/264,861, filed Nov. 30, 2009.
An Interview Summary dated Sep. 25, 2014, which issued during the prosecution of U.S. Appl. No. 13/512,778.
An Interview Summary dated Apr. 24, 2014, which issued during the prosecution of U.S. Appl. No. 13/512,778.
Ryhanen J., in "Biocompatibility evaluation of nickel-titanium shape memory metal alloy," Academic Dissertation, Faculty of Medicine, Department of Surgery, University of Oulu, Finland (May 1999).
An Office action dated Sep. 4, 2014, from the U.S. Patent and Trademark Office in counterpart U.S. Appl. No. 13/519,971.
An Office action dated Dec. 9, 2015, from the U.S. Patent and Trademark Office in counterpart U.S. Appl. No. 14/416,236.
An Office Action dated Apr. 14, 2016, which issued during the prosecution of Canadian Patent Application No. 2,766,347.
An Office Action dated Sep. 15, 2016, which issued during the prosecution of Canadian Patent Application No. 2,782,357.
European Office Action dated Dec. 17, 2014 in European Patent Application No. 12803376.8.
International Preliminary Report on Patentability dated Jan. 12, 2010 in corresponding International Application No. PCT/IL2008/000287.
U.S. Appl. No. 61/906,014, filed Nov. 19, 2013.
U.S. Appl. No. 61/775,964, filed Mar. 11, 2013.
U.S. Appl. No. 61/926,533, filed Jan. 13, 2014.
U.S. Appl. No. 61/528,242, filed Aug. 28, 2011.
An Office action dated Aug. 15, 2014, from the U.S. Patent and Trademark Office in counterpart U.S. Appl. No. 13/939,798.
A Notice of Allowance dated Jan. 20, 2015, which issued during the prosecution of U.S. Appl. No. 13/383,128.
An International Preliminary Report on Patentability dated Feb. 3, 2015, which issued during the prosecution of Applicant's PCT/IL2013/050656.
A Notice of Allowance dated Jan. 7, 2014, which issued during the prosecution of U.S. Appl. No. 13/663,117.
An Office Action dated Sep. 2, 2014, which issued during the prosecution of U.S. Appl. No. 12/447,684.
European Search Report dated Oct. 31, 2014, which issued during the prosecution of Applicant's European App No. 12752054.2.
Notice of allowance dated Jun. 24, 2014, which issued during the prosecution of Applicant's U.S. Appl. No. 13/380,278.
An Interview Summary dated Dec. 13, 2010, which issued during the prosecution of U.S. Appl. No. 12/447,684.
An Office Action dated Mar. 21, 2012, which issued during the prosecution of U.S. Appl. No. 12/808,037.
Notice of allowance dated May 22, 2013, which issued during the prosecution of U.S. Appl. No. 12/808,037.
An English translation of an Office Action dated Nov. 28, 2013, which issued during the prosecution of Chinese Patent Application No. 200880126889.0.
An English translation of an Office Action dated May 16, 2014, which issued during the prosecution of Chinese Patent Application No. 200880126889.0.
An English translation of an Office Action dated Feb. 16, 2013, which issued during the prosecution of Chinese Patent Application No. 200880126889.0.
A Notice of Allowance dated Aug. 2, 2012, which issued during the prosecution of U.S. Appl. No. 12/529,936.
An International Preliminary Report on Patentability dated Jan. 10, 2012, which issued during the prosecution of Applicant's PCT/IL2010/000549.
An International Preliminary Report on Patentability dated Jan. 17, 2012, which issued during the prosecution of Applicant's PCT/IL2010/000564.
An International Preliminary Report on Patentability dated Jun. 5, 2012, which issued during the prosecution of Applicant's PCT/IL2010/000999.
An International Preliminary Report on Patentability dated Jun. 5, 2012, which issued during the prosecution of Applicant's PCT/IL2010/001018.
An International Preliminary Report on Patentability dated Jun. 10, 2014, which issued during the prosecution of Applicant's PCT/IL2012/050506.
A Notice of Allowance issued in U.S. Appl. No. 13/807,906 dated Oct. 10, 2014.
A Restriction Requirement dated Jan. 29, 2014, which issued during the prosecution of U.S. Appl. No. 13/519,971.
An International Preliminary Report on Patentability dated Jun. 12, 2012, which issued during the prosecution of Applicant's PCT/IL2010/001037.
An International Preliminary Report on Patentability dated Mar. 4, 2014, which issued during the prosecution of Applicant's PCT/IL2012/000300.
An International Preliminary Report on Patentability dated May 6, 2014, which issued during the prosecution of Applicant's PCT/IL2012/050424.
An International Preliminary Report on Patentability dated May 8, 2012, which issued during the prosecution of Applicant's PCT/IL2010/000917.
An International Preliminary Report on Patentability dated Nov. 18, 2014, which issued during the prosecution of Applicant's PCT/IL2012/000190.
International Preliminary Report on Patentability dated Aug. 21, 2013 in corresponding International Application No. PCT/IL2012/000083.
An International Search Report dated Nov. 28, 2014, which issued during the prosecution of Applicant's PCT/IL2014/050434.
An Interview Summary dated Feb. 28, 2012, which issued during the prosecution of U.S. Appl. No. 12/529,936.
An Office Action dated Jul. 28, 2014, which issued during the prosecution of U.S. Appl. No. 13/031,871.
U.S. Appl. No. 61/678,182, filed Aug. 1, 2012.
U.S. Appl. No. 61/529,931, filed Sep. 1, 2011.
An Office Action dated Nov. 3, 2014, which issued during the prosecution of Canadian Patent Application No. 2767596.
Notice of Allowance dated Jun. 18, 2013, which issued during the prosecution of U.S. Appl. No. 13/523,296.
Office Action dated Oct. 27, 2014 in Canadian Patent Application No. 2,785,953.
An Office Action dated Nov. 19, 2013, which issued during the prosecution of U.S. Appl. No. 13/663,117.
U.S. Appl. No. 61/553,209, filed Oct. 30, 2011.
U.S. Appl. No. 61/499,195, filed Jun. 21, 2011.
U.S. Appl. No. 61/749,965, filed Jan. 8, 2013.
U.S. Appl. No. 61/505,132, filed Jul. 7, 2011.
U.S. Appl. No. 61/496,613, filed Jun. 14, 2011.
U.S. Appl. No. 61/221,074, filed Jun. 28, 2009.
U.S. Appl. No. 61/219,758, filed Jun. 23, 2009.

\* cited by examiner

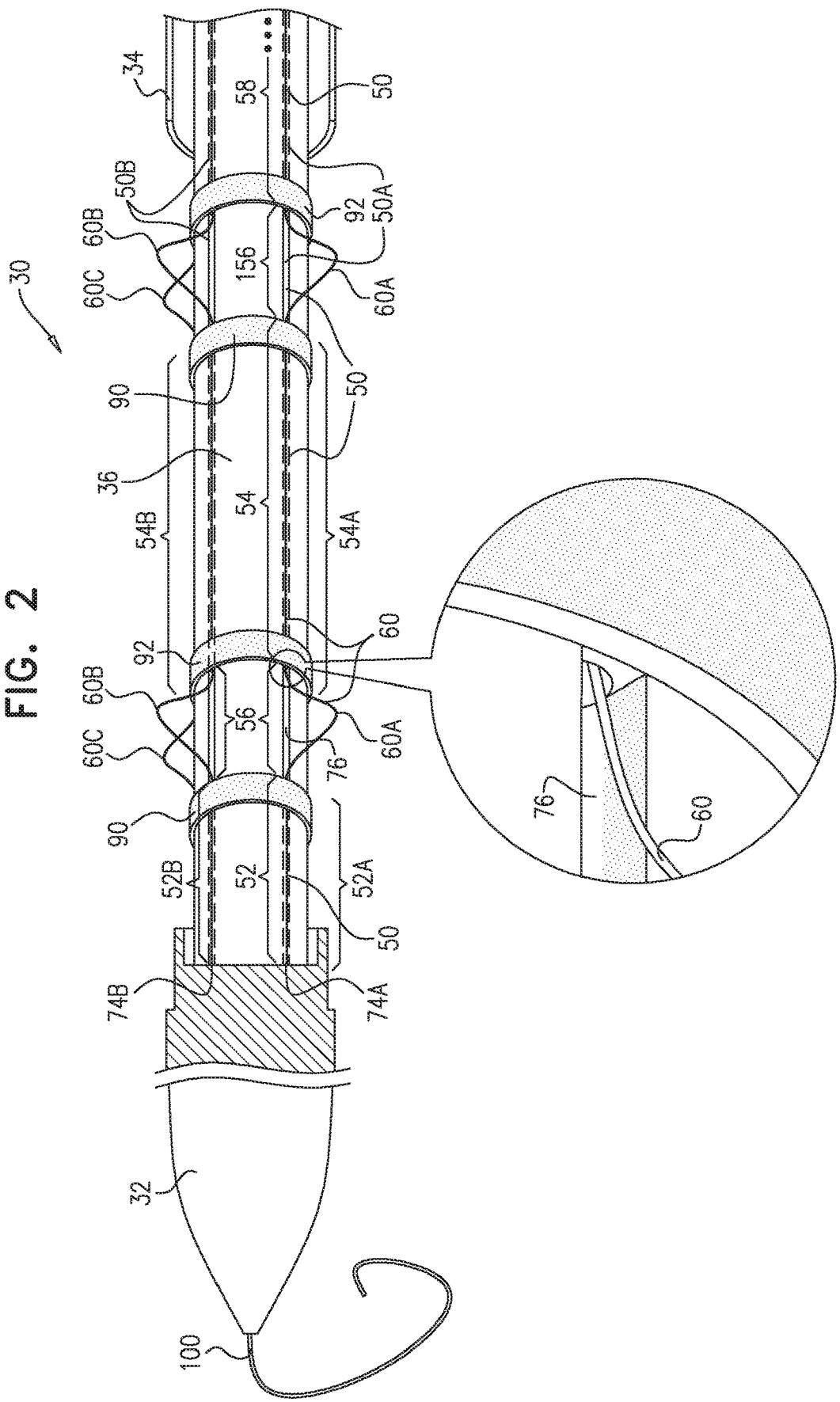

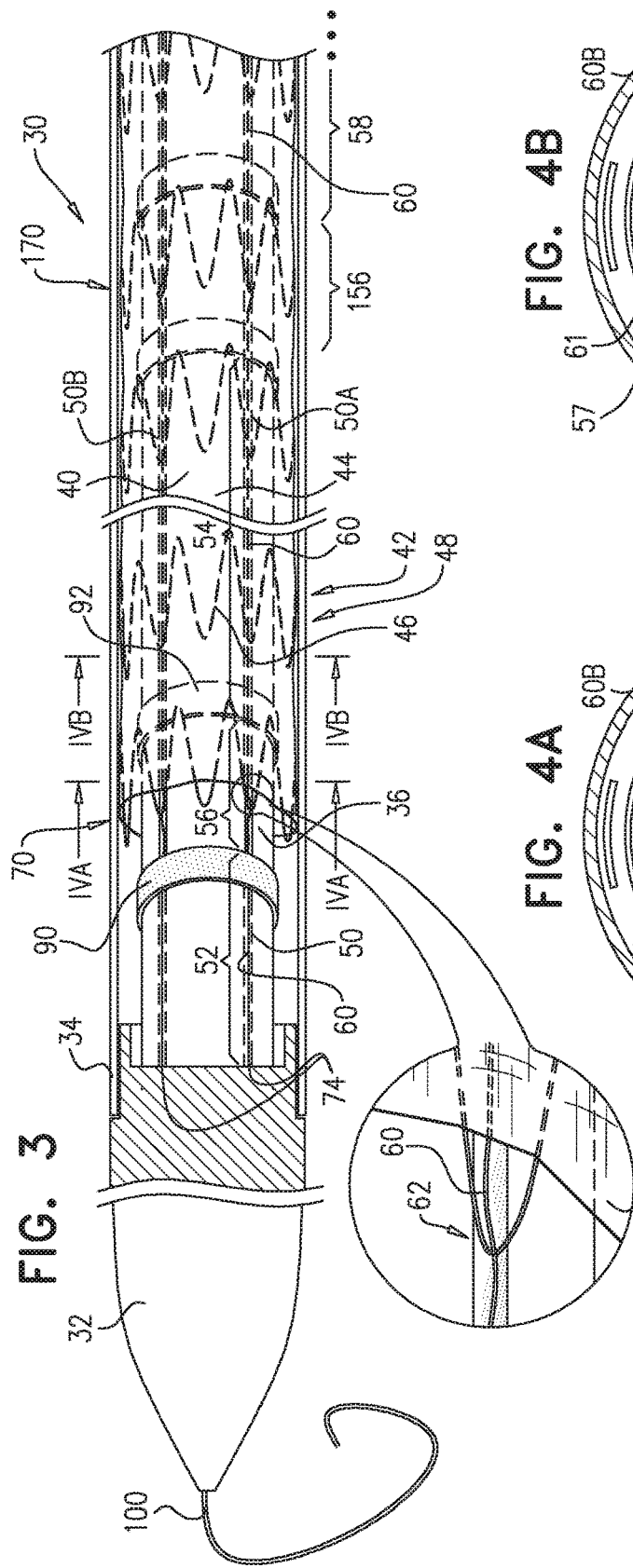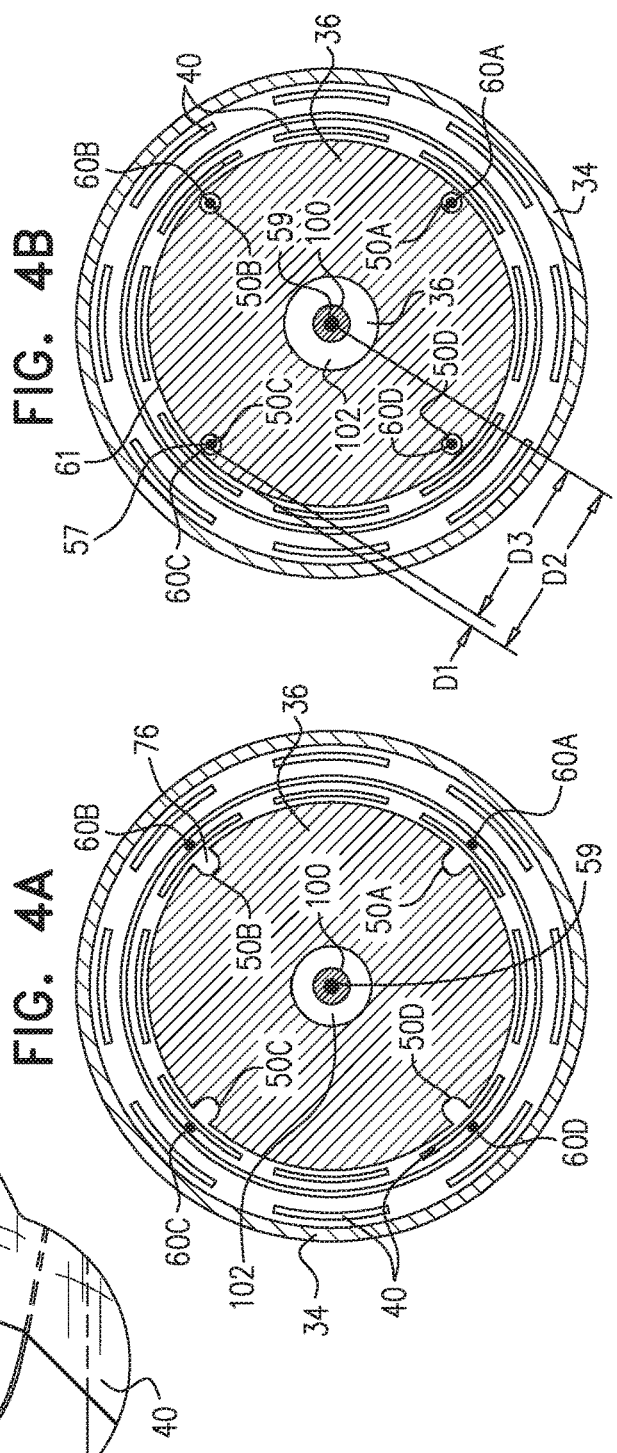

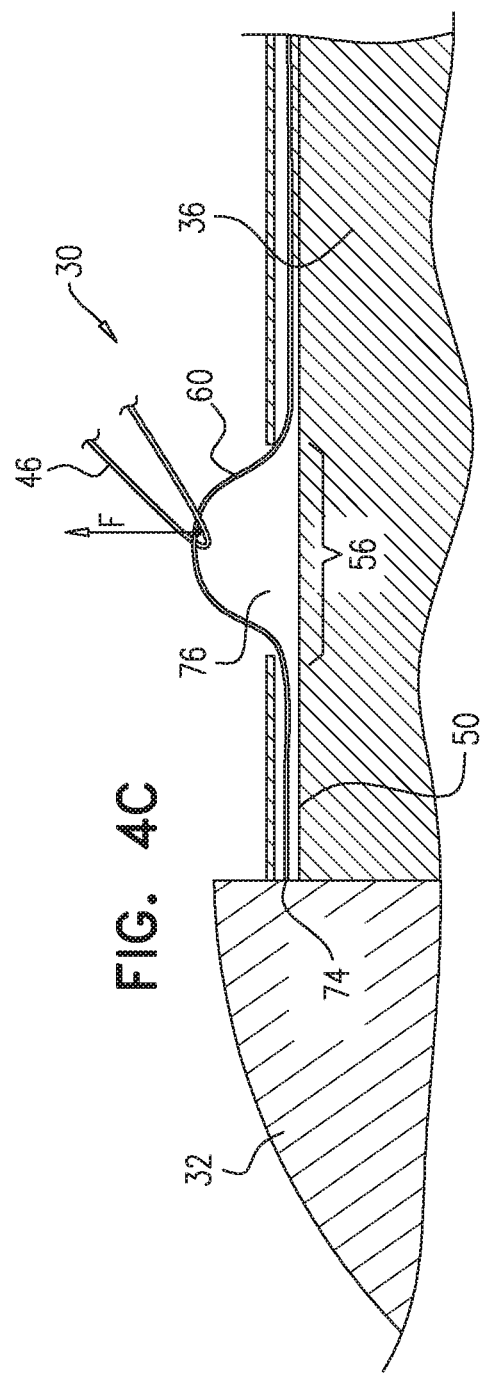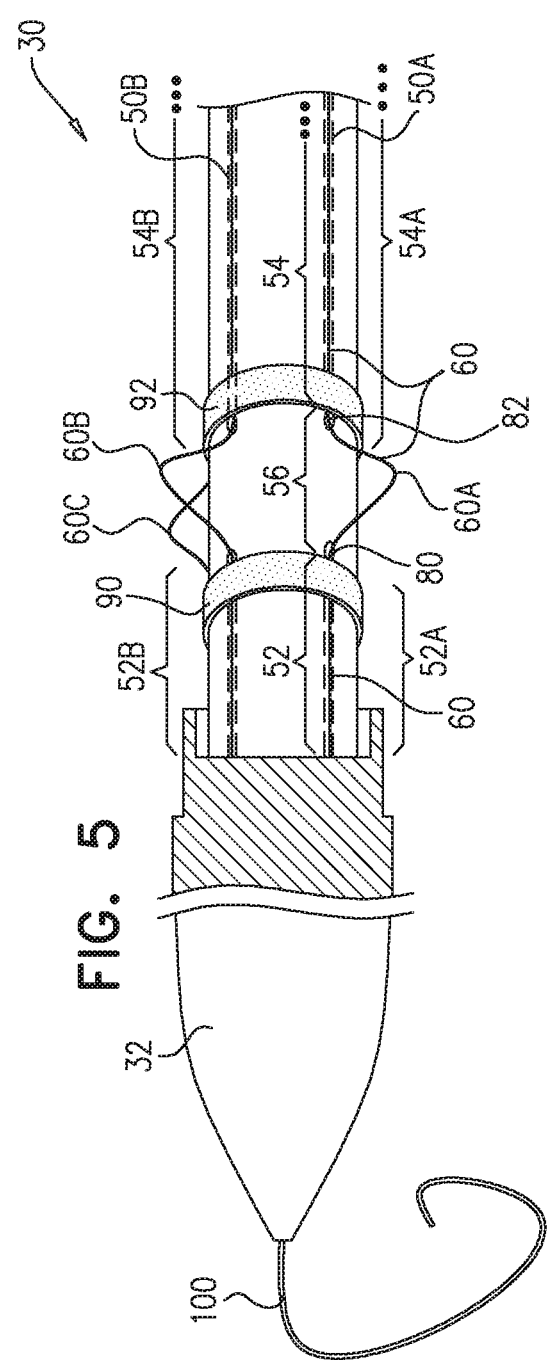

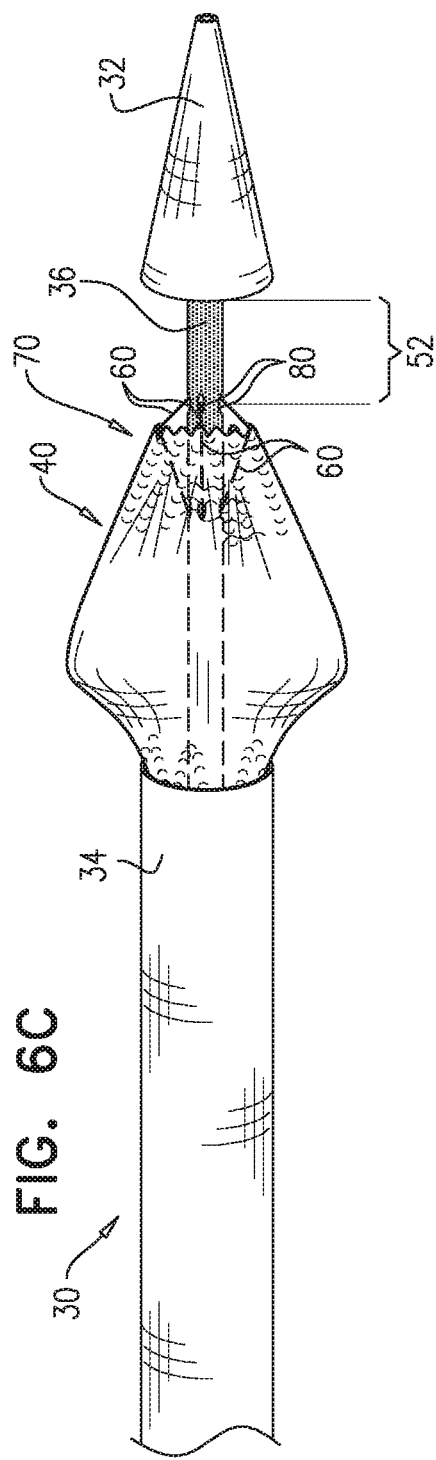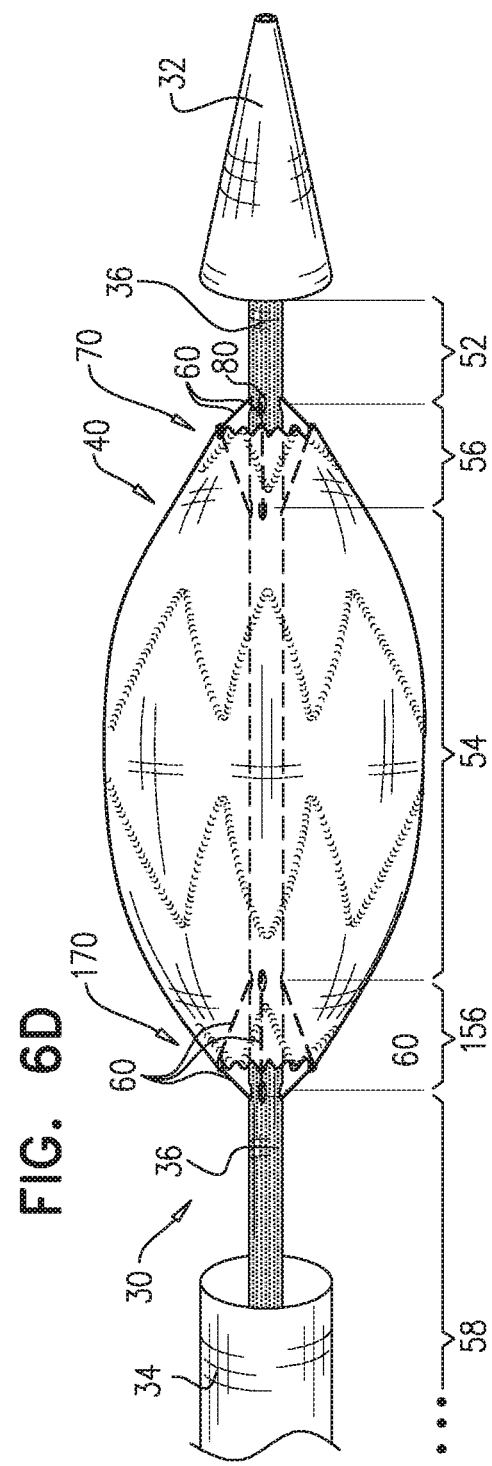

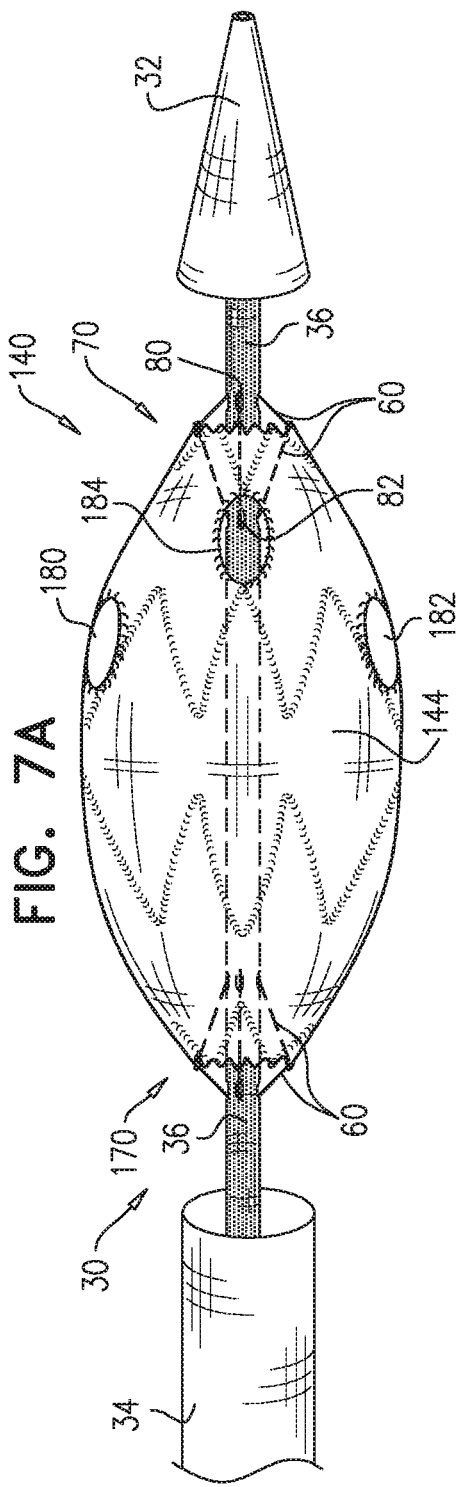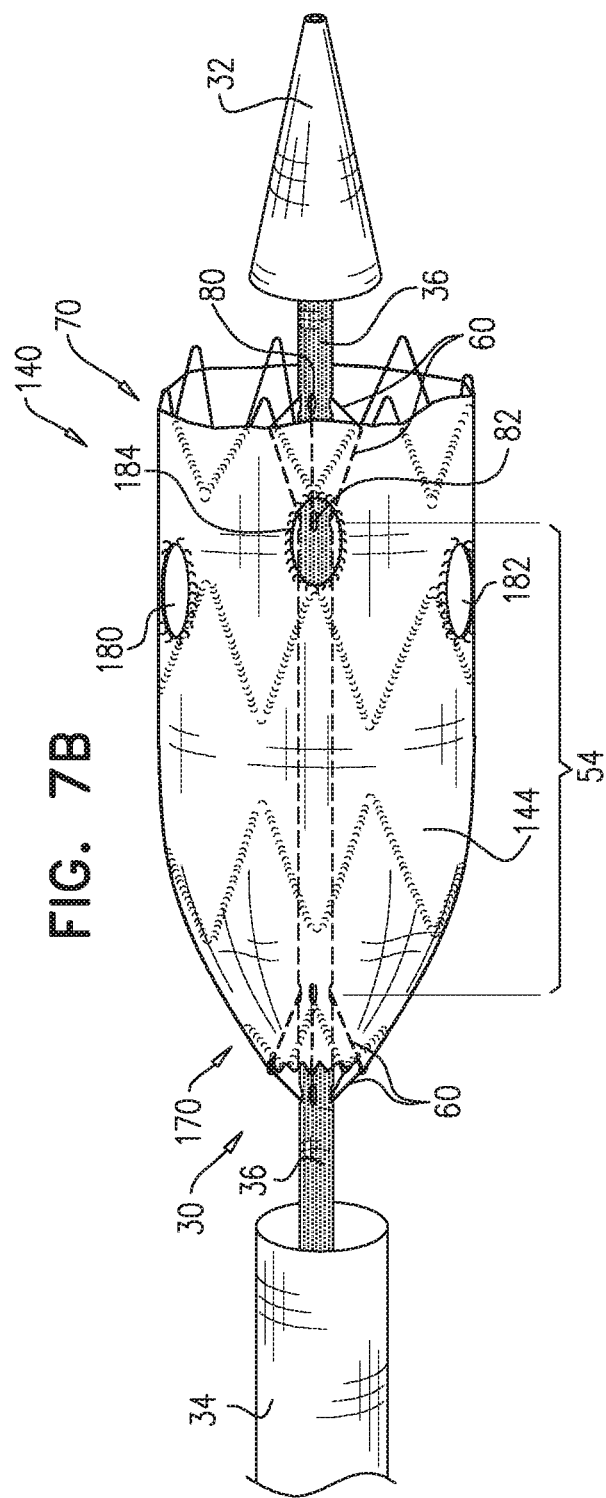

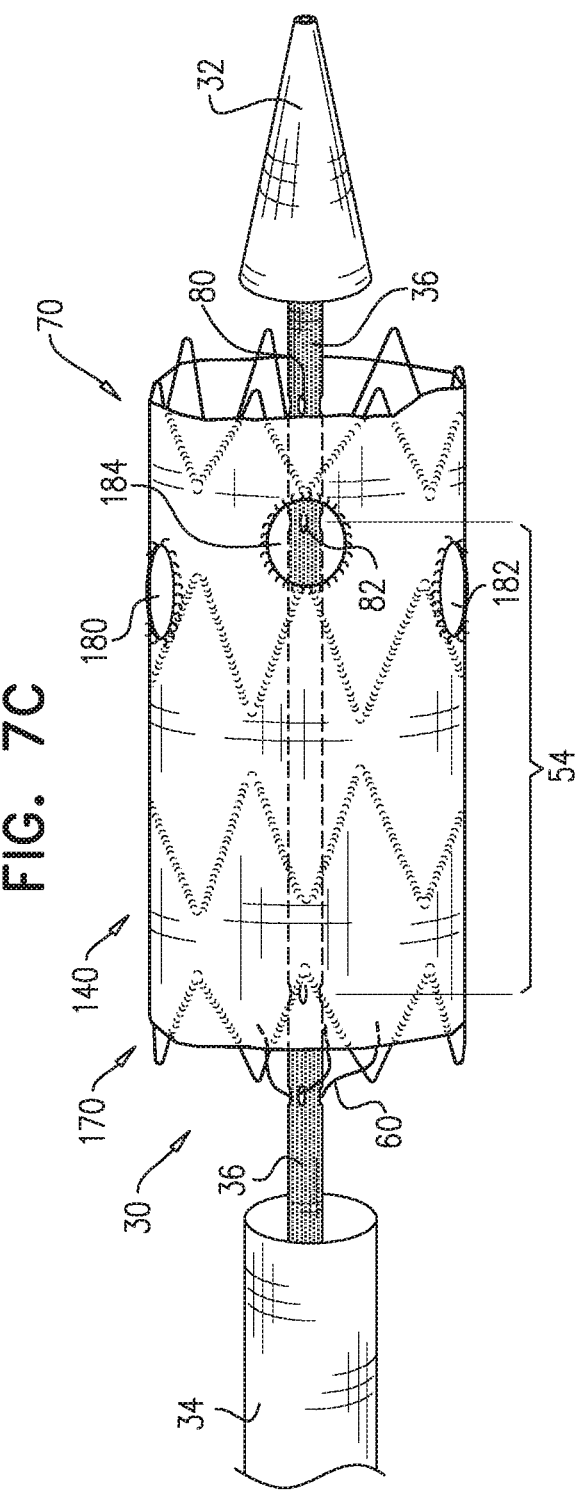

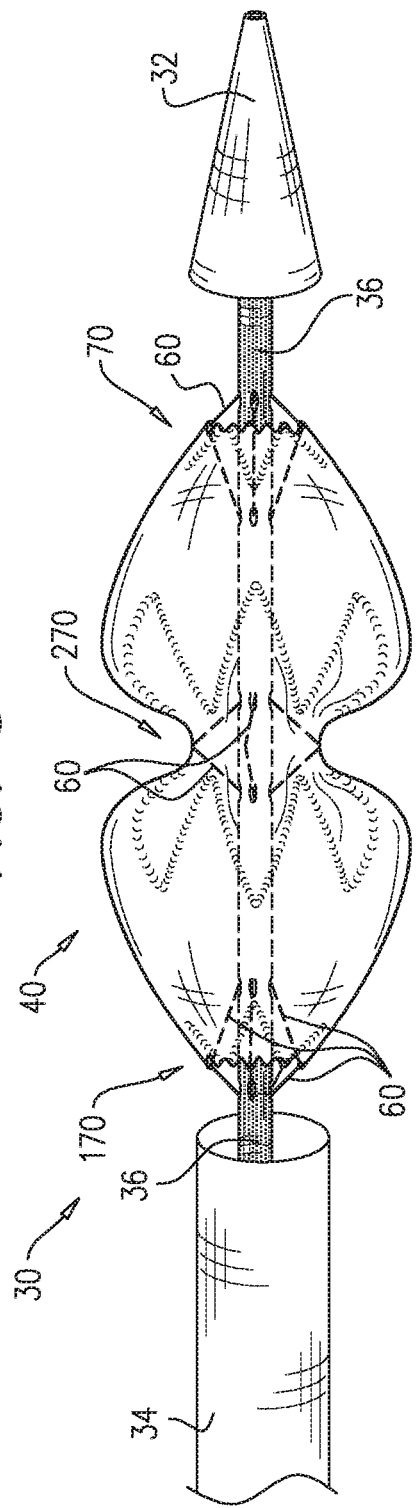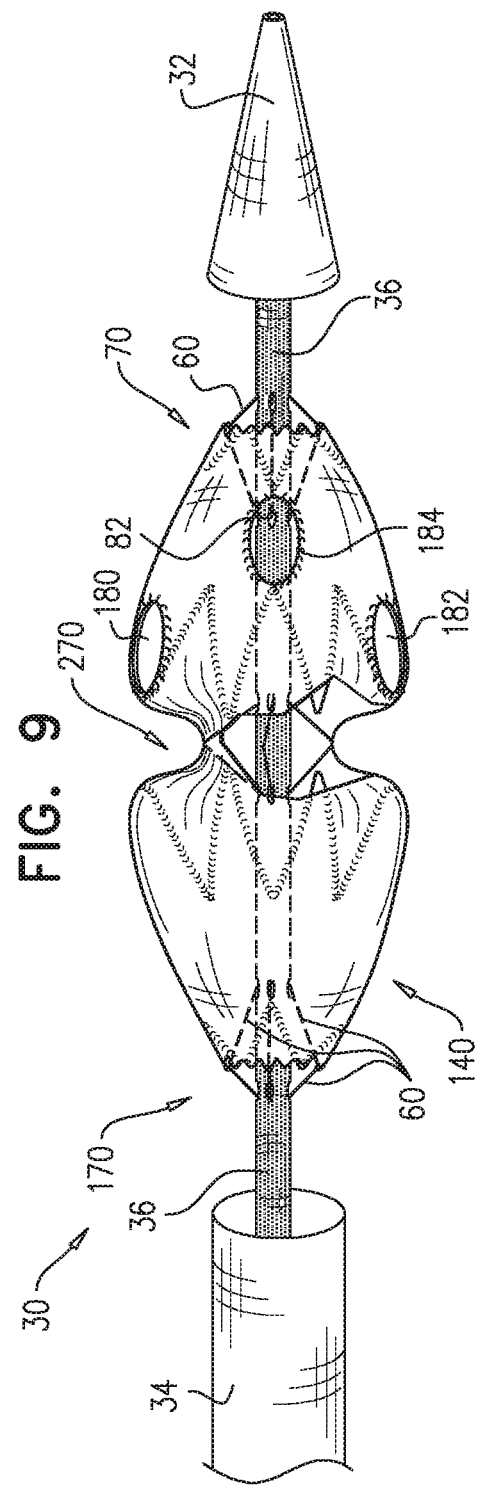

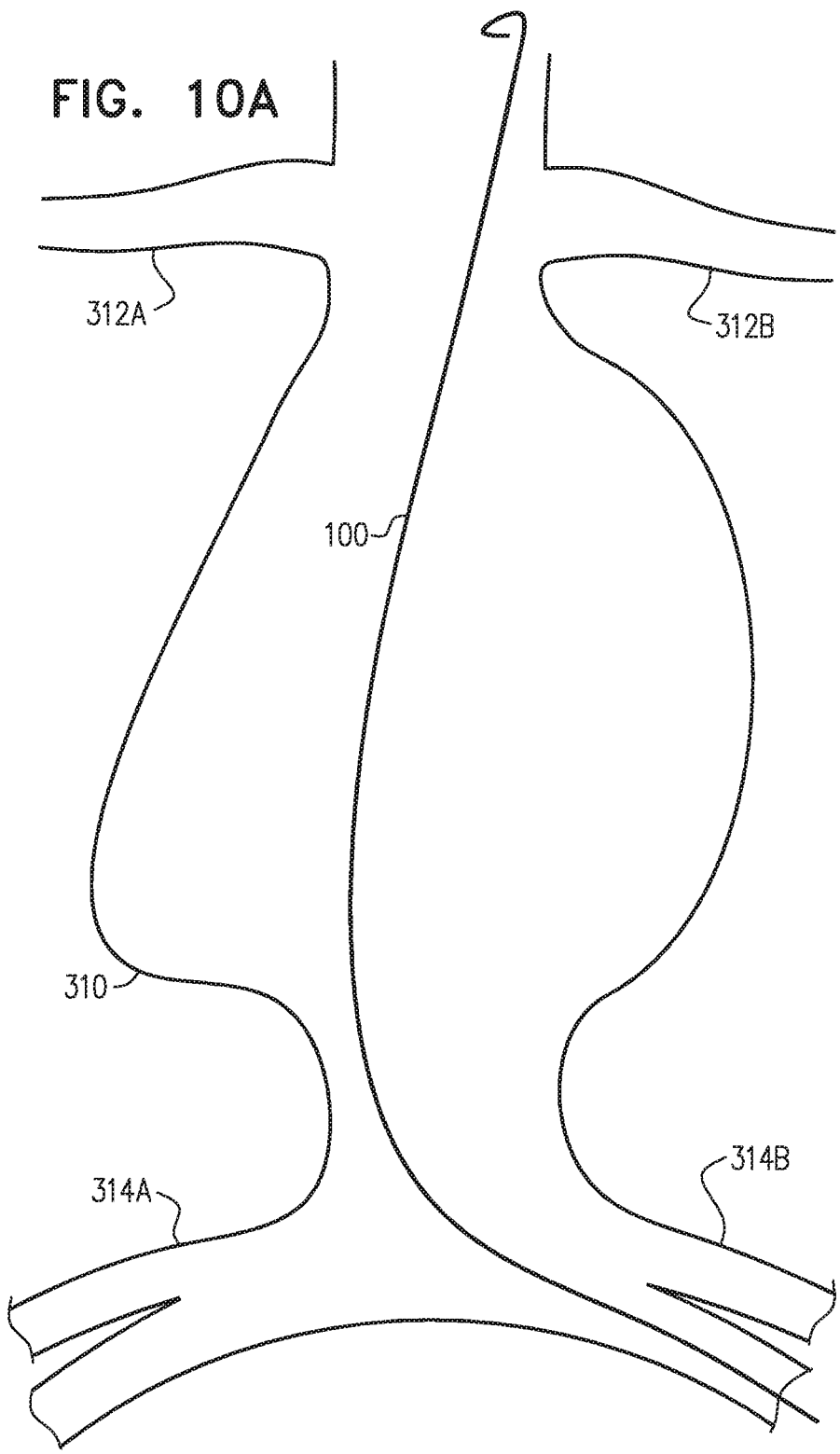

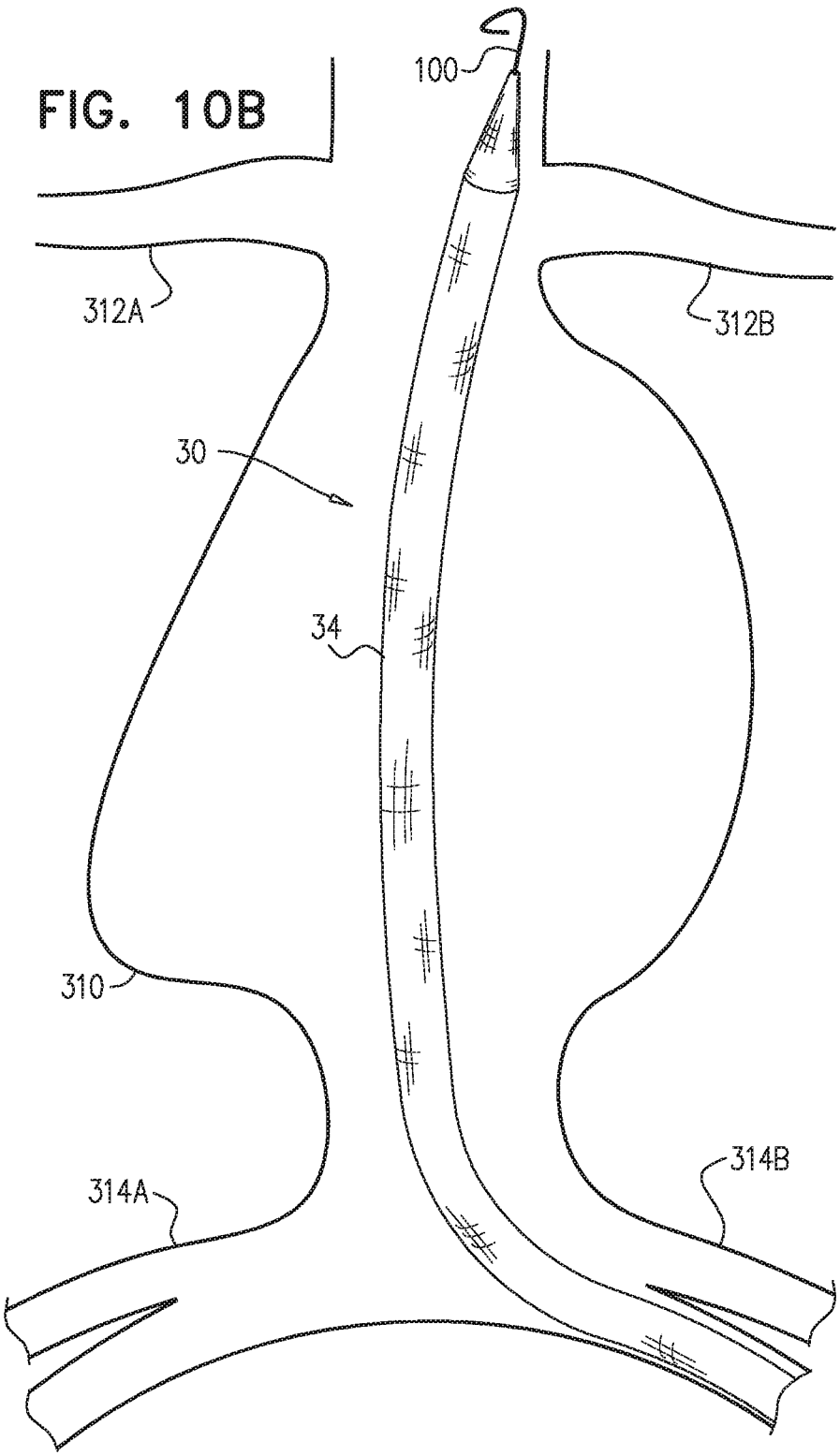

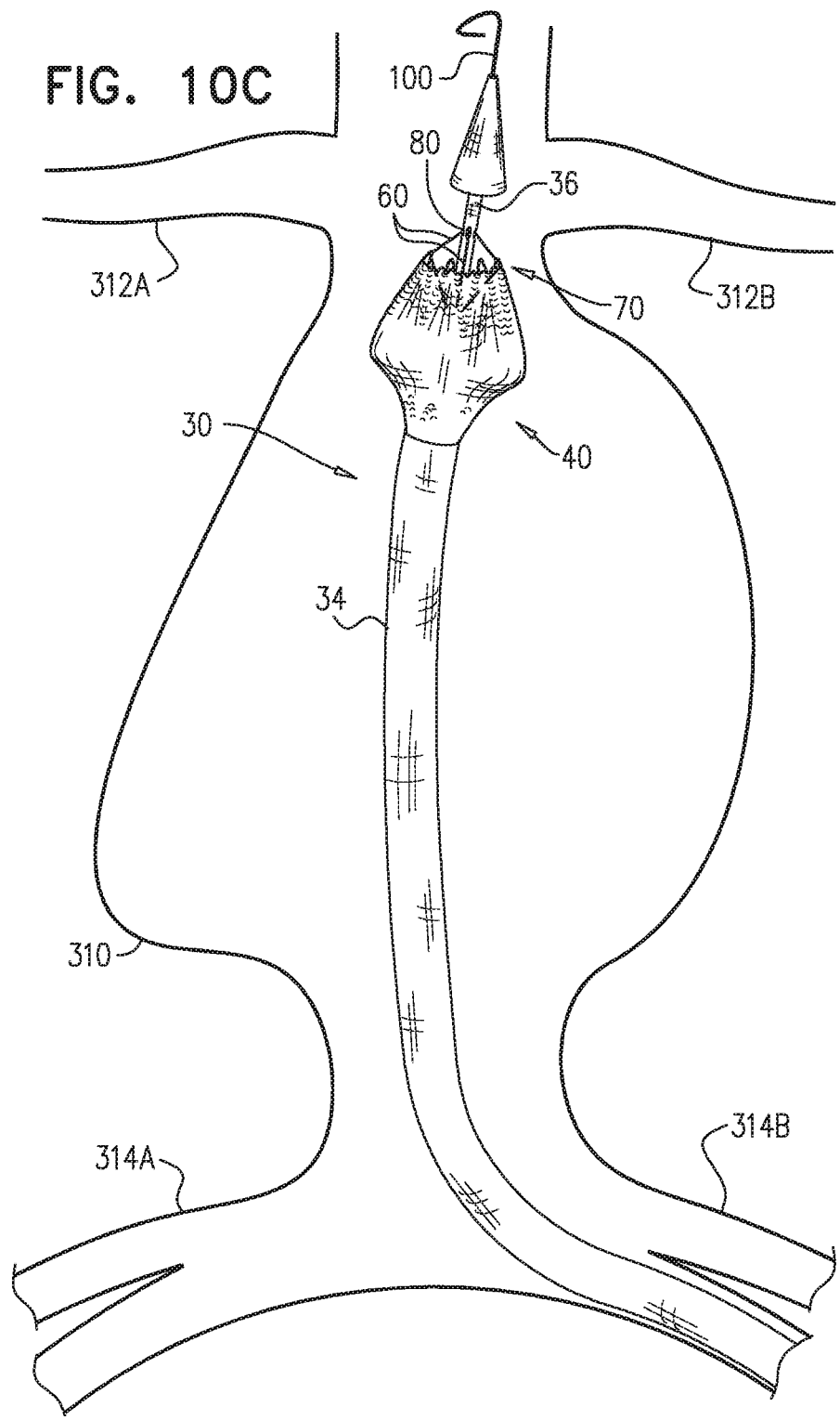

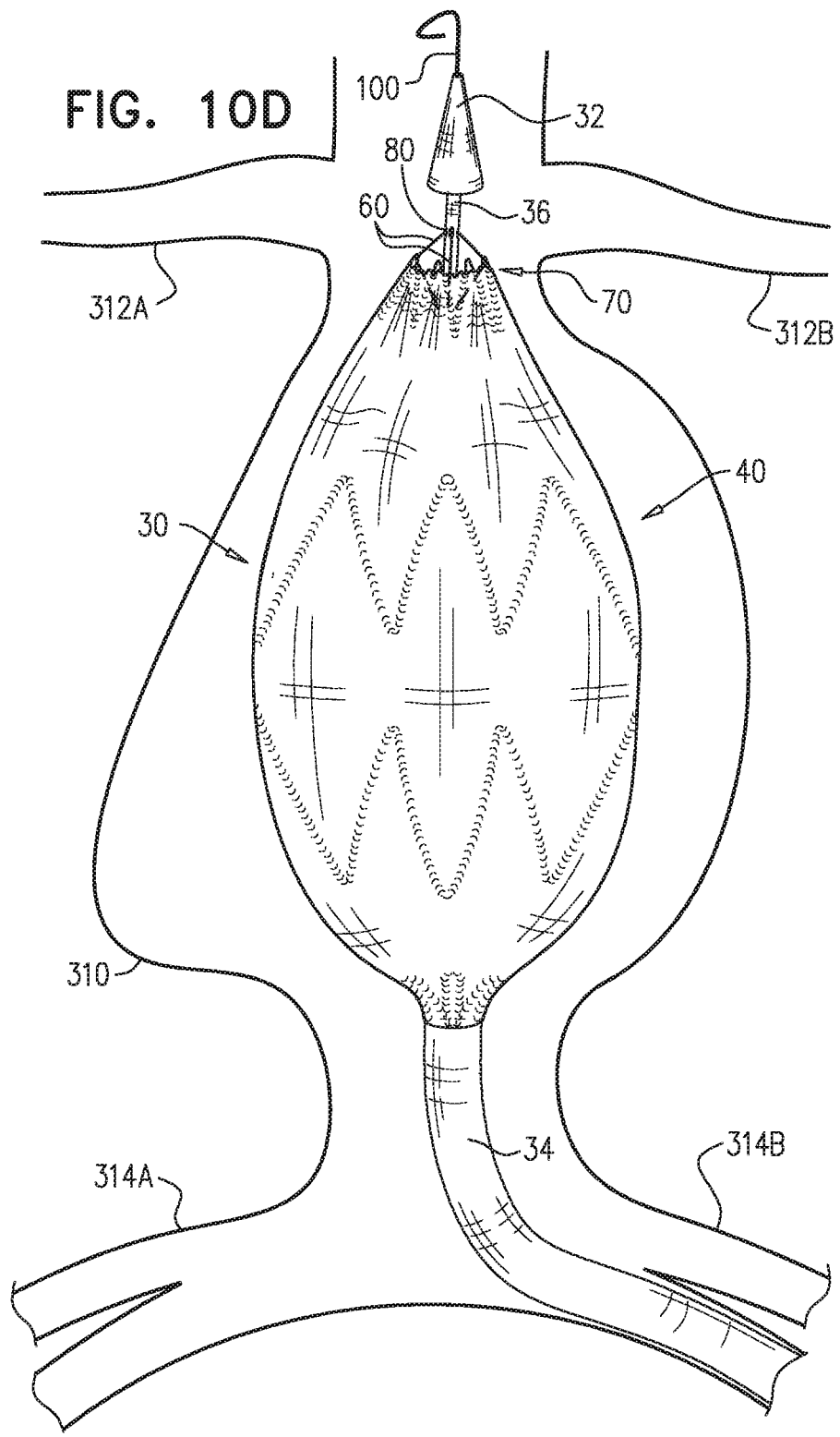

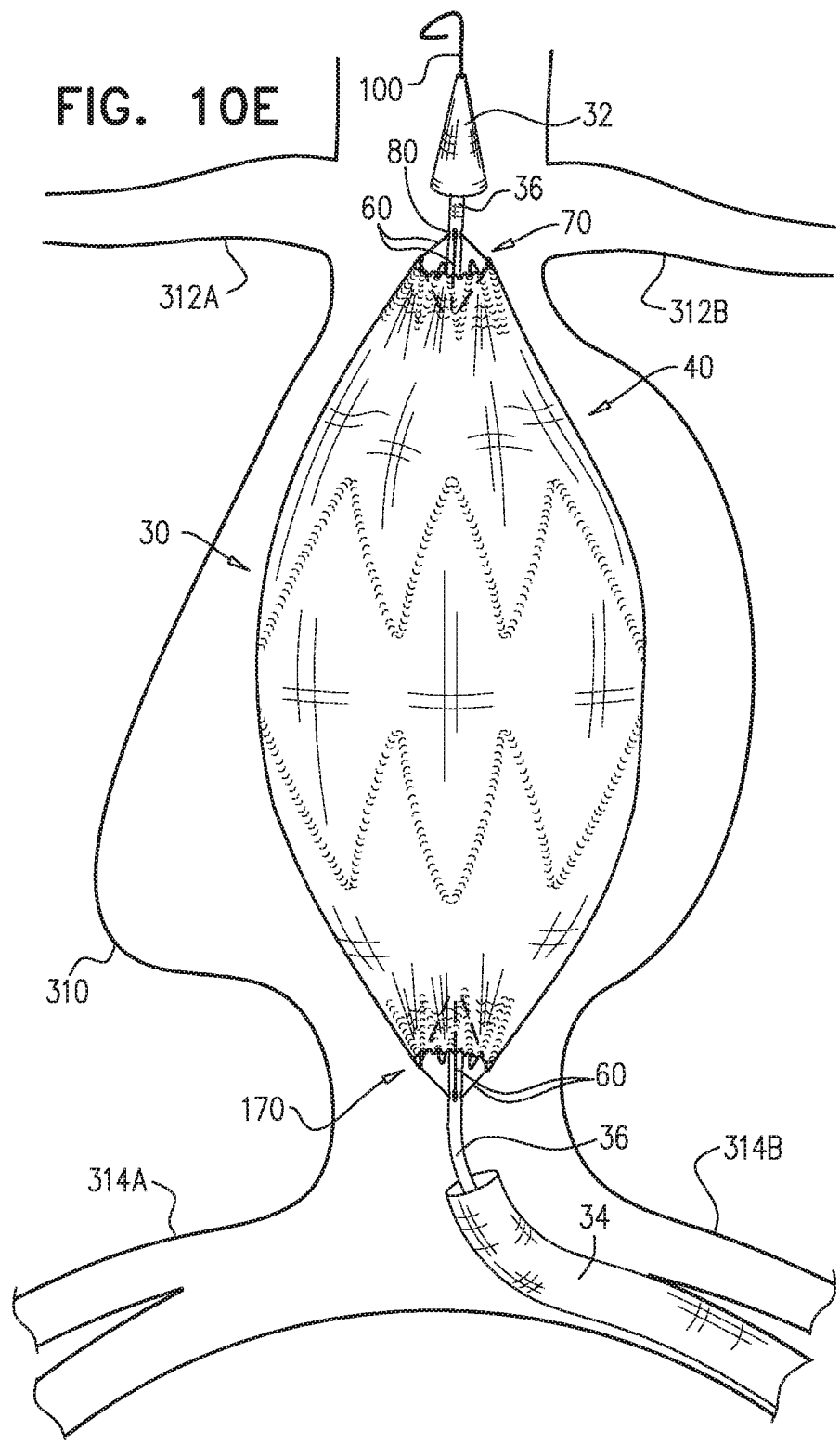

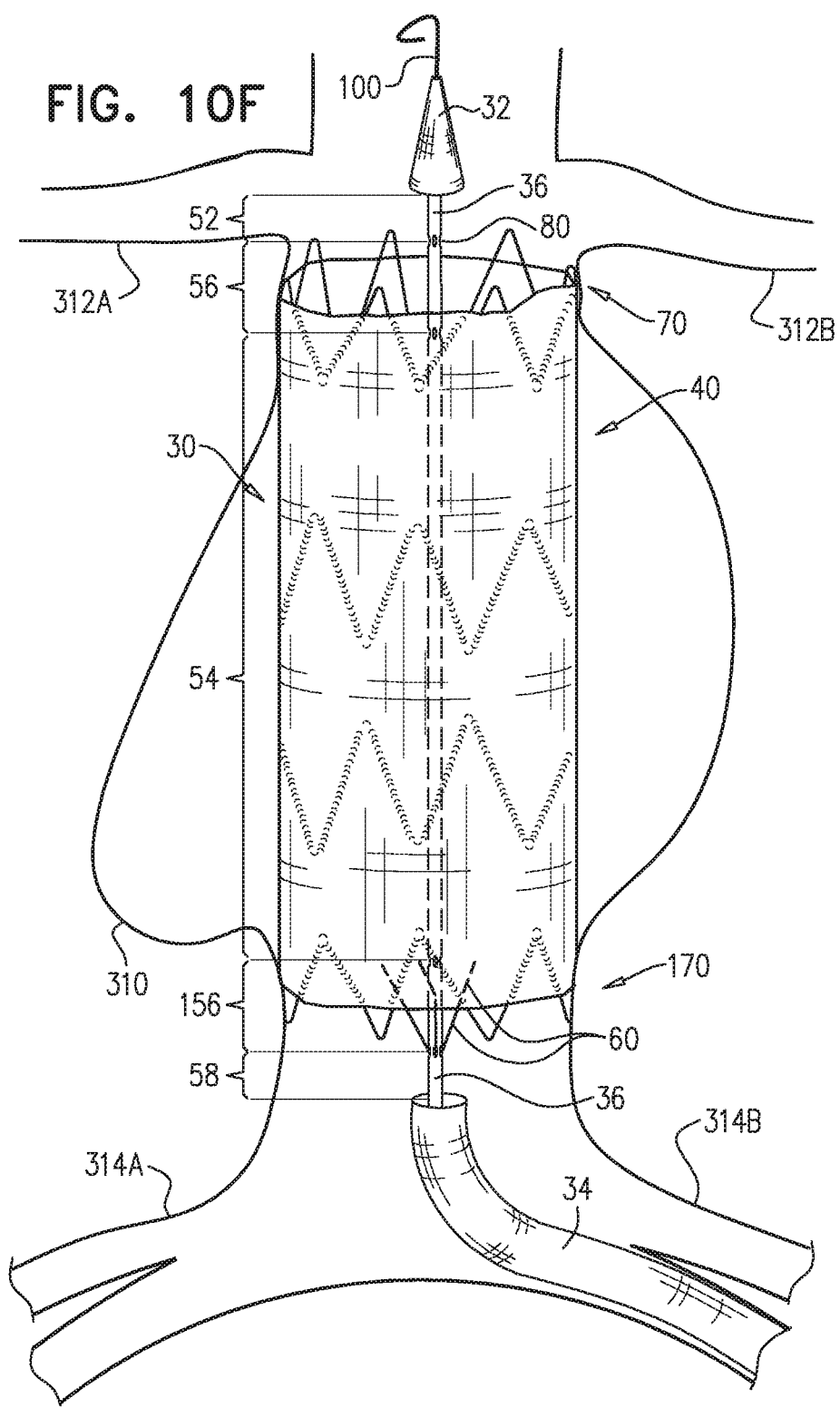

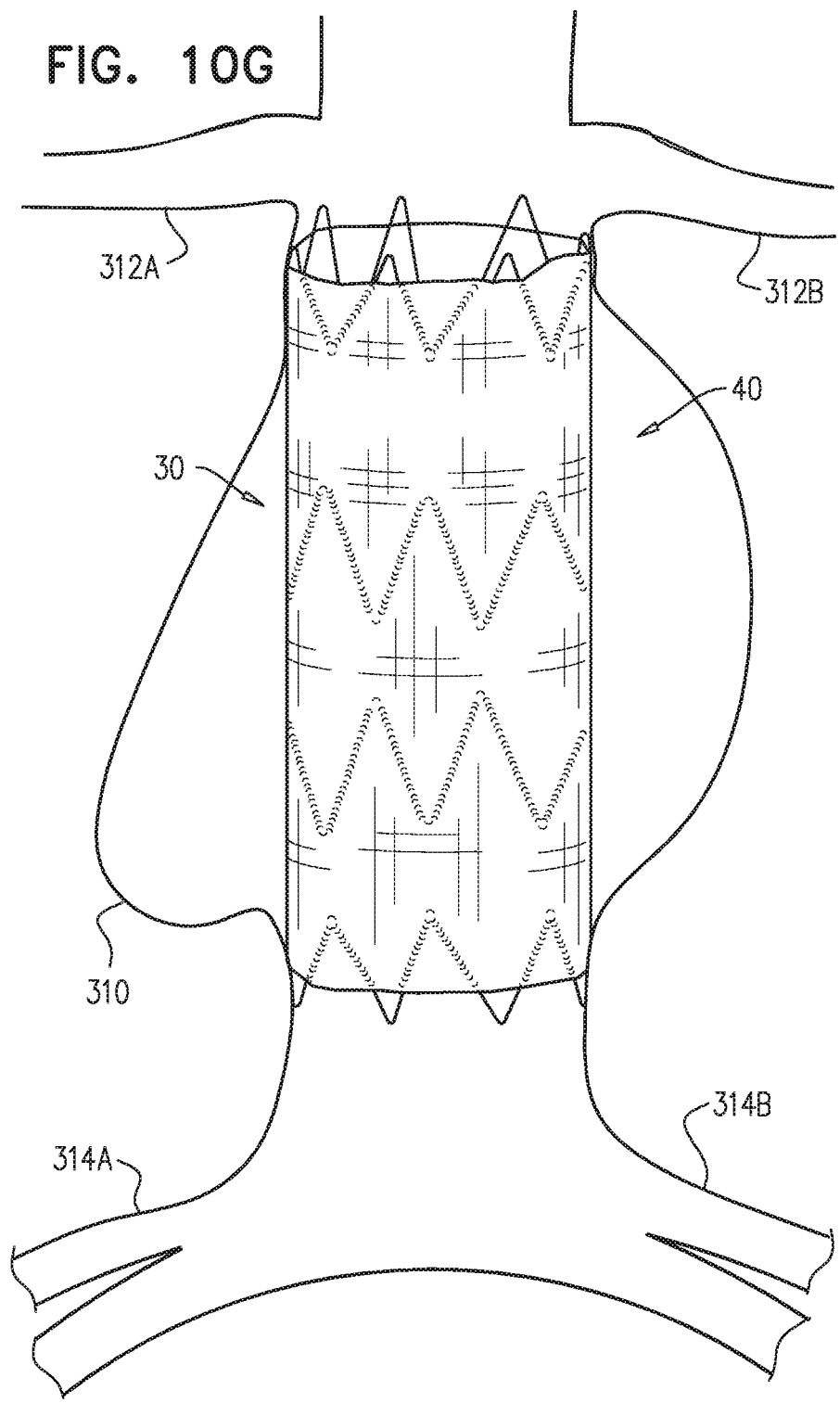

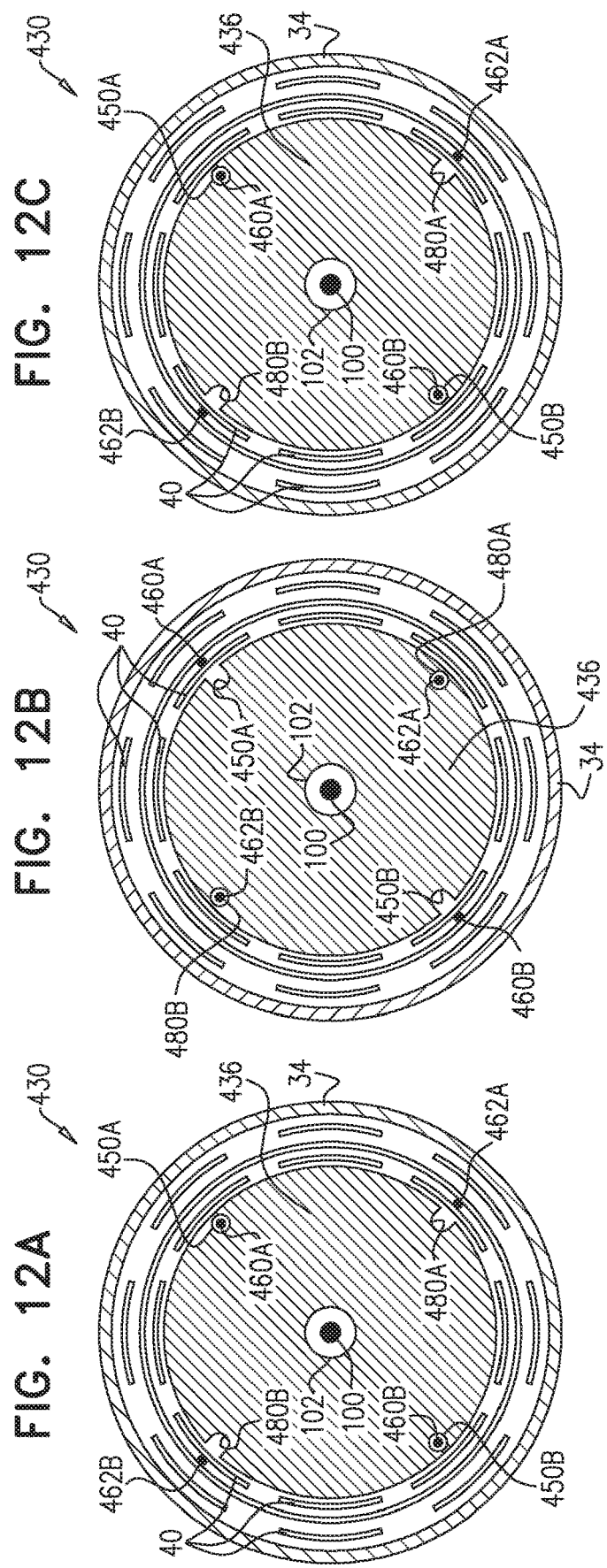

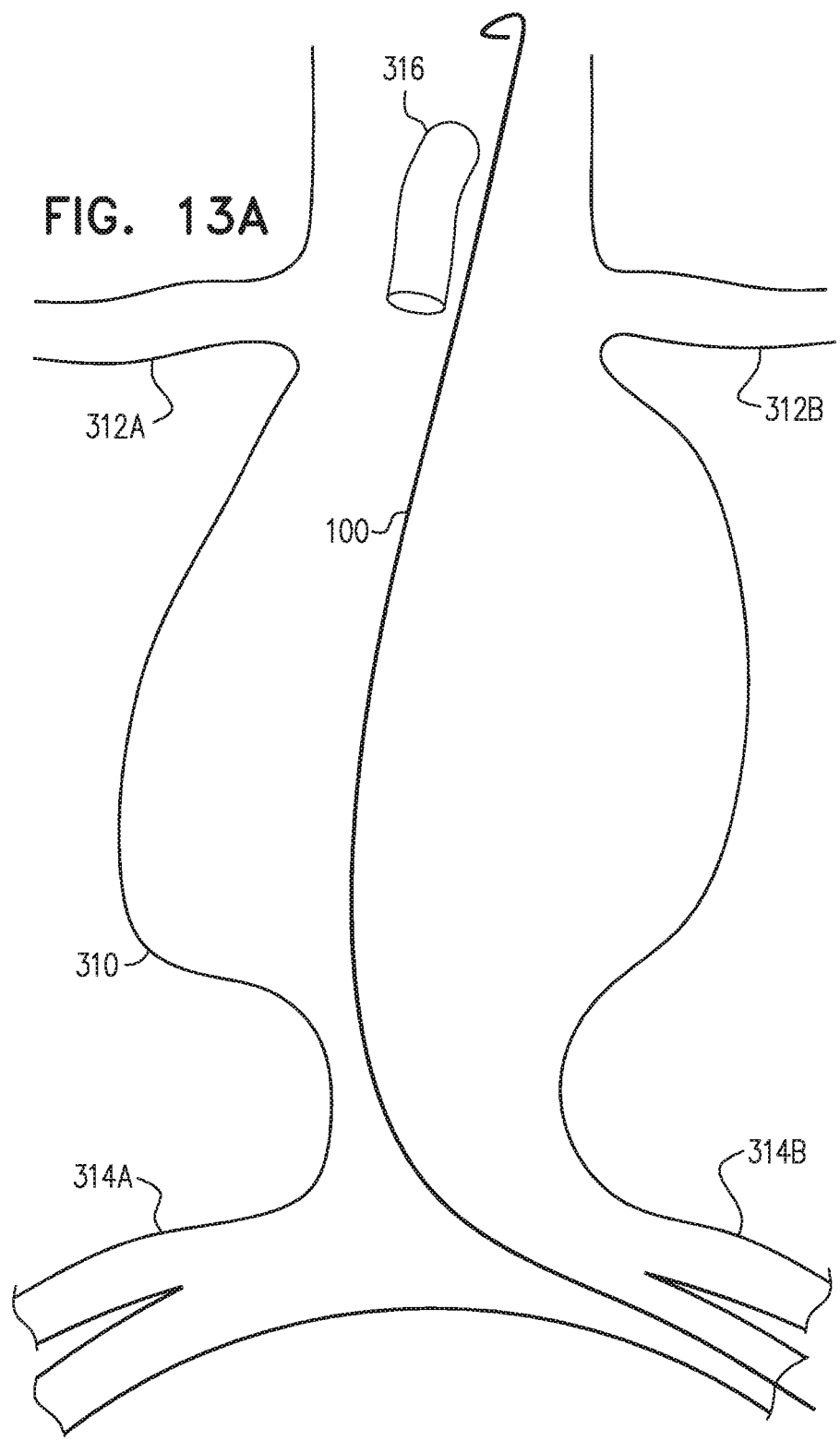

STENT SYSTEM WITH RADIAL-EXPANSION LOCKING

CROSS-REFERENCE TO RELATED APPLICATIONS

The present application is the U.S. national stage of International Application PCT/IL2014/050973, filed Nov. 6, 2014, which claims priority from (a) U.S. Provisional Application 61/906,014, filed Nov. 19, 2013, and (b) U.S. Provisional Application 61/926,533, filed Jan. 13, 2014, both of which applications are assigned to the assignee of the present application and are incorporated herein by reference.

FIELD OF THE APPLICATION

The present invention relates generally to implantable medical devices, and specifically to delivery tools and implantable stent-grafts.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms. A TAA may occur downstream the aortic arch, i.e., in the descending aorta. Alternatively, a TAA may occur in the aortic arch itself, where the aorta branches to supply the brachiocephalic, left carotid and subclavian arteries, or may occur in the ascending aorta.

Endo-Vascular Aneurysm Repair (EVAR) has transformed the practice of treatment of aortic aneurysms from an open surgical approach to a much less invasive surgical approach. The first step of an endovascular intervention usually requires introducing a delivery system into the vasculature of a subject. If the crossing profile, i.e., the external diameter, of the delivery system is 24 Fr or lower (3 Fr=1 millimeter), a true percutaneous approach may be used, because vascular closure devices are available for proper closure of such puncture sites.

Blood vessels occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally-invasive surgical procedures. An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

Aortic dissection is a tear or partial tear in the inner wall of the aorta, which causes blood to flow between the layers of the wall of the aorta, forcing the layers apart. Aortic dissections may be divided into two types in accordance with the Stanford classification: Type A dissections involve the ascending aorta and/or aortic arch, and possibly the descending aorta. Type B dissections involve the descending aorta or the arch (distal to right brachiocephalic artery origin), without involvement of the ascending aorta.

US Patent Application Publication 2007/0016281 to Melsheimer describes an introducer apparatus for deploying a self-expandable medical device, such as a stent, to a target area of a body vessel of a patient. The introducer apparatus comprises a shaft having a proximal end and a distal end, and a distal end portion disposed at the shaft distal end. The distal end portion comprises an introducer body and at least one deployment member. The introducer body is sized and shaped relative to the self-expandable medical device such that the medical device is receivable on a surface of the introducer body when the medical device is in a compressed condition. The deployment member is configured and arranged relative to the introducer body for selectively restraining the self-expandable medical device in the compressed condition on the introducer apparatus surface.

US Patent Application Publication 2013/0131783 to Shalev et al. describes medical apparatus for insertion into a mammalian body. The apparatus includes structural stent elements, at least a portion of which are shaped so as to define (a) at least one generally circumferential band, and (b) a plurality of engagement members that are joined to and extend radially inwardly from the band. The apparatus further includes an elongated latch member which is threaded through the engagement members, thereby physically latching the engagement members. The band and the engagement members are configured such that (a) when the latch member is threaded through and thus physically latches the engagement members, the engagement members retain the band in a radially-compressed state, and (b) when the latch member is removed from the engagement members, the band assumes a radially-expanded state. Other embodiments are also described.

US Patent Application Publication 2006/0190070 to Dieck et al. describes devices, systems and methods for stenting body lumens. In particular, stents are described which are advanceable directly over a guidewire and expandable within a target location of a body lumen by retraction of the guidewire and/or by releasing constraining element(s) disposed around at least a portion of the stent. Typically the constraining element(s) have the form of one or more bands or layers of material which hold the stent in an unexpanded configuration. These stent designs allow delivery to a body lumen without the need for a number of additional devices which are typically used in the delivery of conventional stents, thereby reducing the profile of the stent during delivery, increasing the flexibility of the stent during delivery to allow passage through more tortuous pathways, and allowing the delivery of branched or otherwise connected stents to body lumens, such as branched lumens.

SUMMARY OF THE APPLICATION

Some applications of the present invention provide a stent-graft deployment system, which is configured to deliver and deploy a stent-graft to a lumen of a body, such as a blood vessel, e.g., an artery. For some applications, the stent-graft deployment system is used to treat an artery affected by an aneurysm and/or a dissection. The deployment system comprises at least one restraining wire, and an elongated delivery shaft, which comprises an inner shaft. The inner shaft is removably disposed in the stent-graft, which in turn is radially constrained by an outer sheath of the deployment system. The deployment system is configured such that the at least one restraining wire prevents full radial expansion of one or more longitudinal portions of the stent-graft after the outer sheath has been withdrawn from the stent-graft.

The inner shaft is shaped so as to define at least one conduit therealong, which is typically not coaxial with the inner shaft. The conduit is shaped so as to define at least first and second non-longitudinally-overlapping enclosed longitudinal segments. The conduit is also shaped so as to define a restraining longitudinal portion that is longitudinally disposed between the first and the second enclosed longitudinal segments. The deployment system is configured such that:

when the restraining wire is removably disposed in the first and the second enclosed longitudinal segments, a portion of the restraining wire disposed alongside the restraining longitudinal portion of the inner shaft prevents full radial expansion of a longitudinal portion of the stent-graft by physically engaging the longitudinal portion of the stent-graft, and when the restraining wire has been withdrawn from at least the first enclosed longitudinal segment, the restraining wire does not prevent the full radial expansion of the longitudinal portion of the stent-graft.

Typically, a proximal portion of the restraining wire is coupled to a withdrawal actuator of a control handle, such as described hereinbelow. A distal end of the restraining wire is not fixed to the delivery shaft, and is free to be proximally withdrawn from the first enclosed longitudinal segment, and thus to free the longitudinal portion of the stent-graft.

As used in the present application, including in the claims, two elements "at least partially longitudinally overlap" if at least a portion of the first element is disposed at a same longitudinal position as at least a portion of the second element, and two elements do "not longitudinally overlap" or are "non-longitudinally-overlapping" if no portion of the first element is disposed at a same longitudinal position as any portion of the second element.

Upon withdrawal of the outer sheath, the radially-compressed self-expanding stent-graft's outwardly-directed radial force, at certain locations along and around the stent-graft, is now to the restraining wire. The exposed portion of the restraining wire is short enough relative to its cross section, and hence is stiff enough, so as to act more like a restraining beam than a suturing filament. Therefore, the outwardly-directed radial force does not pull out the portion of the restraining wire disposed in the first, more distal enclosed longitudinal segment, even though the distal end of the restraining wire is not fixed to the delivery shaft. The relatively small inner diameter of the first and the second enclosed longitudinal segments also generally helps prevent the restraining wire from being prematurely pulled out of the first enclosed longitudinal segment. The relatively short length of the restraining longitudinal portion enables the restraining wire to perform its restraining function, even though the restraining wire is still flexible enough to accommodate a tortuous path through the subject's vasculature during advancing of the delivery shaft. In other words, if the restraining longitudinal portion were longer, the restraining wire would need to be so stiff that the restraining wire could not accommodate the tortuous path of the vasculature.

The flexibility of the restraining wire allows the portion of the restraining wire to extend outward from the inner shaft, when the restraining wire is disposed in the first and the second enclosed longitudinal segments. This outward extension allows the restraining wire to physically engage the longitudinal portion of the stent-graft, without any elements of the stent-graft projecting into the interior of the inner shaft. As a result, the inner shaft may be provided with a relatively small diameter, such as no more than 4 mm, which enables the delivery shaft to have a small crossing profile when loaded with the stent-graft.

For some applications, the conduit is open along the restraining longitudinal portion of the inner shaft. For example, the inner shaft may be shaped so as to define a longitudinal slit along the restraining longitudinal portion. For some applications, the conduit is shaped so as to define (a) a first opening at a first longitudinal border between the first enclosed longitudinal segment and the restraining longitudinal portion of the inner shaft, and (b) a second opening at a second longitudinal border between the second enclosed longitudinal segment and the restraining longitudinal portion of the inner shaft. The deployment system is configured such that when the restraining wire is removably disposed in the first and the second enclosed longitudinal segments, the restraining wire passes through the first and the second openings.

For some applications, the deployment system further comprises first and second rings. The first ring is longitudinally fixed to and surrounds the inner shaft at a first longitudinal border between the first enclosed longitudinal segment and the restraining longitudinal portion of the inner shaft, and the second ring is longitudinally fixed to and surrounds the inner shaft at a second longitudinal border between the second enclosed longitudinal segment and the restraining longitudinal portion of the inner shaft. The rings typically prevent the inner shaft from being damaged by the restraining wire, which may be strong and thin. The inner shaft may comprise a polymer, which might be torn by the restraining wire in the absence of the rings. For some applications, the rings comprise a radiopaque metal, such as tantalum. The radiopaque material enables the surgeon to visualize the ends of the restraining longitudinal portion during an implantation procedure, which may aid in the proper positioning of the inner shaft and the stent-graft during the procedure.

For some applications, the inner shaft is shaped so as to define a plurality of conduits therealong. For some applications, the plurality of conduits are circumferentially evenly distributed around the inner shaft. The conduits are shaped so as to define respective first enclosed longitudinal segments and respective second enclosed longitudinal segments. Typically, the first enclosed longitudinal segments longitudinally coincide with one another, and the second enclosed longitudinal segments longitudinally coincide with one another. The deployment system comprises a plurality of restraining wires, which are deployed in respective corresponding first and second longitudinal segments, typically such that a single one of the wires is removably disposed in each of the first longitudinal segments and corresponding second longitudinal segment. Providing a separate conduit for each of the restraining wires generally prevents the wires from becoming entangled with one another, or pulling on one another, particularly when the delivery shaft is advanced along a tortuous path through the subject's vasculature.

For some applications, the deployment system is configured to restrain more than one longitudinal portion of the stent-graft, such as two, three, four, or more longitudinal portions.

In some applications of the present invention, the deployment system comprises:

a first restraining wire, which (a) when removably disposed in physical engagement with a first longitudinal portion of the stent-graft, thereby preventing full radial expansion of the first longitudinal portion, and (b) does not engage a second longitudinal portion of the stent-graft, which second longitudinal portion does not longitudinally overlap the first longitudinal portion; and a second restraining wire, which (a) when removably disposed in physical engagement with the second longitudinal portion of the stent-graft, thereby preventing full radial expansion of the second longitudinal portion, and (b) does not engage the first longitudinal portion of the stent-graft.

In some applications of the present invention, the restraining wires comprise at least first and second restraining wires, which physically engage respective longitudinal portions of the stent-graft, thereby preventing full radial expansion of the longitudinal portions. The control handle comprises a first withdrawal actuator to which a proximal portion of the first restraining wire is coupled, and a second withdrawal actuator to which a proximal portion of the second restraining wire is coupled. The first and second withdrawal actuators are configured to withdraw the first and second restraining wires, respectively, in a proximal direction.

There is therefore provided, in accordance with an application of the present invention, apparatus comprising:

a self-expanding stent-graft; and a deployment system, which includes:

an inner shaft, which is removably disposed in the stent-graft, and which is shaped so as to define (a) at least one conduit therealong, which conduit is (i) not coaxial with the inner shaft, and (ii) shaped so as to define at least first and second enclosed longitudinal segments, each of which has a length of at least 5 mm, and (b) a restraining longitudinal portion that is longitudinally disposed between the first and the second enclosed longitudinal segments; and at least one restraining wire, wherein the deployment system is configured such that:

when the restraining wire is removably disposed in the first and the second enclosed longitudinal segments, a portion of the restraining wire disposed alongside the restraining longitudinal portion of the inner shaft prevents full radial expansion of a longitudinal portion of the stent-graft by physically engaging the longitudinal portion of the stent-graft, and when the restraining wire has been withdrawn from at least the first enclosed longitudinal segment, the restraining wire does not prevent the full radial expansion of the longitudinal portion of the stent-graft.

For some applications, the restraining longitudinal portion of the inner shaft has a length equal to at least 15% of a perimeter of the inner shaft. Alternatively or additionally, for some applications, the length is less than 150% of the perimeter. For some applications, the restraining longitudinal portion of the inner shaft has a length equal to less than 15% of a perimeter of the longitudinal portion of the stent-graft when the stent-graft is unconstrained in a fully radially-expanded state, such as less than 5% of the perimeter.

For some applications, the restraining longitudinal portion of the inner shaft has a length of less than 20 mm, such as less than 10 mm, e.g., less than 5 mm. Alternatively or additionally, for some applications, the restraining longitudinal portion of the inner shaft has a length equal to less than 150% of a perimeter of the inner shaft, such as less than 100% of the perimeter. Alternatively or additionally, for some applications, the inner shaft has an outer diameter of no more than 4 mm, such as no more than 3 mm. Alternatively or additionally, for some applications, the length of at least one of the first and the second enclosed longitudinal segments is at least 30 mm. Alternatively or additionally, for some applications, the restraining wire has a diameter of between 0.08 and 0.3 mm.

For some applications, the restraining wire has at least one property selected from the group consisting of: a stiffness of at least 0.0002 $Mm^4$, and a Young's modulus of at least 60 GPa.

For some applications, the first enclosed longitudinal segment is distal to the second enclosed longitudinal segment, the restraining wire terminates at a free distal end thereof, and the deployment system is configured such that, when the restraining wire is removably disposed in the first and the second enclosed longitudinal segments, the free distal end of the restraining wire is disposed at a location selected from the group consisting of: a location within the first enclosed longitudinal segment, and a location distally beyond the first enclosed longitudinal segment.

For some applications, the stent-graft includes a generally tubular support element, which includes a plurality of structural stent elements; and when the restraining wire is removably disposed in the first and the second enclosed longitudinal segments, the portion of the restraining wire disposed alongside the restraining longitudinal portion of the inner shaft prevents the full radial expansion of the longitudinal portion of the stent-graft by physically engaging at least one of the structural stent elements of the longitudinal portion of the stent-graft.

For some applications, the stent-graft includes a generally tubular support element, and a covering element that is attached to and at least partially covers the support element; and when the restraining wire is removably disposed in the first and the second enclosed longitudinal segments, the portion of the restraining wire disposed alongside the restraining longitudinal portion of the inner shaft prevents the full radial expansion of the longitudinal portion of the stent-graft by physically engaging the covering element at the longitudinal portion of the stent-graft.

For any of the applications described above, the deployment system may be configured such that when the restraining wire is removably disposed in the first and the second enclosed longitudinal segments, the portion of the restraining wire disposed alongside the restraining longitudinal portion of the inner shaft extends outward from the inner shaft. For some applications, the deployment system is configured such that a greatest distance of the restraining wire from an external surface of the inner shaft is no more than 1 mm, when the portion of the restraining wire disposed alongside the restraining longitudinal portion engages the longitudinal portion of the stent-graft, and the stent-graft is not otherwise constrained.

For any of the applications described above, the conduit may be open along the restraining longitudinal portion of the inner shaft. For some applications, the inner shaft is shaped so as to define a longitudinal slit along the restraining longitudinal portion, such that the conduit is open along the restraining longitudinal portion.

For any of the applications described above, the conduit may be shaped so as to define (a) a first opening at a first longitudinal border between the first enclosed longitudinal segment and the restraining longitudinal portion of the inner shaft, and (b) a second opening at a second longitudinal border between the second enclosed longitudinal segment and the restraining longitudinal portion of the inner shaft; and the deployment system may be configured such that when the restraining wire is removably disposed in the first and the second enclosed longitudinal segments, the restraining wire passes through the first and the second openings.

For some applications, the deployment system is configured such that when the restraining wire is removably disposed in the first and the second enclosed longitudinal segments, the portion of the restraining wire disposed alongside the restraining longitudinal portion of the inner shaft, longitudinally between the first and the second openings, extends outward from the inner shaft.

For any of the applications described above, the deployment system may further include an outer sheath, which is sized to hold the stent-graft in a first radially-compressed state when the stent-graft is disposed in the outer sheath; and when the restraining wire is removably disposed in the first and the second enclosed longitudinal segments, and the outer sheath has been withdrawn from the longitudinal portion of the stent-graft, the portion of the restraining wire disposed alongside the restraining longitudinal portion of the inner shaft prevents the full radial expansion of the longitudinal portion of the stent-graft, and allows partial radial expansion of the longitudinal portion of the stent-graft to a second radially-compressed state in which the longitudinal portion of the stent-graft is less radially compressed than in the first radially-compressed state.

For any of the applications described above, the deployment system may further include: a first ring, which is longitudinally fixed to and surrounds the inner shaft at a first longitudinal border between the first enclosed longitudinal segment and the restraining longitudinal portion of the inner shaft; and a second ring, which is longitudinally fixed to and surrounds the inner shaft at a second longitudinal border between the second enclosed longitudinal segment and the restraining longitudinal portion of the inner shaft. For some applications, the first and the second rings include a radiopaque metal.

For any of the applications described above, the apparatus may be for use with a guidewire, and the inner shaft may be shaped so as to further define a bore therethrough, which is sized for passage of the guidewire therethrough. For some applications, the bore is concentrically disposed in the inner shaft.

For any of the applications described above:
  the inner shaft may be shaped so as to define a plurality of conduits therealong, which conduits are shaped so as to define respective first enclosed longitudinal segments and respective second enclosed longitudinal segments,
  the first enclosed longitudinal segments may longitudinally coincide with one another,
  the second enclosed longitudinal segments may longitudinally coincide with one another,
  the restraining longitudinal portion of the inner shaft may be longitudinally disposed between (a) the first enclosed longitudinal segments and (b) the second enclosed longitudinal segments,
  the deployment system may include a plurality of restraining wires, and
  the deployment system may be configured such that:
    when the restraining wires are removably disposed in the first enclosed longitudinal segments, respectively, and in the second enclosed longitudinal segments, respectively, respective portions of the restraining wires disposed alongside the restraining longitudinal portion of the inner shaft prevent the full radial expansion of the longitudinal portion of the stent-graft by physically engaging the longitudinal portion of the stent-graft, and
    when the restraining wires have been withdrawn from at least the first enclosed longitudinal segments, respectively, the restraining wires do not prevent the full radial expansion of the longitudinal portion of the stent-graft.

For some applications, the plurality of conduits are circumferentially evenly distributed around the inner shaft. For some applications, the apparatus is for use with a guidewire, and the inner shaft is shaped so as to further define a bore therethrough, which is sized for passage of the guidewire therethrough. For some applications, the bore is concentrically disposed in the inner shaft. For some applications, the plurality of conduits are circumferentially evenly distributed around the bore.

For some applications, each of the restraining wires has at least one property selected from the group consisting of: a stiffness of at least $0.0002 \text{ Mm}^4$, and a Young's modulus of at least 60 GPa.

For some applications, the first enclosed longitudinal segments are distal to the second enclosed longitudinal segments, the restraining wires terminate at respective free distal ends thereof, and the deployment system is configured such that, when the restraining wires are removably disposed in the first enclosed longitudinal segments, respectively, and in the second enclosed longitudinal segments, respectively, the free distal ends of the restraining wires are disposed at respective locations, each of which is selected from the group consisting of: a location within the respective one of the first enclosed longitudinal segments, and a location distally beyond the respective one of the first enclosed longitudinal segments.

For any of the applications described above:
  the at least one conduit may be at least one first conduit, the at least one restraining wire may be at least one first restraining wire, the restraining longitudinal portion of the inner shaft may be a first restraining longitudinal portion, and the longitudinal portion of the stent-graft may be a first longitudinal portion of the stent-graft,
  the inner shaft may be shaped so as to define (a) at least one second conduit therealong, which second conduit is shaped so as to define third and fourth enclosed longitudinal segments, and (b) a second restraining longitudinal portion that is longitudinally disposed between the third and the fourth enclosed longitudinal segments, and does not longitudinally overlap the first restraining longitudinal portion,
  the deployment system may further include at least one second restraining wire, and
  the deployment system may be configured such that:
    when the second restraining wire is removably disposed in the third and the fourth enclosed longitudinal segments, a portion of the second restraining wire disposed alongside the second restraining longitudinal portion of the inner shaft prevents full radial expansion of a second longitudinal portion of the stent-graft by physically engaging the second longitudinal portion of the stent-graft,
    when the second restraining wire has been withdrawn from at least the third enclosed longitudinal segment, the second restraining wire does not prevent the full radial expansion of the second longitudinal portion of the stent-graft,
    the first restraining wire does not engage the second longitudinal portion of the stent-graft, and
    the second restraining wire does not engage the first longitudinal portion of the stent-graft.

For some applications, a longitudinal distance between longitudinally-closest ends of the first and the second longitudinal portions of the stent-graft equals at least 10% of an average of (a) a perimeter of the first longitudinal portion and (b) a perimeter of the second longitudinal portion, when the stent-graft is unconstrained in a fully radially-expanded state. Alternatively or additionally, for some applications, a longitudinal distance between longitudinally-closest ends of the first and the second longitudinal portions of the stent-graft is at least 10 mm.

For any of the applications described above:

the restraining longitudinal portion of the inner shaft may be a first restraining longitudinal portion, the portion of the restraining wire disposed alongside the first restraining longitudinal portion of the inner shaft may be a first portion of the restraining wire, and the longitudinal portion of the stent-graft may be a first longitudinal portion of the stent-graft, the conduit may be shaped so as to further define (a) a third enclosed longitudinal segment, which does not longitudinally overlap the first enclosed longitudinal segment or the second enclosed longitudinal segment, and (b) a second restraining longitudinal portion that is longitudinally disposed between the second and the third enclosed longitudinal segments, and the deployment system may be configured such that:

when the restraining wire is removably disposed in the first, the second, and the third enclosed longitudinal segments, a second portion of the restraining wire disposed alongside the second restraining longitudinal portion of the inner shaft prevents full radial expansion of a second longitudinal portion of the stent-graft by physically engaging the second longitudinal portion of the stent-graft, and when the restraining wire has been withdrawn from at least the second enclosed longitudinal segment, the restraining wire does not prevent the full radial expansion of the second longitudinal portion of the stent-graft.

For any of the applications described above, the deployment system may further include a control handle, which is coupled to a proximal portion of the inner shaft, and which includes a withdrawal actuator to which a proximal portion of the restraining wire is coupled, and the withdrawal actuator may be configured to withdraw the restraining wire in a proximal direction, thereby withdrawing the restraining wire from at least the first enclosed longitudinal segment, and releasing and allowing radial expansion of the longitudinal portion of the stent-graft. For some applications, the withdrawal actuator includes a spool to which the proximal portion of the restraining wire is coupled, and the spool is arranged such that rotation thereof withdraws the restraining wire in the proximal direction.

For any of the applications described above, the stent-graft may be shaped so as to define one or more lateral fenestrations. For some applications, the apparatus further includes one or more branching stent-grafts, which are configured to form respective blood-tight seals with the one or more lateral fenestrations, respectively.

There is further provided, in accordance with an application of the present invention, apparatus including:

a self-expanding stent-graft; and a deployment system, which includes:

an inner shaft, which is removably disposed in the stent-graft, and which is shaped so as to define (a) at least one conduit therealong, which conduit is shaped so as to define at least first and second enclosed longitudinal segments, each of which has a length of at least 5 mm, and (b) a restraining longitudinal portion that is longitudinally disposed between the first and the second enclosed longitudinal segments, and has a length equal to at least 15% of a perimeter of the inner shaft; and at least one restraining wire, wherein the deployment system is configured such that:

when the restraining wire is removably disposed in the first and the second enclosed longitudinal segments, a portion of the restraining wire disposed alongside the restraining longitudinal portion of the inner shaft prevents full radial expansion of a longitudinal portion of the stent-graft by physically engaging the longitudinal portion of the stent-graft, and when the restraining wire has been withdrawn from at least the first enclosed longitudinal segment, the restraining wire does not prevent the full radial expansion of the longitudinal portion of the stent-graft.

The apparatus may implement any of the features described hereinabove.

For some applications, the length of the restraining longitudinal portion is less than 150% of the perimeter of the inner shaft.

For some applications, the first enclosed longitudinal segment is distal to the second enclosed longitudinal segment, the restraining wire terminates at a free distal end thereof, and the deployment system is configured such that, when the restraining wire is removably disposed in the first and the second enclosed longitudinal segments, the free distal end of the restraining wire is disposed at a location selected from the group consisting of: a location within the first enclosed longitudinal segment, and a location distally beyond the first enclosed longitudinal segment.

For some applications, the restraining wire has at least one property selected from the group consisting of: a stiffness of at least 0.0002 $Mm^4$, and a Young's modulus of at least 60 GPa.

There is still further provided, in accordance with an application of the present invention, apparatus including:

a self-expanding stent-graft; and a deployment system, which includes:

an inner shaft, which is removably disposed in the stent-graft, and which is shaped so as to define (a) a plurality of conduits therealong, which conduits are shaped so as to define respective first longitudinal segments and respective second enclosed longitudinal segments, each of which first and second longitudinal segments has a length of at least 5 mm, wherein the first enclosed longitudinal segments longitudinally coincide with one another, and the second enclosed longitudinal segments longitudinally coincide with one another, and (b) a restraining longitudinal portion that is longitudinally disposed between (a) the first enclosed longitudinal segments and (b) the second enclosed longitudinal segments; and a plurality of restraining wires, which terminate at respective free distal ends thereof, wherein the deployment system is configured such that:

when the restraining wires are removably disposed in the first enclosed longitudinal segments, respectively, and in the second enclosed longitudinal segments, respectively, respective portions of the restraining wires disposed alongside the restraining longitudinal portion of the inner shaft prevent full radial expansion of a longitudinal portion of the stent-graft by physically engaging the longitudinal portion of the stent-graft, and when the restraining wires have been withdrawn from at least the first enclosed longitudinal segments, respectively, the restraining wires do not prevent the full radial expansion of the longitudinal portion of the stent-graft.

The apparatus may implement any of the features described hereinabove.

For some applications, the first enclosed longitudinal segments are distal to the second enclosed longitudinal segments, and the deployment system is configured such that, when the restraining wires are removably disposed in the first enclosed longitudinal segments, respectively, and in the second enclosed longitudinal segments, respectively, the free distal ends of the restraining wires are disposed at respective locations, each of which is selected from the group consisting of: a location within the respective one of the first enclosed longitudinal segments, and a location distally beyond the respective one of the first enclosed longitudinal segments.

For some applications, the restraining wire has at least one property selected from the group consisting of: a stiffness of at least 0.0002 $Mm^4$, and a Young's modulus of at least 60 GPa.

There is additionally provided, in accordance with an application of the present invention, apparatus including:
  a self-expanding stent-graft; and
  a deployment system, which includes:
    an inner shaft, which is removably disposed in the stent-graft, and which is shaped so as to define (a) at least one conduit therealong, which conduit is shaped so as to define at least first and second enclosed longitudinal segments, each of which has a length of at least 5 mm, wherein the first enclosed longitudinal segment is distal to the second enclosed longitudinal segment, and (b) a restraining longitudinal portion that is longitudinally disposed between the first and the second enclosed longitudinal segments; and
    at least one restraining wire, wherein the first enclosed longitudinal segment is distal to the second enclosed longitudinal segment,
  wherein the deployment system is configured such that:
    when the restraining wire is removably disposed in the first and the second enclosed longitudinal segments, (a) a portion of the restraining wire disposed alongside the restraining longitudinal portion of the inner shaft extends outward from the inner shaft and prevents full radial expansion of a longitudinal portion of the stent-graft by physically engaging the longitudinal portion of the stent-graft, and (b) the free distal end of the restraining wire is disposed at a location selected from the group consisting of: a location within the first enclosed longitudinal segment, and a location distally beyond the first enclosed longitudinal segment, and
    when the restraining wire has been withdrawn from at least the first enclosed longitudinal segment, the restraining wire does not prevent the full radial expansion of the longitudinal portion of the stent-graft.

The apparatus may implement any of the features described hereinabove.

For some applications, a length of the restraining longitudinal portion is less than 150% of a perimeter of the inner shaft.

For some applications, the restraining wire has at least one property selected from the group consisting of: a stiffness of at least 0.0002 $Mm^4$, and a Young's modulus of at least 60 GPa.

There is yet additionally provided, in accordance with an application of the present invention, apparatus including:
  a self-expanding stent-graft; and
  a deployment system, which includes:
    an inner shaft, which is removably disposed in the stent-graft, and which is shaped so as to define one or more conduits therealong, which conduits are not coaxial with the inner shaft; and
    one or more restraining wires, which are at least partially removably disposed in the conduits, and which, when so disposed, prevent full radial expansion of one or more longitudinal portions of the stent-graft by physically engaging the one or more longitudinal portions of the stent-graft.

For some applications, the one or more conduits include a plurality of conduits, and the one or more restraining wires include a plurality of restraining wires. For some applications, the conduits are at least partially removably disposed in respective ones of the conduits.

For some applications, the restraining wires terminate at respective free distal ends thereof.

For some applications, each of the restraining wires has at least one property selected from the group consisting of: a stiffness of at least 0.0002 $Mm^4$, and a Young's modulus of at least 60 GPa.

Alternatively or additionally, the apparatus may implement any of the features described hereinabove.

There is also provided, in accordance with an application of the present invention, apparatus including:
  a self-expanding stent-graft; and
  a deployment system, which includes:
    a first restraining wire, which (a) when removably disposed in physical engagement with a first longitudinal portion of the stent-graft, prevents full radial expansion of the first longitudinal portion, and (b) does not engage a second longitudinal portion of the stent-graft, which second longitudinal portion does not longitudinally overlap the first longitudinal portion; and
    a second restraining wire, which (a) when removably disposed in physical engagement with the second longitudinal portion of the stent-graft, prevents full radial expansion of the second longitudinal portion, and (b) does not engage the first longitudinal portion of the stent-graft.

For some applications, the deployment system (a) further include an inner shaft, which is removably disposed in the stent-graft, and which has non-longitudinally-overlapping first and second restraining longitudinal portions, and (b) is configured such that:
  when a first portion of the first restraining wire is disposed alongside the first restraining longitudinal portion of the inner shaft, the first portion of the first restraining wire prevents the full radial expansion of the first longitudinal portion of the stent-graft by physically engaging the first longitudinal portion of the stent-graft,
  when a second portion of the second restraining wire is disposed alongside the second restraining longitudinal portion of the inner shaft, the second portion of the second restraining wire prevents the full radial expansion of the second longitudinal portion of the stent-graft by physically engaging the second longitudinal portion of the stent-graft, when the first restraining wire has been at least partially withdrawn from alongside the first restraining longitudinal portion of the inner shaft, the first restraining wire does not prevent the full radial expansion of the first longitudinal portion of the stent-graft, and when the second restraining wire has been at least partially withdrawn from alongside the second restraining longitudinal portion of the inner shaft, the second restraining wire does not prevent the full radial expansion of the second longitudinal portion of the stent-graft.

For some applications, the first and the second restraining wires terminate at respective free distal ends thereof.

For some applications, each of the first and the second restraining wires has at least one property selected from the group consisting of: a stiffness of at least 0.0002 $Mm^4$, and a Young's modulus of at least 60 GPa.

For some applications, a longitudinal distance between longitudinally-closest ends of the first and the second longitudinal portions of the stent-graft equals at least 10% of an average of (a) a perimeter of the first longitudinal portion and (b) a perimeter of the second longitudinal portion, when the stent-graft is unconstrained in a fully radially-expanded state. Alternatively or additionally, for some applications, a longitudinal distance between longitudinally-closest ends of the first and the second longitudinal portions of the stent-graft is at least 10 mm.

For some applications:

the second restraining wire physically engages a third longitudinal portion of the stent-graft, thereby preventing full radial expansion of the third longitudinal portion, the first restraining wire does not engage the third longitudinal portion of the stent-graft, and the third longitudinal portion does not longitudinally overlap the first or the second longitudinal portions, and the first restraining longitudinal portion is longitudinally disposed between the second and the third longitudinal portions.

For some applications, the stent-graft includes a generally tubular support element, which includes a plurality of structural stent elements; and the first restraining wire physically engages at least one of the structural stent elements of the first longitudinal portion of the stent-graft.

For some applications, the stent-graft includes a generally tubular support element, and a covering element that is attached to and at least partially covers the support element; and the first restraining wire physically engages the covering element at the first longitudinal portion of the stent-graft.

For any of the applications described above, the deployment system may further include a control handle, which includes:

a first withdrawal actuator to which a proximal portion of the first restraining wire is coupled, and the first withdrawal actuator is configured to withdraw the first restraining wire in a proximal direction; and a second withdrawal actuator to which a proximal portion of the second restraining wire is coupled, and the second withdrawal actuator is configured to withdraw the second restraining wire in the proximal direction.

For some applications:

the first withdrawal actuator includes a first spool to which the proximal portion of the first restraining wire is coupled, and the first spool is arranged such that rotation thereof withdraws the first restraining wire in the proximal direction, and the second withdrawal actuator includes a second spool to which the proximal portion of the second restraining wire is coupled, and the second spool is arranged such that rotation thereof withdraws the second restraining wire in the proximal direction.

For any of the applications described above, the stent-graft may be shaped so as to define one or more lateral fenestrations. For some applications, the apparatus further includes one or more branching stent-grafts, which are configured to form respective blood-tight seals with the one or more lateral fenestrations, respectively.

There is further provided, in accordance with an application of the present invention, apparatus including a deployment system, which includes:

an inner shaft, which is shaped so as to define:

at least a first conduit therealong, which is shaped so as to define at least first and second non-longitudinally-overlapping enclosed longitudinal segments, and a first non-enclosed longitudinal portion disposed longitudinally between the first and the second enclosed longitudinal segments, and at least a second conduit therealong, which is shaped so as to define at least third and fourth non-longitudinally-overlapping enclosed longitudinal segments, and a second non-enclosed longitudinal segment disposed longitudinally between the first and the second enclosed longitudinal segments;

at least a first restraining wire, which is at least partially removably disposed in the first and the second enclosed longitudinal segments, and alongside the first non-enclosed longitudinal portion; and at least a second restraining wire, which is at least partially removably disposed in the third and the fourth enclosed longitudinal segments, and alongside the second non-enclosed longitudinal portion;

wherein the first non-enclosed longitudinal portion does not longitudinally overlap the second non-enclosed longitudinal segment, wherein the first non-enclosed longitudinal portion at least partially longitudinally overlaps one of the third and the fourth enclosed longitudinal segments, wherein the second non-enclosed longitudinal portion least partially longitudinally overlaps one of the first and the second enclosed longitudinal segments, and wherein the first and the second conduits are not coaxial with the inner shaft and are not coaxial with each other.

For some applications, a longitudinal distance between longitudinally-closest ends of the first and the second non-enclosed longitudinal segments is at least 10 mm.

For some applications, the first and the second restraining wires terminate at respective free distal ends thereof.

For some applications, each of the first and the second restraining wires has at least one property selected from the group consisting of: a stiffness of at least 0.0002 $Mm^4$, and a Young's modulus of at least 60 GPa.

For some applications, the apparatus further includes a self-expanding stent-graft, and the deployment system is configured such that:

when a first portion of the first restraining wire is disposed alongside the first non-enclosed longitudinal portion of the inner shaft, the first portion of the first restraining wire prevents full radial expansion of a first longitudinal portion of the stent-graft by physically engaging the first longitudinal portion of the stent-graft, when a second portion of the second restraining wire is disposed alongside the second non-enclosed longitudinal portion of the inner shaft, the second portion of the second restraining wire prevents full radial expansion of a second longitudinal portion of the stent-graft by physically engaging the second longitudinal portion of the stent-graft, when the first restraining wire has been at least partially withdrawn from alongside the first non-enclosed longitudinal portion of the inner shaft, the first restraining wire does not prevent the full radial expansion of the first longitudinal portion of the stent-graft, and when the second restraining wire has been at least partially withdrawn from alongside the second non-enclosed longitudinal portion of the inner shaft, the second restraining wire does not prevent the full radial expansion of the second longitudinal portion of the stent-graft.

For any of the applications described above, the deployment system may further include a control handle, which includes:

a first withdrawal actuator to which a proximal portion of the first restraining wire is coupled, and the first withdrawal actuator is configured to withdraw the first restraining wire in a proximal direction; and a second withdrawal actuator to which a proximal portion of the second restraining wire is coupled, and the second withdrawal actuator is configured to withdraw the second restraining wire in the proximal direction.

For some applications, the first withdrawal actuator includes a first spool to which the proximal portion of the first restraining wire is coupled, and the first spool is arranged such that rotation thereof withdraws the first restraining wire in the proximal direction; and the second withdrawal actuator includes a second spool to which the proximal portion of the second restraining wire is coupled, and the second spool is arranged such that rotation thereof withdraws the second restraining wire in the proximal direction.

There is still further provided, in accordance with an application of the present invention, apparatus including:
a self-expanding stent-graft; and
a deployment system, which includes:
at least first and second restraining wires, which physically engage respective longitudinal portions of the stent-graft, thereby preventing full radial expansion of the longitudinal portions; and
a control handle, which includes:
a first withdrawal actuator to which a proximal portion of the first restraining wire is coupled, wherein the first withdrawal actuator is configured to withdraw the first restraining wire in a proximal direction; and
a second withdrawal actuator to which a proximal portion of the second restraining wire is coupled, wherein the second withdrawal actuator is configured to withdraw the second restraining wire in the proximal direction.

For some applications:
the first withdrawal actuator includes a first spool to which the proximal portion of the first restraining wire is coupled, and the first spool is arranged such that rotation thereof withdraws the first restraining wire in the proximal direction, and
the second withdrawal actuator includes a second spool to which the proximal portion of the second restraining wire is coupled, and the second spool is arranged such that rotation thereof withdraws the second restraining wire in the proximal direction.

For some applications, the first and the second restraining wires terminate at respective free distal ends thereof.

For some applications, each of the first and the second restraining wires has at least one property selected from the group consisting of: a stiffness of at least 0.0002 $Mm^4$, and a Young's modulus of at least 60 GPa.

There is additionally provided, in accordance with an application of the present invention, apparatus including:
a self-expanding stent-graft; and
a deployment system, which includes:
at least first and second restraining wires, which physically engage respective longitudinal portions of the stent-graft, thereby preventing full radial expansion of the longitudinal portions; and
a control handle, which:
includes a withdrawal actuator, which includes a spool, to which a proximal portion of the first restraining wire is coupled, wherein the first withdrawal actuator is configured to withdraw the first restraining wire in a proximal direction, and
is shaped so as to define a lumen open to an external surface of the control handle, through which lumen the second restraining wire passes.

For some applications, the first and the second restraining wires terminate at respective free distal ends thereof.

For some applications, each of the first and the second restraining wires has at least one property selected from the group consisting of: a stiffness of at least 0.0002 $Mm^4$, and a Young's modulus of at least 60 GPa.

There is yet additionally provided, in accordance with an application of the present invention, a method including:
advancing an inner shaft of a deployment system through a body lumen of a subject, while the inner shaft is removably disposed in a self-expanding stent-graft, wherein the inner shaft is shaped so as to define (a) at least one conduit therealong, which conduit is (i) not coaxial with the inner shaft, and (ii) shaped so as to define at least first and second enclosed longitudinal segments, each of which has a length of at least 30 mm, and (b) a restraining longitudinal portion that is longitudinally disposed between the first and the second enclosed longitudinal segments, wherein advancing includes advancing the inner shaft while a restraining wire of the deployment system is removably disposed in the first and the second enclosed longitudinal segments, and a portion of the restraining wire disposed alongside the restraining longitudinal portion of the inner shaft prevents full radial expansion of a longitudinal portion of the stent-graft by physically engaging the longitudinal portion of the stent-graft; and
withdrawing the restraining wire from at least the first enclosed longitudinal segment, such that the restraining wire does not prevent the full radial expansion of the longitudinal portion of the stent-graft.

For some applications, the restraining longitudinal portion of the inner shaft has a length equal to at least 15% of a perimeter of the inner shaft. Alternatively or additionally, for some applications, the length is less than 150% of the perimeter. For some applications, the restraining longitudinal portion of the inner shaft has a length equal to less than 15% of a perimeter of the longitudinal portion of the stent-graft when the stent-graft is unconstrained in a fully radially-expanded state, such as less than 5% of the perimeter. For some applications, the restraining longitudinal portion of the inner shaft has a length of less than 20 mm. For some applications, the length is less than 10 mm, such as less than 5 mm. For some applications, the restraining longitudinal portion of the inner shaft has a length equal to less than 150% of a perimeter of the inner shaft, such as less than 100% of the perimeter. For some applications, the inner shaft has an outer diameter of no more than 4 mm. For some applications, each of the first and the second enclosed longitudinal segments has an inner diameter of no more than 3 mm.

For some applications, withdrawing the restraining wire comprises withdrawing the restraining wire in a proximal direction, and advancing the inner shaft comprises applying no tensile force or less than 10 N of tensile force to a proximal portion of the restraining wire while advancing the inner shaft.

For some applications, advancing includes advancing the inner shaft while the restraining wire is removably disposed in the first and the second enclosed longitudinal segments, such that the portion of the restraining wire disposed alongside the restraining longitudinal portion of the inner shaft extends outward from the inner shaft. For some applications, advancing includes advancing the inner shaft while a greatest distance of the restraining wire from an external surface of the inner shaft is no more than 1 mm.

For some applications, the length of at least one of the first and the second enclosed longitudinal segments is at least 30 mm.

For some applications, the restraining wire has a diameter of between 0.08 and 0.3 mm.

For some applications, the restraining wire has at least one property selected from the group consisting of: a stiffness of at least $0.0002$ $Mm^4$, and a Young's modulus of at least 60 GPa.

For some applications, the first enclosed longitudinal segment is distal to the second enclosed longitudinal segment, the restraining wire terminates at a free distal end thereof, and advancing comprises advancing the inner shaft while the restraining wire is removably disposed in the first and the second enclosed longitudinal segments, and the free distal end of the restraining wire is disposed at a location selected from the group consisting of: a location within the first enclosed longitudinal segment, and a location distally beyond the first enclosed longitudinal segment.

For some applications, the stent-graft includes a generally tubular support element, which includes a plurality of structural stent elements; and advancing includes advancing the inner shaft while the restraining wire is removably disposed in the first and the second enclosed longitudinal segments, and the portion of the restraining wire disposed alongside the restraining longitudinal portion of the inner shaft prevents the full radial expansion of the longitudinal portion of the stent-graft by physically engaging at least one of the structural stent elements of the longitudinal portion of the stent-graft.

For some applications, the stent-graft includes a generally tubular support element, and a covering element that is attached to and at least partially covers the support element; and advancing includes advancing the inner shaft while the restraining wire is removably disposed in the first and the second enclosed longitudinal segments, and the portion of the restraining wire disposed alongside the restraining longitudinal portion of the inner shaft prevents the full radial expansion of the longitudinal portion of the stent-graft by physically engaging the covering element at the longitudinal portion of the stent-graft.

For some applications, the conduit is open along the restraining longitudinal portion of the inner shaft. For some applications, the inner shaft is shaped so as to define a longitudinal slit along the restraining longitudinal portion, such that the conduit is open along the restraining longitudinal portion.

For some applications, the conduit is shaped so as to define (a) a first opening at a first longitudinal border between the first enclosed longitudinal segment and the restraining longitudinal portion of the inner shaft, and (b) a second opening at a second longitudinal border between the second enclosed longitudinal segment and the restraining longitudinal portion of the inner shaft; and the deployment system is configured such that when the restraining wire is removably disposed in the first and the second enclosed longitudinal segments, the restraining wire passes through the first and the second openings. For some applications, advancing includes advancing the inner shaft while the portion of the restraining wire disposed alongside the restraining longitudinal portion of the inner shaft, longitudinally between the first and the second openings, extends outward from the inner shaft.

For some applications, advancing includes advancing the inner shaft while the stent-graft is disposed in an outer sheath of the deployment system, which outer sheath holds the stent-graft in a first radially-compressed state; and the method further includes, before withdrawing the restraining wire from at least the first enclosed longitudinal segment, withdrawing the outer sheath from the longitudinal portion of the stent-graft, such that the portion of the restraining wire disposed alongside the restraining longitudinal portion of the inner shaft prevents the full radial expansion of the longitudinal portion of the stent-graft, and allows partial radial expansion of the longitudinal portion of the stent-graft to a second radially-compressed state in which the longitudinal portion of the stent-graft is less radially compressed than in the first radially-compressed state.

For some applications, the deployment system further includes a first ring, which is longitudinally fixed to and surrounds the inner shaft at a first longitudinal border between the first enclosed longitudinal segment and the restraining longitudinal portion of the inner shaft; and a second ring, which is longitudinally fixed to and surrounds the inner shaft at a second longitudinal border between the second enclosed longitudinal segment and the restraining longitudinal portion of the inner shaft. For some applications, the first and the second rings include a radiopaque metal.

For some applications, the inner shaft is shaped so as to further define a bore therethrough, which is sized for passage of a guidewire therethrough; the method further includes, before advancing the inner shaft through the body lumen, advancing the guidewire through the body lumen; and advancing the inner shaft includes advancing the inner shaft over the guidewire, while the guidewire passes through the bore. For some applications, the bore is concentrically disposed in the inner shaft.

For some applications:

the inner shaft is shaped so as to define a plurality of conduits therealong, which conduits are shaped so as to define respective first enclosed longitudinal segments and respective second enclosed longitudinal segments, the first enclosed longitudinal segments longitudinally coincide with one another, the second enclosed longitudinal segments longitudinally coincide with one another, the restraining longitudinal portion of the inner shaft is longitudinally disposed between (a) the first enclosed longitudinal segments and (b) the second enclosed longitudinal segments, the deployment system includes a plurality of restraining wires, advancing includes advancing the inner shaft while the restraining wires are removably disposed in the first enclosed longitudinal segments, respectively, and in the second enclosed longitudinal segments, respectively, and respective portions of the restraining wires disposed alongside the restraining longitudinal portion of the inner shaft prevent the full radial expansion of the longitudinal portion of the stent-graft by physically engaging the longitudinal portion of the stent-graft, and withdrawing the restraining wire includes withdrawing the restraining wires from at least the first enclosed longitudinal segments, respectively, such that the restraining wires do not prevent the full radial expansion of the longitudinal portion of the stent-graft.

For some applications, the plurality of conduits are circumferentially evenly distributed around the inner shaft.

For some applications, the inner shaft is shaped so as to further define a bore therethrough, which is sized for passage of a guidewire therethrough; the method further includes, before advancing the inner shaft through the body lumen, advancing the guidewire through the body lumen; and advancing the inner shaft includes advancing the inner shaft over the guidewire, while the guidewire passes through the bore. For some applications, the bore is concentrically disposed in the inner shaft. For some applications, the plurality of conduits are circumferentially evenly distributed around the bore.

For some applications, each of the restraining wires has at least one property selected from the group consisting of: a stiffness of at least 0.0002 $Mm^4$, and a Young's modulus of at least 60 GPa.

For some applications, the first enclosed longitudinal segments are distal to the second enclosed longitudinal segments, the restraining wires terminate at respective free distal ends thereof, and advancing comprises advancing the inner shaft while the restraining wires are removably disposed in the first enclosed longitudinal segments, respectively, and in the second enclosed longitudinal segments, respectively, and the free distal ends of the restraining wires are disposed at respective locations, each of which is selected from the group consisting of: a location within the respective one of the first enclosed longitudinal segments, and a location distally beyond the respective one of the first enclosed longitudinal segments.

For some applications:

the at least one conduit is at least one first conduit, the at least one restraining wire is at least one first restraining wire, the restraining longitudinal portion of the inner shaft is a first restraining longitudinal portion, and the longitudinal portion of the stent-graft is a first longitudinal portion of the stent-graft, the inner shaft is shaped so as to define (a) at least one second conduit therealong, which second conduit is shaped so as to define third and fourth enclosed longitudinal segments, and (b) a second restraining longitudinal portion that is longitudinally disposed between the third and the fourth enclosed longitudinal segments, and does not longitudinally overlap the first restraining longitudinal portion, the deployment system further includes at least one second restraining wire, advancing includes advancing the inner shaft while the second restraining wire is removably disposed in the third and the fourth enclosed longitudinal segments, and a portion of the second restraining wire disposed alongside the second restraining longitudinal portion of the inner shaft prevents full radial expansion of a second longitudinal portion of the stent-graft by physically engaging the second longitudinal portion of the stent-graft, the method further includes withdrawing the second restraining wire from at least the third enclosed longitudinal segment, such that the second restraining wire does not prevent the full radial expansion of the second longitudinal portion of the stent-graft, the first restraining wire does not engage the second longitudinal portion of the stent-graft, and the second restraining wire does not engage the first longitudinal portion of the stent-graft.

For some applications, a longitudinal distance between longitudinally-closest ends of the first and the second longitudinal portions of the stent-graft equals at least 10% of an average of (a) a perimeter of the first longitudinal portion and (b) a perimeter of the second longitudinal portion, when the stent-graft is unconstrained in a fully radially-expanded state. Alternatively or additionally, for some applications, a longitudinal distance between longitudinally-closest ends of the first and the second longitudinal portions of the stent-graft is at least 10 mm.

For some applications:

the restraining longitudinal portion of the inner shaft is a first restraining longitudinal portion, the portion of the restraining wire disposed alongside the first restraining longitudinal portion of the inner shaft is a first portion of the restraining wire, and the longitudinal portion of the stent-graft is a first longitudinal portion of the stent-graft, the conduit is shaped so as to further define (a) a third enclosed longitudinal segment, which does not longitudinally overlap the first enclosed longitudinal segment or the second enclosed longitudinal segment, and (b) a second restraining longitudinal portion that is longitudinally disposed between the second and the third enclosed longitudinal segments, advancing includes advancing the inner shaft while the restraining wire is removably disposed in the first, the second, and the third enclosed longitudinal segments, and a second portion of the restraining wire disposed alongside the second restraining longitudinal portion of the inner shaft prevents full radial expansion of a second longitudinal portion of the stent-graft by physically engaging the second longitudinal portion of the stent-graft, and the method further includes withdrawing the restraining wire from at least the second enclosed longitudinal segment, such that the restraining wire does not prevent the full radial expansion of the second longitudinal portion of the stent-graft.

For some applications, the deployment system further includes a control handle, which is coupled to a proximal portion of the inner shaft, and which includes a withdrawal actuator to which a proximal portion of the restraining wire is coupled; and withdrawing the restraining wire includes actuating the withdrawal actuator to withdraw the restraining wire in a proximal direction, thereby withdrawing the restraining wire from at least the first enclosed longitudinal segment, and releasing and allowing radial expansion of the longitudinal portion of the stent-graft. For some applications, the withdrawal actuator includes a spool to which the proximal portion of the restraining wire is coupled, and actuating the withdrawal actuator includes rotating the spool to withdraw the restraining wire in the proximal direction.

For some applications, the stent-graft is shaped so as to define one or more lateral fenestrations. For some applications, the method further includes advancing one or more branching stent-grafts into respective branching blood body lumen that branch from the body lumen; and radially expanding the one or more branching stent-grafts so that the branching stent-grafts form respective blood-tight seals with the one or more lateral fenestrations, respectively.

There is also provided, in accordance with an application of the present invention, a method including:

advancing an inner shaft of a deployment system through a body lumen of a subject, while the inner shaft is removably disposed in a self-expanding stent-graft, wherein the inner shaft is shaped so as to define one or more conduits therealong, which conduits are not coaxial with the inner shaft, wherein advancing includes advancing the inner shaft while one or more restraining wires of the deployment system are at least partially removably disposed in conduits, and prevent full radial expansion of one or more longitudinal portions of the stent-graft by physically engaging the one or more longitudinal portions of the stent-graft; and at least partially withdrawing the one or more restraining wires, such that the one or more restraining wires do not prevent the full radial expansion of the one or more longitudinal portions of the stent-graft.

For some applications, the one or more conduits include a plurality of conduits, and the one or more restraining wires include a plurality of restraining wires. For some applications, advancing includes advancing the inner shaft while the conduits are at least partially removably disposed in respective ones of the conduits.

For some applications, withdrawing the one or more restraining wires comprises withdrawing the one or more restraining wires in a proximal direction, and advancing the inner shaft comprises applying no tensile force or less than 10 N of tensile force to respective proximal portions of the one or more restraining wires while advancing the inner shaft.

For some applications, the restraining wires terminate at respective free distal ends thereof.

For some applications, each of the restraining wires has at least one property selected from the group consisting of: a stiffness of at least 0.0002 Mm$^4$, and a Young's modulus of at least 60 GPa.

There is further provided, in accordance with an application of the present invention, a method including:

advancing an inner shaft of a deployment system through a body lumen of a subject, while the inner shaft is removably disposed in a self-expanding stent-graft, and while a plurality of restraining wires of the deployment system physically engage the stent-graft and prevent full radial expansion of at least a portion of the stent-graft;

at least partially withdrawing a first subset of the restraining wires, which first subset includes at least a first one of the restraining wires; and after at least partially withdrawing the first subset of the restraining wires, at least partially withdrawing a second subset of the restraining wires, which second subset is different from the first subset and includes at least a second one of the restraining wires.

For some applications, at least partially withdrawing the second subset includes beginning at least partially withdrawing the second subset at least one second after at least partially withdrawing the first subset.

For some applications, withdrawing the first and the second subsets of the restraining wires comprises withdrawing the first and the second subsets of the restraining wires in a proximal direction, and advancing the inner shaft comprises applying no tensile force or less than 10 N of tensile force to respective proximal portions of the plurality of restraining wires while advancing the inner shaft.

For some applications, the restraining wires terminate at respective free distal ends thereof.

For some applications, each of the restraining wires has at least one property selected from the group consisting of: a stiffness of at least 0.0002 Mm$^4$, and a Young's modulus of at least 60 GPa.

For some applications, advancing includes advancing the inner shaft while:

the first one of the restraining wires (a) physically engages a first longitudinal portion of the stent-graft, thereby preventing full radial expansion of the first longitudinal portion, and (b) does not engage a second longitudinal portion of the stent-graft, which second longitudinal portion does not longitudinally overlap the first longitudinal portion, and the second one of the restraining wires (a) physically engages the second longitudinal portion of the stent-graft, thereby preventing full radial expansion of the second longitudinal portion, and (b) does not engage the first longitudinal portion of the stent-graft.

For some applications:

the deployment system further includes a control handle, which includes (a) a first withdrawal actuator, to which a proximal portion of the first subset of the restraining wires is coupled, and (b) a second withdrawal actuator, to which a proximal portion of the second subset of the restraining wires is coupled, at least partially withdrawing the first subset includes actuating the first withdrawal actuator to at least partially withdraw the first subset in a proximal direction, and at least partially withdrawing the second subset includes actuating the second withdrawal actuator to at least partially withdraw the second subset in a proximal direction.

For some applications:

the first withdrawal actuator includes a first spool to which the proximal portion of the first subset is coupled, the second withdrawal actuator includes a second spool to which the proximal portion of the second subset is coupled, actuating the first withdrawal actuator includes rotating the first spool to at least partially withdraw the first subset in the proximal direction, and actuating the second withdrawal actuator includes rotating the second spool to at least partially withdraw the second subset in the proximal direction.

For some applications:

the deployment system further includes a control handle, which (a) includes a withdrawal actuator, which includes a spool to which a proximal portion of the first subset of the restraining wires is coupled, and (b) is shaped so as to define one or more lumens open to an external surface of the control handle, through which lumen the second subset of the restraining wires passes, at least partially withdrawing the first subset includes rotating the spool to at least partially withdraw the first subset in a proximal direction, and at least partially withdrawing the second subset includes pulling on the second subset of restraining wires from outside the control handle.

For some applications:

the deployment system further includes a control handle, which (a) includes a withdrawal actuator, which includes a spool to which a proximal portion of the second subset of the restraining wires is coupled, and (b) is shaped so as to define one or more lumens open to an external surface of the control handle, through which lumen the first subset of the restraining wires passes, at least partially withdrawing the first subset includes pulling on the first subset of restraining wires from outside the control handle, and at least partially withdrawing the second subset includes rotating the spool to at least partially withdraw the second subset in a proximal direction.

There is still further provided, in accordance with an application of the present invention, a method including:
advancing an inner shaft of a deployment system through a body lumen of a subject, while:
the inner shaft is removably disposed in a self-expanding stent-graft,
a first restraining wire (a) physically engages a first longitudinal portion of the stent-graft, thereby preventing full radial expansion of the first longitudinal portion, and (b) does not engage a second longitudinal portion of the stent-graft, which second longitudinal portion does not longitudinally overlap the first longitudinal portion, and
a second restraining wire (a) physically engages the second longitudinal portion of the stent-graft, thereby preventing full radial expansion of the second longitudinal portion, and (b) does not engage the first longitudinal portion of the stent-graft;
at least partially withdrawing the first restraining wire; and
at least partially withdrawing the second restraining wire.

For some applications, advancing includes advancing the inner shaft while the second restraining wire physically engages a third longitudinal portion of the stent-graft, thereby preventing full radial expansion of the third longitudinal portion, and while the first restraining wire does not engage the third longitudinal portion of the stent-graft, and the third longitudinal portion does not longitudinally overlap the first or the second longitudinal portions, and the first restraining longitudinal portion is longitudinally disposed between the second and the third longitudinal portions.

For some applications:
the deployment system further includes a control handle, which includes (a) a first withdrawal actuator to which a proximal portion of the first restraining wire is coupled, and (b) a second withdrawal actuator to which a proximal portion of the second restraining wire is coupled,
at least partially withdrawing the first restraining wire includes actuating the first withdrawal actuator to at least partially withdraw the first restraining wire in a proximal direction, and
at least partially withdrawing the second restraining wire includes actuating the second withdrawal actuator to at least partially withdraw the second restraining wire in the proximal direction.

For some applications:
the first withdrawal actuator includes a first spool to which the proximal portion of the first restraining wire is coupled,
the second withdrawal actuator includes a second spool to which the proximal portion of the second restraining wire is coupled,
actuating the first withdrawal actuator includes rotating the first spool to at least partially withdraw the first restraining wire in the proximal direction, and
actuating the first withdrawal actuator includes rotating the second spool to at least partially withdraw the second restraining wire in the proximal direction.

For some applications, the stent-graft is shaped so as to define one or more lateral fenestrations. For some applications, the method further includes advancing one or more branching stent-grafts into respective branching blood body lumen that branch from the body lumen; and radially expanding the one or more branching stent-grafts so that the branching stent-grafts form respective blood-tight seals with the one or more lateral fenestrations, respectively.

For some applications, withdrawing the first and the second restraining wires comprises withdrawing the first and the second restraining wires in a proximal direction, and advancing the inner shaft comprises applying no tensile force or less than 10 N of tensile force to respective proximal portions of the first and the second restraining wires while advancing the inner shaft.

For some applications, the first and the second restraining wires terminate at respective free distal ends thereof.

For some applications, each of the first and the second restraining wires has at least one property selected from the group consisting of: a stiffness of at least 0.0002 $Mm^4$, and a Young's modulus of at least 60 GPa.

There is additionally provided, in accordance with an application of the present invention, a method including:
providing an inner shaft of a deployment system, which inner shaft is shaped so as to define: (a) at least a first conduit therealong, which is shaped so as to define at least first and second non-longitudinally-overlapping enclosed longitudinal segments, and a first non-enclosed longitudinal portion disposed longitudinally between the first and the second enclosed longitudinal segments, and (b) at least a second conduit therealong, which is shaped so as to define at least third and fourth non-longitudinally-overlapping enclosed longitudinal segments, and a second non-enclosed longitudinal segment disposed longitudinally between the first and the second enclosed longitudinal segments;
advancing the inner shaft through a body lumen of a subject, while (a) at least a first restraining wire is at least partially removably disposed in the first and the second enclosed longitudinal segments, and alongside the first non-enclosed longitudinal portion, and (b) at least a second restraining wire is at least partially removably disposed in the third and the fourth enclosed longitudinal segments, and alongside the second non-enclosed longitudinal portion;
at least partially withdrawing the first restraining wire; and
at least partially withdrawing the second restraining wire,
wherein the first non-enclosed longitudinal portion does not longitudinally overlap the second non-enclosed longitudinal segment,
wherein the first non-enclosed longitudinal portion at least partially longitudinally overlaps one of the third and the fourth enclosed longitudinal segments,
wherein the second non-enclosed longitudinal portion least partially longitudinally overlaps one of the first and the second enclosed longitudinal segments, and
wherein the first and the second conduits are not coaxial with the inner shaft and are not coaxial with each other.

For some applications, a longitudinal distance between longitudinally-closest ends of the first and the second non-enclosed longitudinal segments is at least 10 mm.

For some applications:
advancing the inner shaft includes advancing the inner shaft through the body lumen while:
the inner shaft is removably disposed in a self-expanding stent-graft,
a first portion of the first restraining wire is disposed alongside the first non-enclosed longitudinal portion of the inner shaft, such that first portion of the first restraining wire prevents full radial expansion of a first longitudinal portion of the stent-graft by physically engaging the first longitudinal portion of the stent-graft, a second portion of the second restraining wire is disposed alongside the second non-enclosed longitudinal portion of the inner shaft, such that the second portion of the second restraining wire prevents full radial expansion of a second longitudinal portion of the stent-graft by physically engaging the second longitudinal portion of the stent-graft, at least partially withdrawing the first restraining wire includes at least partially withdrawing the first restraining from alongside the first non-enclosed longitudinal portion of the inner shaft, such that the first restraining wire does not prevent the full radial expansion of the first longitudinal portion of the stent-graft, and at least partially withdrawing the second restraining wire includes at least partially withdrawing the second restraining wire from alongside the second non-enclosed longitudinal portion of the inner shaft, such that the second restraining wire does not prevent the full radial expansion of the second longitudinal portion of the stent-graft.

For some applications:

the deployment system further includes a control handle, which includes (a) a first withdrawal actuator to which a proximal portion of the first restraining wire is coupled, and (b) a second withdrawal actuator to which a proximal portion of the second restraining wire is coupled, at least partially withdrawing the first restraining wire includes actuating the first withdrawal actuator to at least partially withdraw the first restraining wire in a proximal direction, and at least partially withdrawing the second restraining wire includes actuating the second withdrawal actuator to at least partially withdraw the second restraining wire in the proximal direction.

For some applications:

the first withdrawal actuator includes a first spool to which the proximal portion of the first restraining wire is coupled, the second withdrawal actuator includes a second spool to which the proximal portion of the second restraining wire is coupled, actuating the first withdrawal actuator includes rotating the first spool to at least partially withdraw the first restraining wire in the proximal direction, and actuating the first withdrawal actuator includes rotating the second spool to at least partially withdraw the second restraining wire in the proximal direction.

For some applications, withdrawing the first and the second restraining wires comprises withdrawing the first and the second restraining wires in a proximal direction, and advancing the inner shaft comprises applying no tensile force or less than 10 N of tensile force to respective proximal portions of the first and the second restraining wires while advancing the inner shaft.

For some applications, the first and the second restraining wires terminate at respective free distal ends thereof.

For some applications, each of the first and the second restraining wires has at least one property selected from the group consisting of: a stiffness of at least 0.0002 Mm$^4$, and a Young's modulus of at least 60 GPa.

There is yet additionally provided, in accordance with an application of the present invention, a method including:

advancing an inner shaft of a deployment system through a body lumen of a subject, while the inner shaft is removably disposed in a self-expanding stent-graft, and while at least first and second restraining wires of the deployment system physically engage respective longitudinal portions of the stent-graft, thereby preventing full radial expansion of the longitudinal portions;

at least partially withdrawing the first restraining wire in a proximal direction by actuating a first withdrawal actuator of a control handle, to which first withdrawal actuator a proximal portion of the first restraining wire is coupled; and at least partially withdrawing the second restraining wire in the proximal direction by actuating a second withdrawal actuator of the control handle, to which second withdrawal actuator a proximal portion of the second restraining wire is coupled.

For some applications:

the first withdrawal actuator includes a first spool to which the proximal portion of the first restraining wire is coupled, the second withdrawal actuator includes a second spool to which the proximal portion of the second restraining wire is coupled, actuating the first withdrawal actuator includes rotating the first spool to at least partially withdraw the first restraining wire in the proximal direction, and actuating the first withdrawal actuator includes rotating the second spool to at least partially withdraw the second restraining wire in the proximal direction.

For some applications, withdrawing the first and the second restraining wires comprises withdrawing the first and the second restraining wires in a proximal direction, and advancing the inner shaft comprises applying no tensile force or less than 10 N of tensile force to respective proximal portions of the first and the second restraining wires while advancing the inner shaft.

For some applications, the first and the second restraining wires terminate at respective free distal ends thereof.

For some applications, each of the first and the second restraining wires has at least one property selected from the group consisting of: a stiffness of at least 0.0002 Mm$^4$, and a Young's modulus of at least 60 GPa.

There is also provided, in accordance with an application of the present invention, a method including:

advancing an inner shaft of a deployment system through a body lumen of a subject, while the inner shaft is removably disposed in a self-expanding stent-graft, and while at least first and second restraining wires of the deployment system physically engage respective longitudinal portions of the stent-graft, thereby preventing full radial expansion of the longitudinal portions;

at least partially withdrawing the first restraining wire in a proximal direction by actuating a withdrawal actuator of a control handle, which withdrawal actuator includes a spool to which a proximal portion of the first restraining wire is coupled; and at least partially withdrawing the second restraining wire in the proximal direction by pulling on the second restraining wire, which passes through a lumen of the control handle, which lumen is open to an external surface of the control handle.

For some applications, withdrawing the first and the second restraining wires comprises withdrawing the first and the second restraining wires in a proximal direction, and advancing the inner shaft comprises applying no tensile force or less than 10 N of tensile force to respective proximal portions of the first and the second restraining wires while advancing the inner shaft.

For some applications, the first and the second restraining wires terminate at respective free distal ends thereof.

For some applications, each of the first and the second restraining wires has at least one property selected from the group consisting of: a stiffness of at least 0.0002 Mm$^4$, and a Young's modulus of at least 60 GPa.

The present invention will be more fully understood from the following detailed description of embodiments thereof, taken together with the drawings, in which:

BRIEF DESCRIPTION OF THE DRAWINGS

FIG. 2 is a schematic illustration of a distal portion of a delivery shaft of the stent-graft deployment system of FIG. 1, in accordance with an application of the present invention;

FIG. 3 is a schematic illustration of a self-expanding stent-graft disposed along a distal portion of the delivery shaft of FIGS. 1 and 2, in accordance with an application of the present invention;

FIGS. 4A and 4B are schematic cross-sectional views of respective longitudinal portions of the delivery shaft and the stent-graft of FIG. 3, in accordance with an application of the present invention;

FIG. 4C is a highly schematic cross-sectional illustration of a portion of the delivery shaft of FIGS. 1 and 2, a single restraining wire, and a single structural element of a stent-graft, in accordance with an application of the present invention;

FIG. 5 is a schematic illustration of another configuration of a restraining longitudinal portion of the delivery shaft of FIGS. 1-3, in accordance with an application of the present invention;

FIGS. 6A-F are schematic illustrations of a deployment of a stent-graft from stent-graft deployment system of FIGS. 1-5, in accordance with an application of the present invention;

FIGS. 7A-C are schematic illustrations of two stages of a deployment of a stent-graft from the stent-graft deployment system of FIGS. 1-5, in accordance with an application of the present invention;

FIGS. 8 and 9 are schematic illustrations of alternative configurations of stent-grafts, respectively, in accordance with respective applications of the present invention;

FIGS. 10A-G are schematic illustrations of an exemplary method of using the stent-graft deployment system of FIGS. 1-6F and 8, to deploy the stent-graft of FIGS. 1-6F and 8, in accordance with an application of the present invention;

FIGS. 12A-C are schematic cross-sectional views of respective longitudinal portions of the delivery shaft of FIG. 11 and a stent-graft, in accordance with an application of the present invention;

FIGS. 13A-J are schematic illustrations of an exemplary method of using the stent-graft deployment system of FIGS. 11-12C to deploy the stent-graft of FIGS. 7A-C and 9, in accordance with an application of the present invention;

DETAILED DESCRIPTION OF APPLICATIONS

Figure 1:
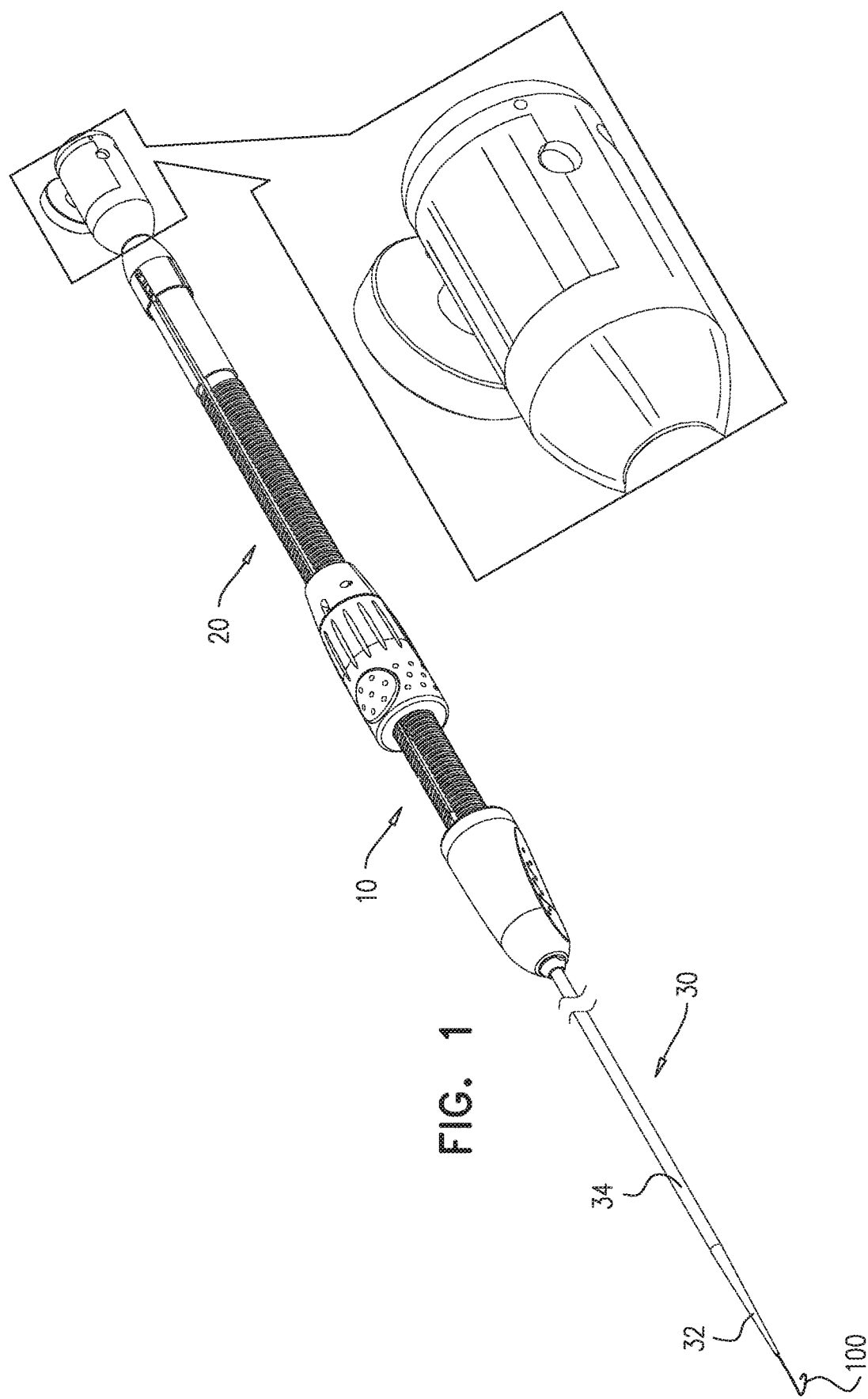
FIG. 1 is a schematic illustration of a stent-graft deployment system, in accordance with an application of the present invention.

FIG. 1 is a schematic illustration of a stent-graft deployment system 10, in accordance with an application of the present invention. Deployment system 10 is configured to deliver and deploy a stent-graft to a lumen of a mammalian (e.g., human) body, such as a blood vessel, e.g., an artery. Deployment system 10 comprises a control handle 20, for controlling the deployment system, and an elongated delivery shaft 30, for insertion into the body lumen and delivery of the stent-graft. Deployment system 10 typically further comprises an outer sheath 34, which typically is initially disposed extending to the distal tip. As described hereinbelow, outer sheath 34 is sized to hold the stent-graft in a radially-compressed state when the stent-graft is disposed in the outer sheath during advancing of the delivery shaft into the body lumen. The outer sheath primarily facilitates complete radial confinement of the stent-graft until its deployment, and may also provide protection of the vasculature from potentially traumatic elements in the wall of stent-graft 40; the former being its primary role for self-expanding prostheses (e.g., stent-grafts), while the latter is the primary role of such external sheaths for balloon-expandable prostheses (e.g., covered branches for the visceral arteries), such as described hereinbelow with reference to FIGS. 13I-J.

Reference is made to FIG. 2, which is a schematic illustration of a distal portion of delivery shaft 30, in accordance with an application of the present invention. Delivery shaft 30 comprises an inner shaft 36 and a distal tip 32. Outer sheath 34 surrounds at least a longitudinal portion of inner shaft 36. By way of illustration, in FIG. 2 outer sheath 34 is shown partially proximally withdrawn from inner shaft 36.

Reference is now made to FIG. 3, which is a schematic illustration of a self-expanding stent-graft 40 disposed along a distal portion of delivery shaft 30, in accordance with an application of the present invention. Inner shaft 36 is shown removably disposed within stent-graft 40, which in turn is radially constrained by outer sheath 34. By way of illustration, in FIG. 3 outer sheath 34 is shown disposed extending to distal tip 32. Inner shaft 36 typically has an outer diameter of no more than 4 mm, such as no more than 1.5 mm, e.g., between 1.0 and 1.5 mm, which may enable the total crossing profile (i.e., outer diameter) of delivery shaft 30, including outer sheath 34, when stent-graft 40 is disposed there in a radially-compressed state, to be no more than 25 Fr (approximately 8 mm).

As labeled in FIG. 6F, which is described hereinbelow, self-expanding stent-graft 40 comprises a generally tubular support element 42, and a covering element 44 that is attached to and at least partially covers (e.g., only partially covers) the support element. Support element 42 typically comprises a plurality of structural stent elements 46. For some applications, structural stent elements 46 are arranged as a plurality of circumferential stent springs 48. For some applications, support element 42 comprises a metal (such as an elastic metal, or stainless steel), a super-elastic alloy (such as Nitinol). Covering element 44 serves as a blood flow guide through at least a portion of the stent-graft. Covering element 44 typically comprises at least one biologically-compatible substantially blood-impervious flexible sheet, which is attached (such as by stitching) to at least a portion of the respective support element, on either side of the surfaces defined by the support element. The flexible sheet may comprise, for example, a polymeric material (e.g., a polyester, or polytetrafluoroethylene), a textile material (e.g., polyethylene terephthalate (PET), or expanded polytetrafluoroethylene (ePTFE)), natural tissue (e.g., saphenous vein or collagen), or a combination thereof.

Reference is made to FIGS. 2 and 3, and also to FIGS. 4A and 4B, which are schematic cross-sectional views of respective longitudinal portions of delivery shaft 30 and stent-graft 40, in accordance with an application of the present invention. For some applications, inner shaft 36 is shaped so as to define at least one conduit 50 therealong. Conduit 50 is shaped so as to define at least first and second non-longitudinally-overlapping enclosed longitudinal segments 52 and 54, each of which typically has a length of at least 5 mm. For some applications, the length of at least one of (e.g., both of) first and second enclosed longitudinal segments 52 and 54 is at least 10 mm, such as at least 20 mm, e.g., at least 30 mm. For example, the length of first enclosed longitudinal segment 52 may be at least 5 mm, and the length of second enclosed longitudinal segment 54 may be at least 10 mm, such as at least 20 mm, e.g., at least 30 mm. Conduit 50 is also shaped so as to define a restraining longitudinal portion 56 that is longitudinally disposed between first and second enclosed longitudinal segments 52 and 54. Restraining longitudinal portion 56 is typically non-enclosed.

For some applications, conduit 50 is not coaxial with inner shaft 36. In other words, the central longitudinal axis 57 of conduit 50 does not coincide with the central longitudinal axis 59 of inner shaft 36. As used in the present application, including in the claims, a "longitudinal central axis" of an elongate structure is the set of all centroids of cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.) For applications in which restraining longitudinal portion 56 is open, and thus cannot define any centroids in cross-section, the central longitudinal axis of restraining longitudinal portion 56 is defined by extending the central longitudinal axis of adjacent enclosed longitudinal segments 52 and 54 along restraining longitudinal portion 56.

For some applications, as labeled in FIG. 4B, a first distance D1 between central longitudinal axis 57 of conduit 50 and an external surface 61 of inner shaft 36 is no more than 0.1 mm, such as no more than 0.05 mm, and/or no more than 40% of a diameter D2 of inner shaft 36, such as no more than 20% of the diameter. Alternatively or additionally, for some applications, a second distance D3 between central longitudinal axis 57 of conduit 50 and central longitudinal axis 59 of inner shaft 36 is at least 0.1 mm, such as at least 0.5 mm, and/or at least 20% of diameter D2 of inner shaft 36, such as at least 40% of the diameter. The plurality of conduits 50 described hereinbelow may also be characterized by these parameters. Conduits 450 and/or 480, described hereinbelow with reference to FIGS. 11-12C, may also be characterized by these parameters.

For some applications, the inner shaft comprises polymer, such as a PEEK polymer. For some applications, the inner shaft, along with its bores (conduits 50 and guidewire bore 102, described hereinbelow), are manufactured by standard polymer extrusion technologies, using a custom-designed die (usually a disc with accurately machined openings in the shape of the non-bore sections, i.e., the bores' cross sections are masked in the die, so as to extrude no polymer in these portions of the tube). For some applications, the non-enclosed portions of the tube are formed by hand/machine removal of the thin tube's wall, using a scalpel/fine-drill, respectively.

Figure 6A:
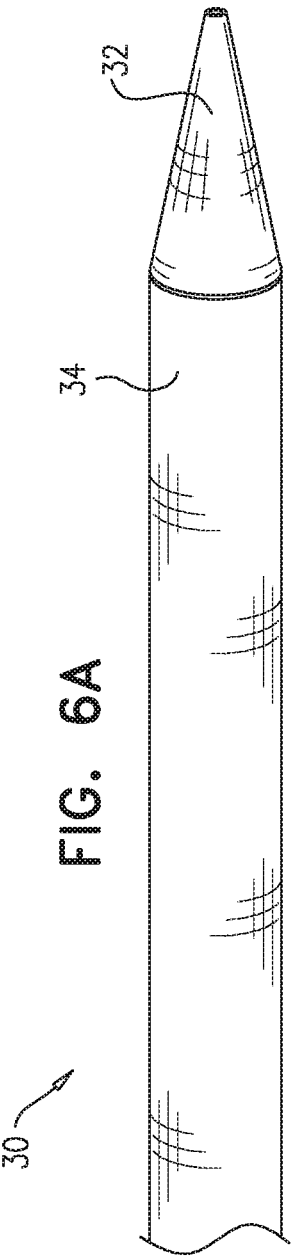
Figure 6B:
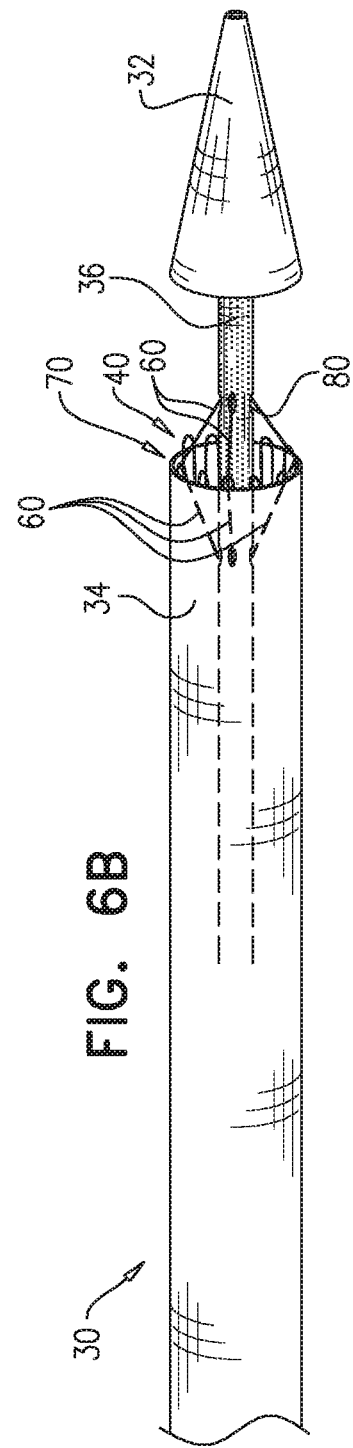
Figure 6E:
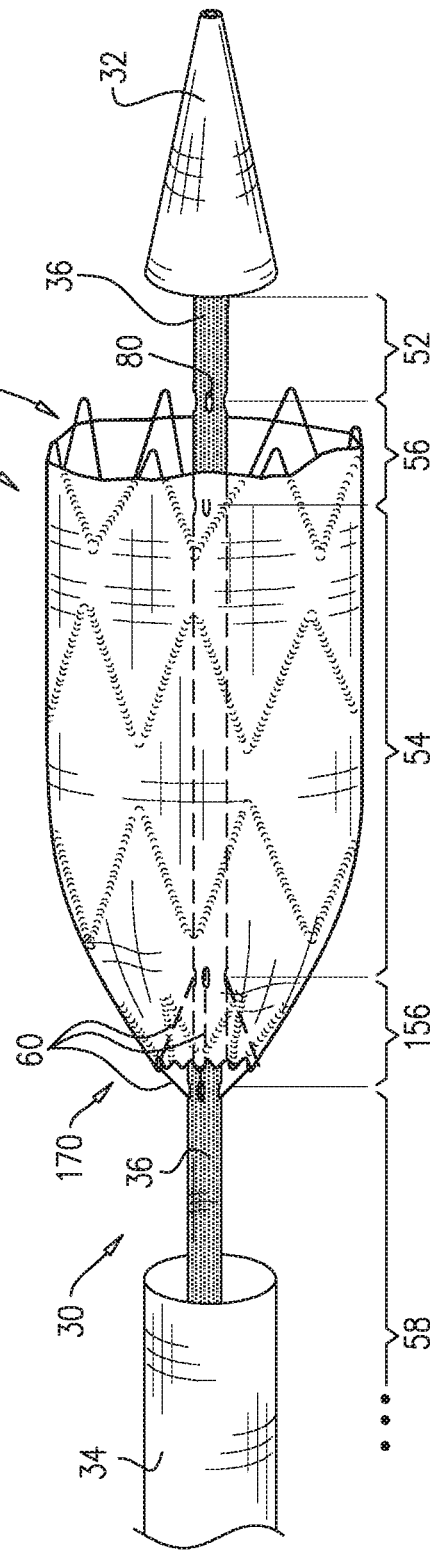
Figure 6F:
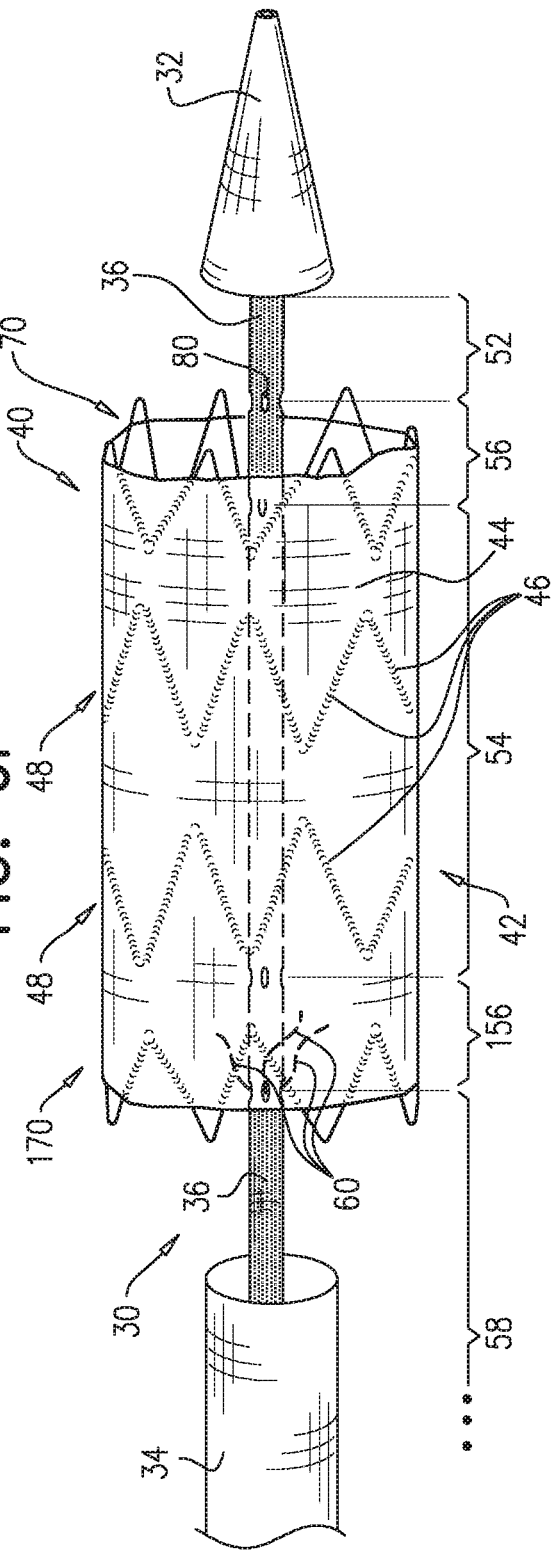

Deployment system 10 further comprises at least one restraining wire 60. Deployment system 10 is configured such that:

when restraining wire 60 is removably disposed in first and second enclosed longitudinal segments 52 and 54, such as shown in FIGS. 3 and 6A-D, a portion 62 of restraining wire 60 disposed alongside restraining longitudinal portion 56 of inner shaft 36 prevents full radial expansion of a longitudinal portion 70 of stent-graft 40 by physically engaging longitudinal portion 70 of stent-graft 40, and when restraining wire 60 has been withdrawn from at least first enclosed longitudinal segment 52 (and, optionally, from alongside restraining longitudinal portion 56), such as shown in FIGS. 6E-F, restraining wire 60 does not prevent the full radial expansion of longitudinal portion 70 of stent-graft 40.

(It is to be understood that when restraining wire 60 is removably disposed in first and second enclosed longitudinal segments 52 and 54, the restraining wire is not necessarily disposed along the entire lengths of the first and second enclosed longitudinal segments.)

Typically, a proximal portion 72 of restraining wire 60 is coupled to a withdrawal actuator 700 of control handle 20, such as described hereinbelow with reference to FIGS. 14A-E. Restraining wire 60 terminates at a free distal end 74 thereof, which is not fixed to delivery shaft 30, and is free to be proximally withdrawn from first enclosed longitudinal segment 52, and thus to free longitudinal portion 70 of stent-graft 40. Free distal end 74 of restraining wire 60 either (a) is disposed within first enclosed longitudinal segment 52, or (b) extends distally beyond first enclosed longitudinal segment 52. For example, the free distal end may extend into an interior of distal tip 32. First enclosed longitudinal segment 52 may or may not extend into the interior of distal tip 32. (It is to be understood that portion 62 of restraining wire 60 is not a fixed longitudinal portion of the wire. As the wire is withdrawn, a different longitudinal portion of the wire physically engages longitudinal portion 70 of stent-graft 40 at any given point in time, until longitudinal portion 70 is freed from the wire, at which point in time no portion of the wire physically engages longitudinal portion 70 of stent-graft 40.)

Typically, portion 62 of restraining wire 60 physically engages longitudinal portion 70 by passing through (e.g., being threaded through) one or more elements of longitudinal portion 70, as shown by way of example in the blow-up in FIG. 3. For some applications, portion 62 of restraining wire 60 physically engages at least one of structural stent elements 46 of longitudinal portion 70 of stent-graft 40. Typically, the at least one structural stent element physically engaged by restraining wire 60 itself provides structural support to stent-graft. In other words, the engaged element is not provided especially and only for being engaged by the restraining wire. Alternatively or additionally, for some applications, portion 62 of restraining wire 60 physically engages covering element 44 at longitudinal portion 70 of stent-graft 40.

Typically, restraining longitudinal portion 56 of inner shaft 36 has a length equal to less than 15% of a perimeter of longitudinal portion 70 of stent-graft 40, such as less than 5% of the perimeter, when the stent-graft is unconstrained in a fully radially-expanded state, i.e., no forces are applied to the stent-graft by deployment system 10 (such as outer sheath 34), walls of a blood vessel, or otherwise (including that no forces are applied to longitudinally-adjacent portions of the stent-graft, which forces would reduce the perimeter of longitudinal portion 70). Alternatively or additionally, for some applications, restraining longitudinal portion 56 of inner shaft 36 has a length of less than 20 mm, such as less than 10 mm, e.g., less than 5 mm. Alternatively or additionally, for some applications, restraining longitudinal portion 56 of inner shaft 36 has a length that is less than 150% of a perimeter of inner shaft 36, such as less than 100% of the perimeter, e.g., less than 50% of the perimeter (the perimeter is the circumference in configurations in which the inner shaft is circular in cross-section). Typically, the length of restraining longitudinal portion 56 is at least 15% of the perimeter of inner shaft 36, such as at least 30% of the perimeter. Alternatively or additionally, the length of restraining longitudinal portion 56 may be at least 1.5 mm, such as 3 mm. Typically, each of first and second enclosed longitudinal segments 52 and 54 has an inner diameter of no more than 3 mm, such as no more than 2, and/or of no more than 50% of the outer diameter of inner shaft 36, such as no more than 30% of the outer diameter.

Upon withdrawal of outer sheath 34, the radially-compressed self-expanding stent-graft's outwardly-directed radial force, at certain locations along and around the stent-graft, is now applied to restraining wire 60. The exposed portion of the restraining wire is short enough relative to its cross section, and hence is stiff enough, so as to act more like a restraining beam than a suturing filament. Therefore, the outwardly-directed radial force does not pull out the portion of restraining wire 60 disposed in first enclosed longitudinal segment 52, even though distal end 74 of restraining wire 60 is not fixed to delivery shaft 30, as mentioned above. The relatively small inner diameter of first and second enclosed longitudinal segments 52 and 54 also generally helps prevent restraining wire 60 from being prematurely pulled out of first enclosed longitudinal segment 52. The relatively short length of restraining longitudinal portion 56 enables restraining wire 60 to perform its restraining function, even though restraining wire 60 is still flexible enough to accommodate a tortuous path through the subject's vasculature during advancing of delivery shaft 30. In other words, if restraining longitudinal portion 56 were longer, restraining wire 60 would need to be so stiff that the restraining wire could not accommodate the tortuous path of the vasculature.

The flexibility of restraining wire 60 allows portion 62 of restraining wire 60 to extend outward from inner shaft 36, when restraining wire 60 is disposed in first and second enclosed longitudinal segments 52 and 54. As a result, restraining wire 60 engages longitudinal portion 70 of stent-graft 40 at one or more locations outside of inner shaft 36. This outward extension of the restraining wire allows restraining wire 60 to physically engage longitudinal portion 70 of stent-graft 40, without any elements of the stent-graft projecting into the interior of the inner shaft. As a result, the inner shaft may be provided with a relatively small diameter, such as no more than 4 mm, which enables the delivery shaft to have a small crossing profile when loaded with the stent-graft. Typically, deployment system 10, including delivery shaft 30 thereof, is configured such that a greatest distance of restraining wire 60 from the external surface of inner shaft 36 is no more than 1 mm, when portion 62 of restraining wire 60 engages longitudinal portion 70 of stent-graft 40, and the stent-graft is not otherwise constrained (such as by outer sheath 34 or the wall of the blood vessel).

Reference is still made to FIGS. 2, 3, and FIGS. 4A-B, and additionally to FIG. 4C, which is a highly schematic cross-sectional illustration of a portion of delivery shaft 30, a single restraining wire 60, and a single structural stent element 46 of a stent-graft, in accordance with an application of the present invention. Typically, restraining wire 60 is stiff enough to prevent full radial expansion of longitudinal portion 70 of stent-graft 40 when removably disposed in first and second enclosed longitudinal segments 52 and 54, even when there is no tensile stress in the restraining wire, i.e., when the wire is loose because no tensile force is applied to proximal portion 72 of the restraining wire, such as described hereinbelow with reference to FIGS. 14D, 15B, and 16B. This is possible both because of the stiffness of the restraining wire and the relatively short length of restraining longitudinal portion 56. As shown schematically in FIG. 4C, the force applied by a structural stent element 46 of a self-expanding stent-graft (and/or covering element 44 of the stent-graft, not shown in FIG. 4C) includes an outward force F directed outward from inner shaft 36. Restraining wire 60 is stiff enough to at least partially restrain structural stent element 46 from pulling sufficiently far from inner shaft 36 to allow full expansion of the stent-graft.

Typically, restraining wire 60 comprises a metal. Typically, in order for the restraining wire to function more like a restraining beam than a suturing filament, as described hereinabove, the restraining wire has a stiffness (moment of inertia) of at least 0.0002 $Mm^4$, and/or a Young's modulus of at least 60 GPa, such as at least 80 GPa. For some applications, restraining wire comprises a metal alloy, e.g., Nitinol, e.g., having a diameter of between 0.08 and 0.3 mm, such as 0.1 mm or 0.3 mm. For some applications, the Nitinol is "solid" tube. For applications in which the wire comprises Nitinol, the wire typically has a PTFE coating, so as to reduce friction with the wall of the conduit during withdrawal of the wire to release the stent-graft. For other applications, restraining wire 60 comprises stainless steel, such as flexible stainless steel, e.g., 440C stainless steel, e.g., having a diameter of between 0.08 and 0.3 mm, such as 0.1 mm. For some applications, the at least one restraining wire 60 is solid, while for other applications, the at least one restraining wire 60 is shaped so as to define one or more internal bores; for the example, the wire may comprise a plurality of strands, or may be shaped as a hollow tube.

For some applications, such as shown in FIGS. 2, 3, and 4A, conduit 50 is open along restraining longitudinal portion 56 of inner shaft 36. For example, as shown in these figures, inner shaft 36 may be shaped so as to define a longitudinal slit 76 along restraining longitudinal portion 56, such that conduit 50 is open along restraining longitudinal portion 56.

Reference is made to FIG. 5, which is a schematic illustration of another configuration of restraining longitudinal portion 56, in accordance with an application of the present invention. In this configuration, conduit 50 is shaped so as to define (a) a first opening 80 at a first longitudinal border between first enclosed longitudinal segment 52 and restraining longitudinal portion 56 of inner shaft 36, and (b) a second opening 82 at a second longitudinal border between second enclosed longitudinal segment 54 and restraining longitudinal portion 56 of inner shaft 36. Deployment system 10 is configured such that when restraining wire 60 is removably disposed in first and second enclosed longitudinal segments 52 and 54, restraining wire 60 passes through first and second openings 80 and 82. For example, first and second openings 80 and 82 may be circular. For some applications, deployment system 10 is configured such that when restraining wire 60 is removably disposed in first and second enclosed longitudinal segments 52 and 54, portion 62 of restraining wire 60, longitudinally between the first and the second openings, extends outward from inner shaft 36. Typically, but not necessarily, in this configuration restraining longitudinal portion 56 is not shaped so as to define any slots or slits therealong.

Reference is made to FIGS. 2, 3, and 5. For some applications, deployment system 10 further comprises first and second rings 90 and 92. First ring 90 is longitudinally fixed to and surrounds inner shaft 36 at a first longitudinal border between first enclosed longitudinal segment 52 and restraining longitudinal portion 56 of inner shaft 36, and second ring 92 is longitudinally fixed to and surrounds inner shaft 36 at a second longitudinal border between second enclosed longitudinal segment 54 and restraining longitudinal portion 56 of inner shaft 36. Rings 90 and 92 typically prevent inner shaft 36 from being damaged by restraining wire 60, which, as mentioned above, may be strong and thin. Inner shaft 36 may comprise a polymer, which might be torn by the restraining wire in the absence of the rings.

For some applications, first and second rings 90 and 92 comprise a radiopaque metal, such as tantalum. The radiopaque material enables the surgeon to visualize the ends of restraining longitudinal portion 56 during an implantation procedure, which may aid in the proper positioning of inner shaft 36 and stent-graft 40 during the procedure.

Reference is made to FIGS. 2-5. For some applications, inner shaft 36 is shaped so as to define a plurality of conduits 50 therealong. Conduits 50 are typically not coaxial with inner shaft 36, and are not coaxial with one another. For some applications, the plurality of conduits 50 are circumferentially evenly distributed around inner shaft 36. For example, if there are four conduits 50, the conduits may be distributed at 12 o'clock, 3 o'clock, 6 o'clock, and 9 o'clock. Conduits 50 are shaped so as to define respective first enclosed longitudinal segments 52 and respective second enclosed longitudinal segments 54. Typically, first enclosed longitudinal segments 52 longitudinally coincide with one another, and second enclosed longitudinal segments 54 longitudinally coincide with one another. Restraining longitudinal portion 56 of inner shaft 36 is longitudinally disposed between (a) first enclosed longitudinal segments 52 and (b) second enclosed longitudinal segments 54. Deployment system 10 comprises a plurality of restraining wires 60. Deployment system 10 is configured such that:

when restraining wires 60 are removably disposed in first enclosed longitudinal segments 52, respectively, and in second enclosed longitudinal segments 54, respectively, respective portions 62 of restraining wires 60 disposed alongside restraining longitudinal portion 56 of inner shaft 36 prevent the full radial expansion of longitudinal portion 70 of stent-graft 40 by physically engaging longitudinal portion 70 of stent-graft 40, and when restraining wires 60 have been withdrawn from at least first enclosed longitudinal segments 52, respectively (and, optionally, from alongside restraining longitudinal portion 56), restraining wires 60 do not prevent the full radial expansion of longitudinal portion 70 of stent-graft 40.

Typically, but not necessarily, a single one of the restraining wires is removably disposed in each of the first longitudinal segments and corresponding second longitudinal segment. Providing a separate conduit for each of the wires generally prevents restraining wires 60 from becoming entangled with one another, or pulling on one another, particularly when delivery shaft 30 is advanced along a tortuous path through the subject's vasculature. (It is to be understood that when restraining wire 60 is removably disposed in first enclosed longitudinal segments 52 and in second enclosed longitudinal segments 54, the restraining wire is not necessarily disposed along the entire lengths of the first and the second enclosed longitudinal segments.)

For example:
- the plurality of conduits 50 may comprise two, three, four (e.g., conduits 50A, 50B, 50C, and 50D), or more conduits,
- first enclosed longitudinal segments 52 may comprise two, three, or four (e.g., first enclosed longitudinal segments 52A, 52B, 52C, and 52D), or more first enclosed longitudinal segments,
- second enclosed longitudinal segments 54 may comprise two, three, or four (e.g., second enclosed longitudinal segments 54A, 54B, 54C, and 54D), or more second enclosed longitudinal segments, and
- restraining wires 60 may comprise two, three, or four (e.g., restraining wires 60A, 60B, 60C, and 60D), or more restraining wires 60.

Typically, respective proximal portions 72 of restraining wires 60 are coupled to withdrawal actuator 700 of control handle 20, such as described hereinbelow with reference to FIGS. 14A-E. Restraining wires 60 terminate at respective free distal ends 74 thereof, which are not fixed to delivery shaft 30, and are free to be proximally withdrawn from first enclosed longitudinal segments 52, and thus to free longitudinal portion 70 of stent-graft 40. Free distal ends 74 are not connected to one another. Free distal ends 74 of restraining wires 60 either (a) are disposed within first enclosed longitudinal segments 52, respectively, or (b) extend distally beyond first enclosed longitudinal segments 52, respectively. For example, the free distal ends may extend into an interior of distal tip 32. First enclosed longitudinal segments 52 may or may not extend into the interior of distal tip 32. (It is to be understood that portions 62 of restraining wires 60 are not fixed longitudinal portions of the wires. As the wires are withdrawn, different longitudinal portions of the wires physically engages longitudinal portion 70 of stent-graft 40 at any given point in time, until longitudinal portion 70 is freed from the wires, at which point in time no portions of the wires physically engage longitudinal portion 70 of stent-graft 40.)

Typically, restraining wires 60 are stiff enough to prevent full radial expansion of longitudinal portion 70 of stent-graft 40 when removably disposed in first enclosed longitudinal segments 52 and second enclosed longitudinal segments 54, even when there is no tensile stress in the restraining wires, i.e., when the wires are loose because no tensile force is applied to respective proximal portions 72 of the restraining wires, such as described hereinbelow with reference to FIGS. 14D, 15B, and 16B. This is possible both because of the stiffness of the restraining wire and the relatively short length of restraining longitudinal portion 56.

Reference is made to FIGS. 2 and 3. For some applications, deployment system 10 is configured to restrain more than one longitudinal portion of stent-graft 40, such as two, three, four, or more longitudinal portions. For example, longitudinal portion 70 of stent-graft 40 may be a first longitudinal portion 70 of stent-graft 40, restraining longitudinal portion 56 of inner shaft 36 may be a first restraining longitudinal portion 56, and portion 62 of restraining wire 60 may be a first portion 62 of restraining wire 60. Conduit 50 is shaped so as to further define (a) a third enclosed longitudinal segment 58, which does not longitudinally overlap first enclosed longitudinal segment 52 or second enclosed longitudinal segment 54, and (b) a second restraining longitudinal portion 156 that is longitudinally disposed between second and third enclosed longitudinal segments 54 and 58. Second restraining longitudinal portion 156 is typically non-enclosed. For some applications in which deployment system 10 is configured to restrain two longitudinal portions of stent-graft 40, second restraining longitudinal portion 156 reaches control handle 20. For applications in which deployment system 10 is configured to restrain more than one longitudinal portion of stent-graft 40, typically the proximal-most restraining longitudinal portion reaches control handle 20.

In this configuration, deployment system 10 is configured such that:

when restraining wire 60 is removably disposed in first, second, and third enclosed longitudinal segments 52, 54, and 58, a second restraining longitudinal portion 156 of restraining wire 60 disposed alongside second restraining longitudinal portion 156 of inner shaft 36 prevents full radial expansion of a second longitudinal portion 170 of stent-graft 40 by physically engaging second longitudinal portion 170 of stent-graft 40, and when restraining wire 60 has been withdrawn from at least second enclosed longitudinal segment 54 (and, optionally, from alongside second restraining longitudinal portion 156), restraining wire 60 does not prevent the full radial expansion of second longitudinal portion 170 of stent-graft 40.

(It is to be understood that when restraining wire 60 is removably disposed in first, second, and third enclosed longitudinal segments 52, 54, and 58, the restraining wire is not necessarily disposed along the entire lengths of the first, second, and third enclosed longitudinal segments.)

For some applications, a longitudinal distance between longitudinally-closest ends of first and second longitudinal portions 70 and 170 of stent-graft 40 equals at least 10% of an average of (a) a perimeter of first longitudinal portion 70 of stent-graft 40 and (b) a perimeter of second longitudinal portion 170 of stent-graft 40, such as least 20% of the average, when the stent-graft is unconstrained in a fully radially-expanded state, i.e., no forces are applied to the stent-graft by deployment system 10 (such as outer sheath 34), walls of a blood vessel, or otherwise (including that no forces are applied to longitudinally-adjacent portions of the stent-graft, which forces would reduce the perimeters of first and second longitudinal portions 70 and 170). Alternatively or additionally, for some applications, the longitudinal distance is at least 10 mm, such as at least 20 mm, e.g., at least 30 mm.

Typically, restraining wire 60 is stiff enough to prevent full radial expansion of first and second longitudinal portions 70 and 170 of stent-graft 40 when removably disposed in first, second, and third enclosed longitudinal segments 52, 54, and 58 even when there is no tensile stress in the restraining wire, i.e., when the wire is loose because no tensile force is applied to proximal portion 72 of the restraining wire, such as described hereinbelow with reference to FIGS. 14D, 15B, and 16B. This is possible both because of the stiffness of the restraining wire and the relatively short length of first and second restraining longitudinal portions 56 and 156.

Reference is made to FIGS. 1-5. For some applications, deployment system 10 is configured to be used with a guidewire 100. Inner shaft 36 is shaped so as to further define a bore 102 therethrough (labeled in FIGS. 4A-B), which is sized for passage of guidewire 100 therethrough. For some applications, as shown, bore 102 is concentrically disposed in inner shaft 36, coaxial with inner shaft 36. For some applications in which inner shaft 36 is shaped so as to define a plurality of conduits 50 therealong, such as described hereinabove with reference to FIGS. 2-5, the plurality of conduits 50 are circumferentially evenly distributed around bore 102. Typically, bore 102 has a greater diameter than that of each of conduits 50. Providing a separate bore for guidewire 100 generally prevents restraining wires 60 from becoming entangled with the bore, particularly when delivery shaft 30 is advanced along a tortuous path through the subject's vasculature.

Typically, each of conduits 50 is disposed at a constant angular location (or "o'clock") along inner shaft 36. Alternatively, respective portions of each of conduits 50 are disposed at different angular locations at different longitudinal locations along the inner shaft. For example, the angular location of a conduit may shift on opposite longitudinal sides of a restraining longitudinal portion.

For some applications in which a plurality of restraining wires 60 is provided, the restraining wires are removably positioned within differing numbers of conduits 50 at different longitudinal locations along inner shaft 36. For example, two restraining wires 60 may be positioned in two respective conduits 50 along second enclosed longitudinal segments 54, and in the same single conduit 50 along first enclosed longitudinal segment 52. In other words, the two restraining wires merge into a single conduit along first enclosed longitudinal segment 52. Similarly, four restraining wires 60 may be positioned in four respective conduits 50 along second enclosed longitudinal segments 54, and two of the wires may be positioned in a first single conduit along first enclosed longitudinal segment 52 and two of the wires may be positioned in a different single conduit along first enclosed longitudinal segment 52.

Reference is now made to FIGS. 6A-F, which are schematic illustrations of a deployment of stent-graft 40 from stent-graft deployment system 10, in accordance with an application of the present invention.

FIG. 6A shows delivery shaft 30 in an initial state, prior to deployment of the stent-graft. Outer sheath 34 is sized to hold stent-graft 40 in a first, highly radially-compressed state.

FIG. 6B shows delivery shaft 30 after outer sheath 34 has been partially withdrawn proximally, exposing first longitudinal portion 70 of stent-graft 40. Outer sheath 34 still holds stent-graft 40 in the first radially-compressed state.

FIG. 6C shows delivery shaft 30 after outer sheath 34 has been further partially withdrawn proximally, exposing an additional longitudinal portion of stent-graft 40. At this stage of deployment, outer sheath 34 no longer holds first longitudinal portion 70 of stent-graft in the first radially-compressed state, and allows partial radial expansion of first longitudinal portion 70 of stent-graft 40 to a second radially-compressed state in which first longitudinal portion 70 of stent-graft 40 is less radially compressed than in the first radially-compressed state. The at least one restraining wire 60 still prevents the full radial expansion of first longitudinal portion 70 of stent-graft 40 by physically engaging first longitudinal portion 70 of stent-graft 40.

FIG. 6D shows delivery shaft 30 after outer sheath 34 has been entirely proximally withdrawn from stent-graft 40. At this stage of deployment, outer sheath 34 no longer holds first longitudinal portion 70 or second longitudinal portion 170 of stent-graft 40 in first radially-compressed states, and allows partial radial expansion of both first and second longitudinal portions 70 and 170 of stent-graft 40 to second radially-compressed states in which the longitudinal portions are less radially compressed than in the first radially-compressed states. The at least one restraining wire 60 still prevents the full radial expansion of first and second longitudinal portions 70 and 170 of stent-graft 40. In addition, the at least one restraining wire 60 may also prevent the full radial expansion of a longitudinal portion of the stent-graft between the first and second longitudinal portions, depending on the ratio of (a) the longitudinal distance between longitudinally-closest ends of first and second longitudinal portions 70 and 170 to (b) the perimeter of the stent-graft. The smaller this ratio, the more the longitudinal portion of the stent-graft between the first and second longitudinal portions is restrained. If this ratio is large enough, at least part of the longitudinal portion of the stent-graft between the first and second longitudinal portions is not restrained at all.

FIG. 6E shows delivery shaft 30 after the at least one restraining wire 60 has been proximally withdrawn from first enclosed longitudinal segment 52 (and from alongside first restraining longitudinal portion 56). The at least one restraining wire 60 thus does not prevent the full radial expansion of first longitudinal portion 70 of stent-graft 40, which self-expands (typically, until expansion is at least partially inhibited by the wall of the blood vessel). At this stage of the deployment, the at least one restraining wire 60 is still removably disposed in second and third enclosed longitudinal segments 54 and 58, and thus continues to prevent the full radial expansion of second longitudinal portion 170 of stent-graft 40 by physically engaging second longitudinal portion 170.

FIG. 6F shows delivery shaft 30 after the at least one restraining wire 60 has been additionally proximally withdrawn from second enclosed longitudinal segment 54 (and from alongside second restraining longitudinal portion 156). The at least one restraining wire 60 thus does not prevent the full radial expansion of second longitudinal portion 170 of stent-graft 40, which self-expands (typically, until expansion is at least partially inhibited by the wall of the blood vessel).

Although conduits 50 are shown in FIGS. 6A-F as defining first and second openings 80 and 82, such as described hereinabove with reference to FIG. 5, conduits 50 may also be open along restraining longitudinal portion 56 of inner shaft 36, such as described hereinabove with reference to FIGS. 2, 3, and 4A.

Reference is now made to FIGS. 7A-C, which are schematic illustrations of two stages of a deployment of a stent-graft 140 from stent-graft deployment system 10, in accordance with an application of the present invention. These deployment techniques may be used in combination with other techniques described herein. Stent-graft 140 is the same as stent-graft 40, described hereinabove, except that stent-graft 140 (including at least a covering element 144 thereof) is shaped so as to define one or more lateral fenestrations, such as three lateral fenestrations 180, 182, and 184. For example, fenestrations 180 and 182 may be sized and disposed to allow blood flow to the renal arteries (such as by coupling to respective branching stent-grafts positioned in the renal arteries), and fenestration 184 may be sized and disposed to allow blood flow to the superior mesenteric artery (SMA) (such as by coupling to a branching stent-graft positioned in the SMA).

FIG. 7A shows delivery shaft 30 after outer sheath 34 has been entirely proximally withdrawn from stent-graft 140. At this stage of deployment, outer sheath 34 no longer holds first longitudinal portion 70 or second longitudinal portion 170 of stent-graft 140 in the first radially-compressed states, and allows partial radial expansion of both first and second longitudinal portions 70 and 170 of stent-graft 140 to second radially-compressed states in which the longitudinal portions are less radially compressed than in the first radially-compressed states. The at least one restraining wire 60 still prevents the full radial expansion of first and second longitudinal portions 70 and 170 of stent-graft 140, and, optionally, a longitudinal portion of the stent-graft between the first and second longitudinal portions, as explained above.

FIG. 7B shows delivery shaft 30 after the at least one restraining wire 60 has been proximally withdrawn from first enclosed longitudinal segment 52 (and from alongside first restraining longitudinal portion 56). The at least one restraining wire 60 thus does not prevent the full radial expansion of first longitudinal portion 70 of stent-graft 140, which self-expands (typically, until expansion is at least partially inhibited by the wall of the blood vessel). At this stage of the deployment, the at least one restraining wire 60 is still removably disposed in second and third enclosed longitudinal segments 54 and 58, and thus continues to prevent the full radial expansion of second longitudinal portion 170 of stent-graft 140 by physically engaging second longitudinal portion 170.

FIG. 7C shows delivery shaft 30 after the at least one restraining wire 60 has been additionally proximally withdrawn from second enclosed longitudinal segment 54 (and from alongside second restraining longitudinal portion 156). The at least one restraining wire 60 thus does not prevent the full radial expansion of second longitudinal portion 170 of stent-graft 140, which self-expands (typically, until expansion is at least partially inhibited by the wall of the blood vessel).

Although conduits 50 are shown in FIGS. 7A-C as defining first and second openings 80 and 82, such as described hereinabove with reference to FIG. 5, conduits 50 may also be open along restraining longitudinal portion 56 of inner shaft 36, such as described hereinabove with reference to FIGS. 2, 3, and 4A.

Reference is now made to FIGS. 8 and 9, which are schematic illustrations of alternative configurations of stent-graft 40 and stent-graft 140, respectively, in accordance with respective applications of the present invention. In these configurations, deployment system 10 is configured to restrain first and second longitudinal portions 70 and 170, as described hereinabove, and additionally is configured to prevent full radial expansion of a third longitudinal portion 270 of the stent-grafts by physically engaging third longitudinal portion 270 of the stent-grafts, and when restraining wire 60 has been withdrawn from at least a second enclosed longitudinal segment immediately distal to third longitudinal portion 270 (and, optionally, from alongside a third restraining longitudinal portion), the restraining wire does not prevent the full radial expansion of third longitudinal portion 270 of the stent-grafts.

For some applications, third longitudinal portion 270 is longitudinally disposed between first and second longitudinal portions 70 and 170, as shown in FIGS. 8 and 9. For some of these applications, a longitudinal distance between longitudinally-closest ends of first and third longitudinal portions 70 and 270 of the stent-graft equals at least 10% of an average of (a) a perimeter of first longitudinal portion 70 of the stent-graft and (b) a perimeter of third longitudinal portion 270 of the stent-graft, such as least 20% of the average, when the stent-graft is unconstrained in a fully radially-expanded state, i.e., no forces are applied to the stent-graft by deployment system 10 (such as outer sheath 34), walls of a blood vessel, or otherwise (including that no forces are applied to longitudinally-adjacent portions of the stent-graft, which forces would reduce the perimeters of first and third longitudinal portions 70 and 270). Alternatively or additionally, for some applications, the longitudinal distance between longitudinally-closest ends of first and third longitudinal portions 70 and 270 of the stent-graft is at least 10 mm, such as at least 20 mm, e.g., at least 30 mm. Alternatively or additionally, for some applications, a longitudinal distance between longitudinally-closest ends of third and second longitudinal portions 270 and 170 of the stent-graft equals at least 10% of an average of (a) a perimeter of second longitudinal portion 270 of the stent-graft and (b) a perimeter of second longitudinal portion 270 of the stent-graft, such as least 20% of the average, when the stent-graft is unconstrained in a fully radially-expanded state, i.e., no forces are applied to the stent-graft by deployment system 10 (such as outer sheath 34), walls of a blood vessel, or otherwise (including that no forces are applied to longitudinally-adjacent portions of the stent-graft, which forces would reduce the perimeters of third and second longitudinal portions 270 and 170). Alternatively or additionally, for some applications, the longitudinal distance between longitudinally-closest ends of third and second longitudinal portions 270 and 170 of the stent-graft is at least 10 mm, such as at least 20 mm, e.g., at least 30 mm.

Although conduits 50 are shown in FIGS. 8 and 9 as defining first and second openings 80 and 82, such as described hereinabove with reference to FIG. 5, conduits 50 may also be open along restraining longitudinal portion 56 of inner shaft 36, such as described hereinabove with reference to FIGS. 2, 3, and 4A.

Reference is now made to FIGS. 10A-G, which are schematic illustrations of an exemplary method of using stent-graft deployment system 10, described hereinabove with reference to FIGS. 1-6F and 8, to deploy stent-graft 40, described hereinabove with reference to FIGS. 1-6F and 8, in the vicinity of a sub-renal (e.g., juxtarenal) abdominal aortic aneurysm 310 of an abdominal aorta, in accordance with an application of the present invention. Stent-graft deployment system 10 may also be used to treat a blood vessel suffering from a dissection.

As shown in FIG. 10A, during a first stage of the implantation procedure, guidewire 100 is transvascularly (typically percutaneously) advanced into the aorta e.g., via one of iliac arteries 314A or 314B.

As shown in FIG. 10B, delivery shaft 30 is transvascularly (typically percutaneously) advanced into the aorta e.g., via one of iliac arteries 314A or 314B, while stent-graft 40 is held in its first, highly radially-compressed state within outer sheath 34. In this exemplary deployment, delivery shaft 30 and distal tip 32 are advanced over guidewire 100 until the distal tip is positioned at or slightly above renal arteries 312A and 312B. Typically, during advancement of delivery shaft 30 (including inner shaft 36) through blood vessels, little or no tensile force (e.g., less than 10 N of tensile force, such as zero N of tensile force) is applied to proximal portion(s) 72 of restraining wire(s) 60, such that the restraining wire(s) are loose, such as described hereinbelow with reference to FIG. 14D. If the restraining wires were instead held taut during advancement of delivery shaft 30, this would reduce the flexibility of the delivery system when advancing through tortuous blood vessels.

As shown in FIG. 10C, outer sheath 34 is partially withdrawn proximally, releasing a longitudinal portion of stent-graft 40, including first longitudinal portion 70 of the stent-graft. At this stage of deployment, outer sheath 34 no longer holds first longitudinal portion 70 of stent-graft in the first radially-compressed state, and allows partial radial expansion of first longitudinal portion 70 of stent-graft 40 to a second radially-compressed state in which first longitudinal portion 70 of stent-graft 40 is less radially compressed than in the first radially-compressed state. The at least one restraining wire 60 still prevents the full radial expansion of first longitudinal portion 70 of stent-graft 40 by physically engaging first longitudinal portion 70 of stent-graft 40.

FIG. 10D shows delivery shaft 30 and stent-graft 40 after outer sheath 34 has been further withdrawn proximally, releasing more of the stent-graft.

FIG. 10E shows delivery shaft 30 and stent-graft 40 after outer sheath 34 has been entirely proximally withdrawn from stent-graft 40. At this stage of deployment, outer sheath 34 no longer holds first longitudinal portion 70 or second longitudinal portion 170 of stent-graft 40 in first radially-compressed states, and allows partial radial expansion of both first and second longitudinal portions 70 and 170 to second radially-compressed states in which the longitudinal portions are less radially compressed than in the first radially-compressed states. The at least one restraining wire 60 still prevents the full radial expansion of first and second longitudinal portions 70 and 170 of stent-graft 40, and, optionally, a longitudinal portion of the stent-graft between the first and second longitudinal portions, as explained above.

FIG. 10F shows delivery shaft 30 after the at least one restraining wire 60 has been proximally withdrawn from (a) first enclosed longitudinal segment 52 (and from alongside first restraining longitudinal portion 56), and (b) second enclosed longitudinal segment 54 (but not from alongside second restraining longitudinal portion 156). The at least one restraining wire 60 thus does not prevent the full radial expansion of first or second longitudinal portions 70 and 170 of stent-graft 40, which self-expands until expansion is at least partially inhibited by the wall of the aorta. Typically, until the withdrawal of the at least one restraining wire, little or no tensile force (e.g., less than 10 N of tensile force, such as zero N of tensile force) is applied to the proximal portion of the at least one restraining wire, such that the at least one restraining wire is loose, such as described hereinbelow with reference to FIG. 14D.

Thereafter, as shown in FIG. 10G, the surgeon withdraws the delivery shaft and guidewire from the vasculature, leaving stent-graft 40 implanted in the aorta.

Although conduits 50 are shown in FIGS. 10C-F as defining first and second openings 80 and 82, such as described hereinabove with reference to FIG. 5, conduits 50 may also be open along restraining longitudinal portion 56 of inner shaft 36, such as described hereinabove with reference to FIGS. 2, 3, and 4A.

Figure 11:
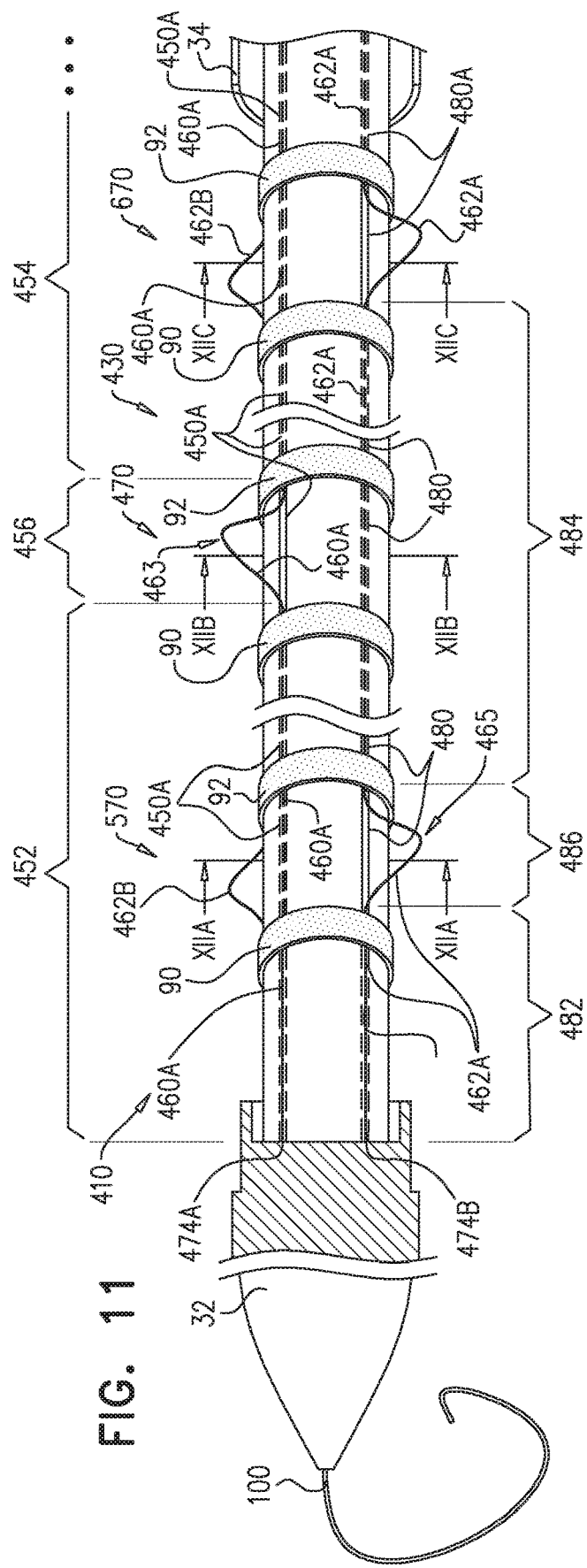
FIG. 11 is a schematic illustration of a distal portion of a delivery shaft of another stent-graft deployment system, in accordance with an application of the present invention.

Reference is now made to FIG. 11, which is a schematic illustration of a distal portion of a delivery shaft 430 of a stent-graft deployment system 410, and to FIGS. 12A-C, which are schematic cross-sectional views of respective longitudinal portions of delivery shaft 430 and stent-graft 40, in accordance with an application of the present invention. Except as described below, deployment system 410 and delivery shaft 430 are the same as deployment system 10 and delivery shaft 30 described hereinabove, and may implement any of the features of deployment system 10 and/or delivery shaft 30. Deployment system 10 and delivery shaft 30 may likewise implement any of the features of deployment system 410 and delivery shaft 430 in combination with all or a subset of the features of deployment system 410 and delivery shaft 430 described hereinabove. For clarity of illustration, stent-graft 40 is not shown in FIG. 11; however, stent-graft 40 is provided and initially disposed as illustrated in FIG. 3, mutatis mutandis, and as described hereinbelow with reference to FIGS. 13A-J.

Deployment system 410 is configured to enable controlled separate deployment of two or more longitudinal portions of stent-graft 40, not necessarily in the order in which the longitudinal portions are disposed along the stent-graft. Deployment system 410 comprises:

- at least one first restraining wire 460, which (a) when removably disposed in physical engagement with a first longitudinal portion 470 of stent-graft 40, prevents full radial expansion of first longitudinal portion 470, and (b) does not engage a second longitudinal portion 570 of stent-graft 40, which second longitudinal portion 570 does not longitudinally overlap first longitudinal portion 470; and
- at least one second restraining wire 462, which (a) when removably disposed in physical engagement with second longitudinal portion 570 of stent-graft 40, prevents full radial expansion of second longitudinal portion 570, and (b) does not engage first longitudinal portion 470 of stent-graft 40.

For example, the at least one first restraining wire 460 may comprise first restraining wires 460A and 460B (as shown in FIGS. 11 and 12A-C), or three or more first restraining wires 460 (configuration not shown), and the at least one second restraining wire 462 may comprise second restraining wires 462A and 462B (as shown in FIGS. 11 and 12A-C), or three or more second restraining wires 462 (configuration not shown). (As mentioned above, for clarity of illustration stent-graft 40 is not shown in FIG. 11; the longitudinal locations of first and second longitudinal portions 470 and 570 (as well as a third longitudinal portion 670, described below) are nevertheless labeled; these longitudinal portions are to be understood as being of the stent-graft, and not delivery shaft 430.)

During a deployment procedure, either the at least one first restraining wire 460 or the at least one second restraining wire 462 is first proximally withdrawn, depending on whether it is desired to first allow full radial expansion of first longitudinal portion 470, or of second longitudinal portion 570. After (e.g., at least one second after) the at least one first restraining wire 460 or the at least one second restraining wire 462 is at least partially withdrawn, the other of the at least one restraining wires is withdrawn. For some applications, a first subset of the restraining wires, which includes the at least one first restraining wire 460, is withdrawn, and, thereafter, a second subset of the restraining wires, which includes the at least one second restraining wire 462, is withdrawn. Alternatively, for some applications, a second subset of the restraining wires, which includes the at least one second restraining wire 462, is withdrawn, and, thereafter, a first subset of the restraining wires, which includes the at least one first restraining wire 460, is withdrawn. In either case, the second subset is different from the first subset.

For some applications, as shown in FIG. 11, first longitudinal portion 470 is proximal to second longitudinal portion 570, i.e., closer to control handle 20. In other words, first longitudinal portion 470 is disposed in a direction (i.e., proximal) with respect to second longitudinal portion 570, and first and second restraining wires 460 and 462 are withdrawn in this same direction (i.e., proximally). For other applications, second longitudinal portion 570 is proximal to first longitudinal portion 470, i.e., closer to control handle 20 (configuration not shown, but similar to the relationship between first longitudinal portion 470 and third longitudinal portion 670, described hereinbelow and shown in FIG. 11).

Typically, an inner shaft 436 of delivery shaft 430 is shaped so as to define at least one first conduit 450 therealong. For example, the at least one first conduit 450 may comprise first conduits 450A and 450B (as shown in FIGS. 11 and 12A-C), or three or more first conduits 450 (configuration not shown). The at least one first conduit 450 is shaped so as to define at least first and second non-longitudinally-overlapping enclosed longitudinal segments 452 and 454, each of which typically has a length of at least 5 mm. For some applications, the length of at least one of (e.g., both of) first and second enclosed longitudinal segments 452 and 454 is at least 10 mm, such as at least 20 mm, e.g., at least 30 mm. The at least one first conduit 450 is also shaped so as to define a first restraining longitudinal portion 456 that is longitudinally disposed between first and second enclosed longitudinal segments 452 and 454. First restraining longitudinal portion 456 is typically non-enclosed.

Typically, inner shaft 436 of delivery shaft 430 is also shaped so as to define at least one second conduit 480 therealong. For example, the at least one second conduit 480 may comprise second conduits 480A and 480B (as shown in FIGS. 11 and 12A-C), or three or more second conduits 480 (configuration not shown). The at least one second conduit 480 is shaped so as to define at least third and fourth non-longitudinally-overlapping enclosed longitudinal segments 482 and 484, each of which typically has a length of at least 5 mm. For some applications, the length of at least one of (e.g., both of) third and fourth enclosed longitudinal segments 482 and 484 is at least 10 mm, such as at least 20 mm, e.g., at least 30 mm. For example, the length of third enclosed longitudinal segment 482 may be at least 5 mm, and the length of fourth enclosed longitudinal segment 484 may be at least 10 mm, such as at least 20 mm, e.g., at least 30 mm. The at least one second conduit 480 is also shaped so as to define a second restraining longitudinal portion 486 that is longitudinally disposed between third and fourth enclosed longitudinal segments 482 and 484, and does not longitudinally overlap first restraining longitudinal portion 456. Second restraining longitudinal portion 486 is typically non-enclosed.

First and second restraining longitudinal portions 456 and 486 typically do not longitudinally overlap each other. For some applications, a longitudinal distance between longitudinally-closest ends of first and second restraining longitudinal portions 456 and 486 is at least 10 mm, such as at least 30 mm. Typically, first restraining longitudinal portion 456 at least partially longitudinally overlaps one of third and fourth enclosed longitudinal segments 482 and 484 (by way of example, in FIG. 11 first restraining longitudinal portion 456 is shown partially longitudinally overlapping fourth enclosed longitudinal segment 484). Typically, second restraining longitudinal portion 486 at least partially longitudinally overlaps one of first and second enclosed longitudinal segments 452 and 454 (by way of example, in FIG. 11 second restraining longitudinal portion 486 is shown partially longitudinally overlapping first enclosed longitudinal segment 452).

Inner shaft 436 may have the outer diameters set forth hereinabove for inner shaft 36, and first and second enclosed longitudinal segments 452 and 454 and/or third and fourth enclosed longitudinal segments 482 and 484 may have the inner diameters set forth hereinabove for enclosed longitudinal segments 52 and 54.

The at least one first conduits 450 and the at least one second conduit 480 are typically not coaxial with inner shaft 36, and are not coaxial with one another. For applications in which restraining longitudinal portion 456 is open, and thus cannot define any centroids in cross-section, the central longitudinal axis of restraining longitudinal portion 456 is defined by extending the central longitudinal axis of adjacent enclosed first and second longitudinal segments 452 and 454 along restraining longitudinal portion 456. Similarly, for applications in which restraining longitudinal portion 486 is open, and thus cannot define any centroids in cross-section, the central longitudinal axis of restraining longitudinal portion 486 is defined by extending the central longitudinal axis of adjacent enclosed third and fourth enclosed longitudinal segments 482 and 484 along restraining longitudinal portion 486.

Figure 13B:
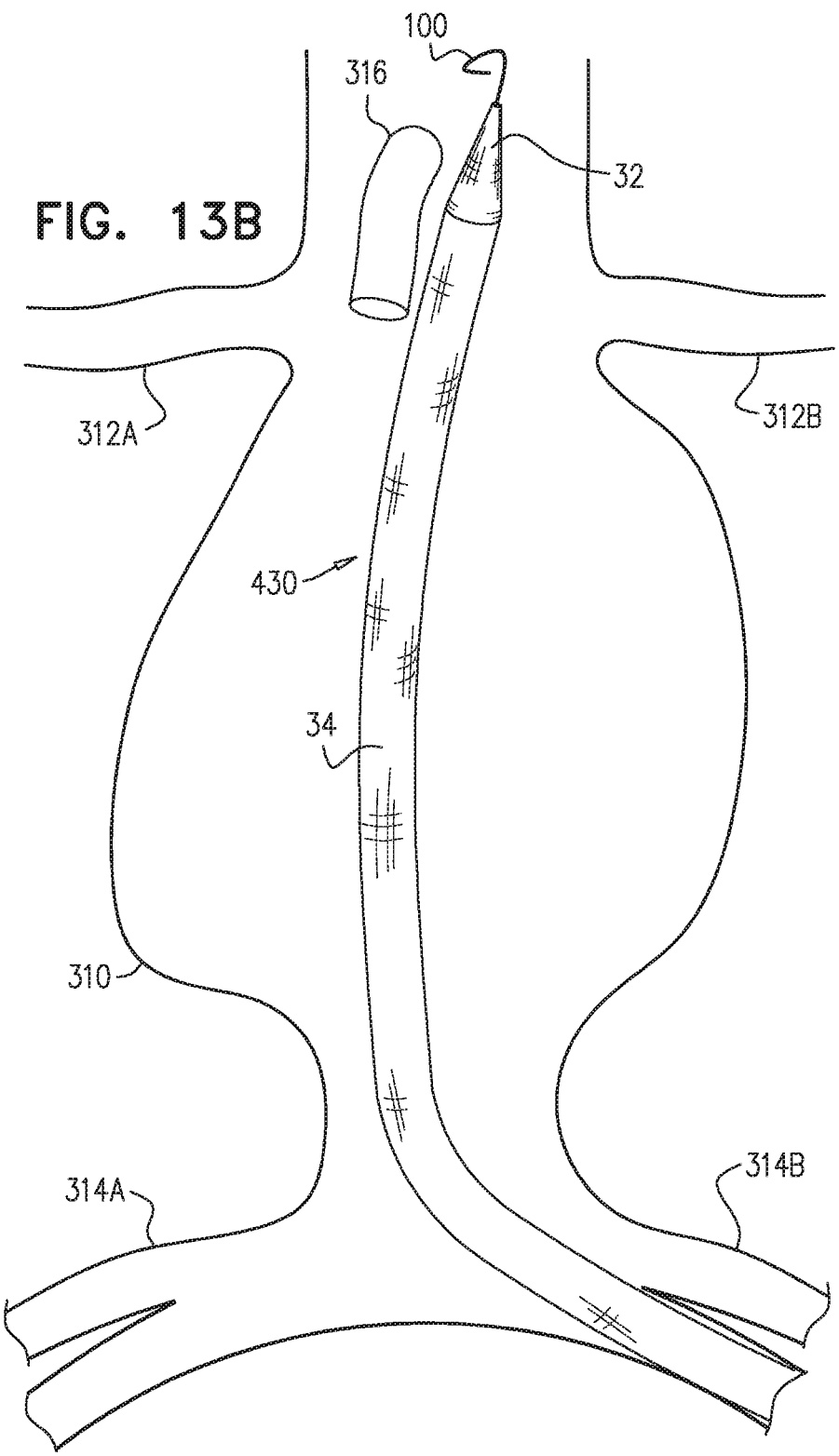
Figure 13C:
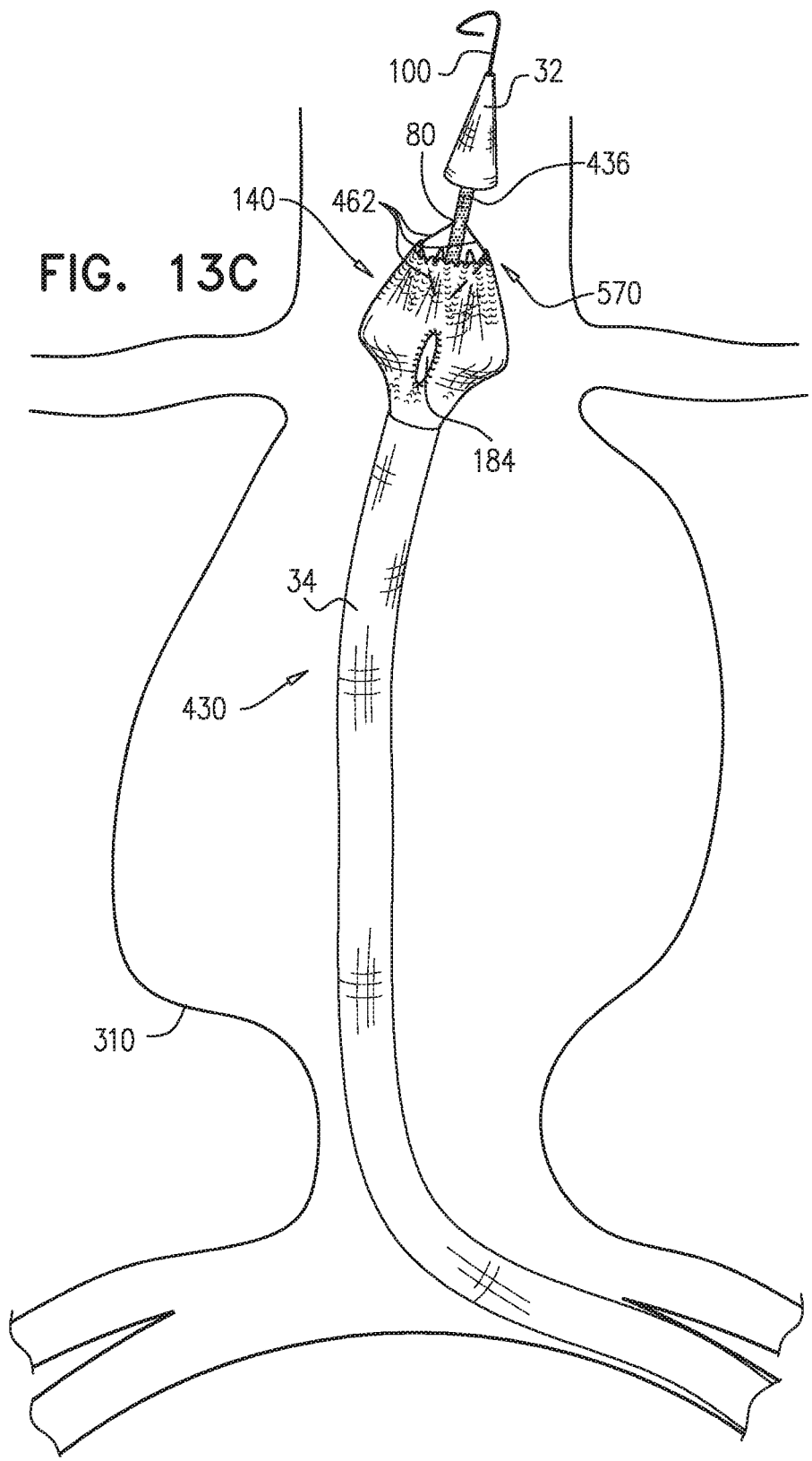
Figure 13D:
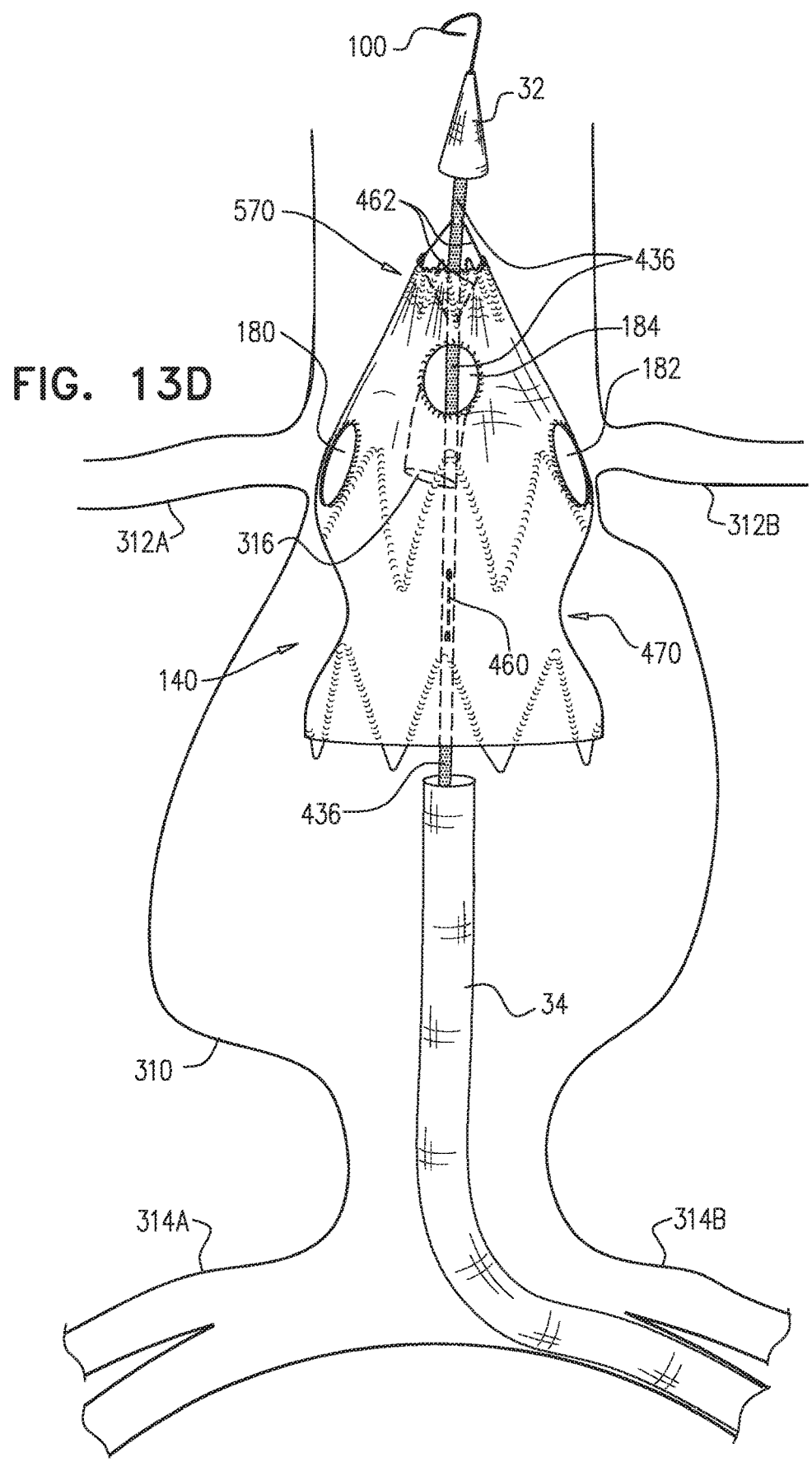
Figure 13E:
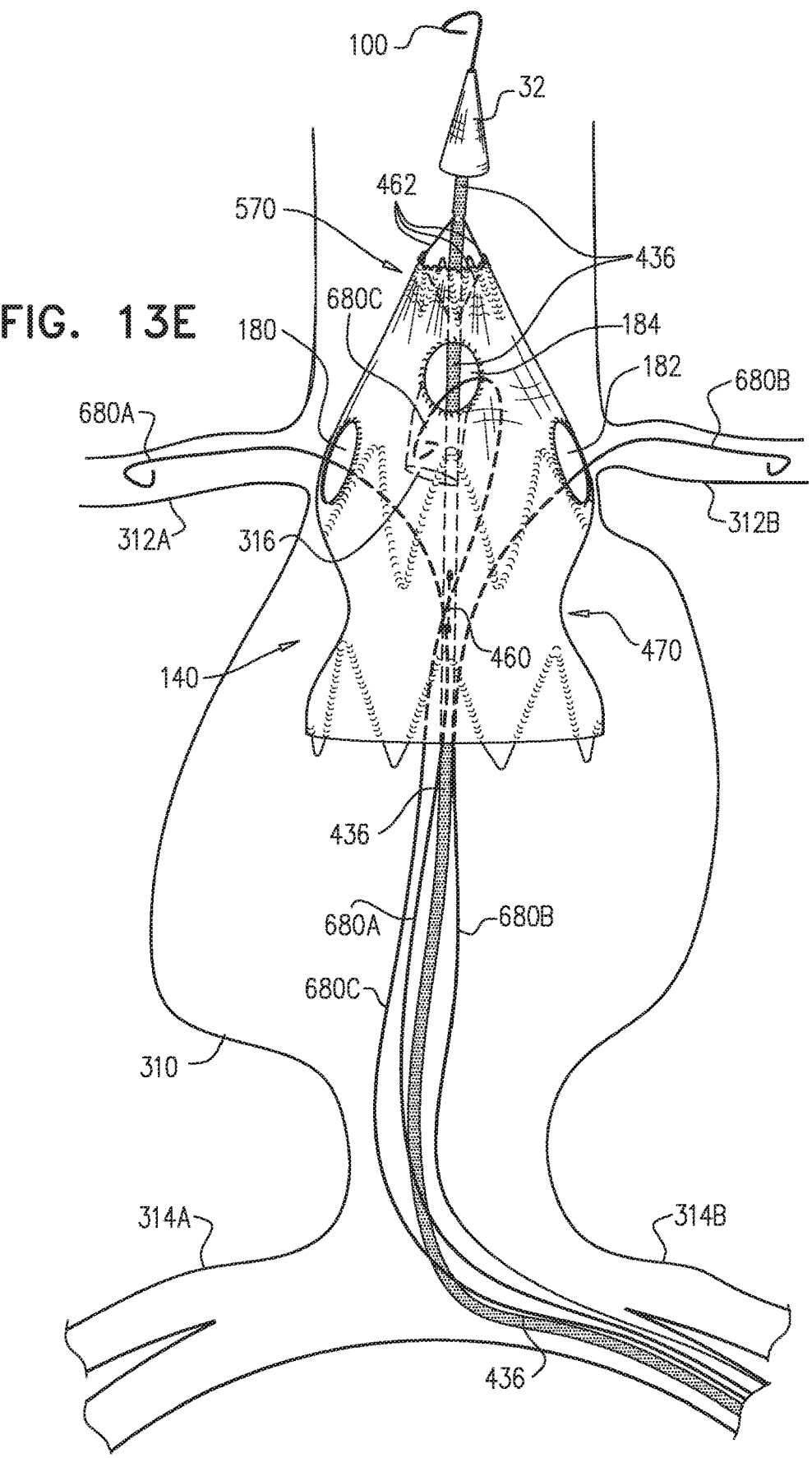
Figure 13F:
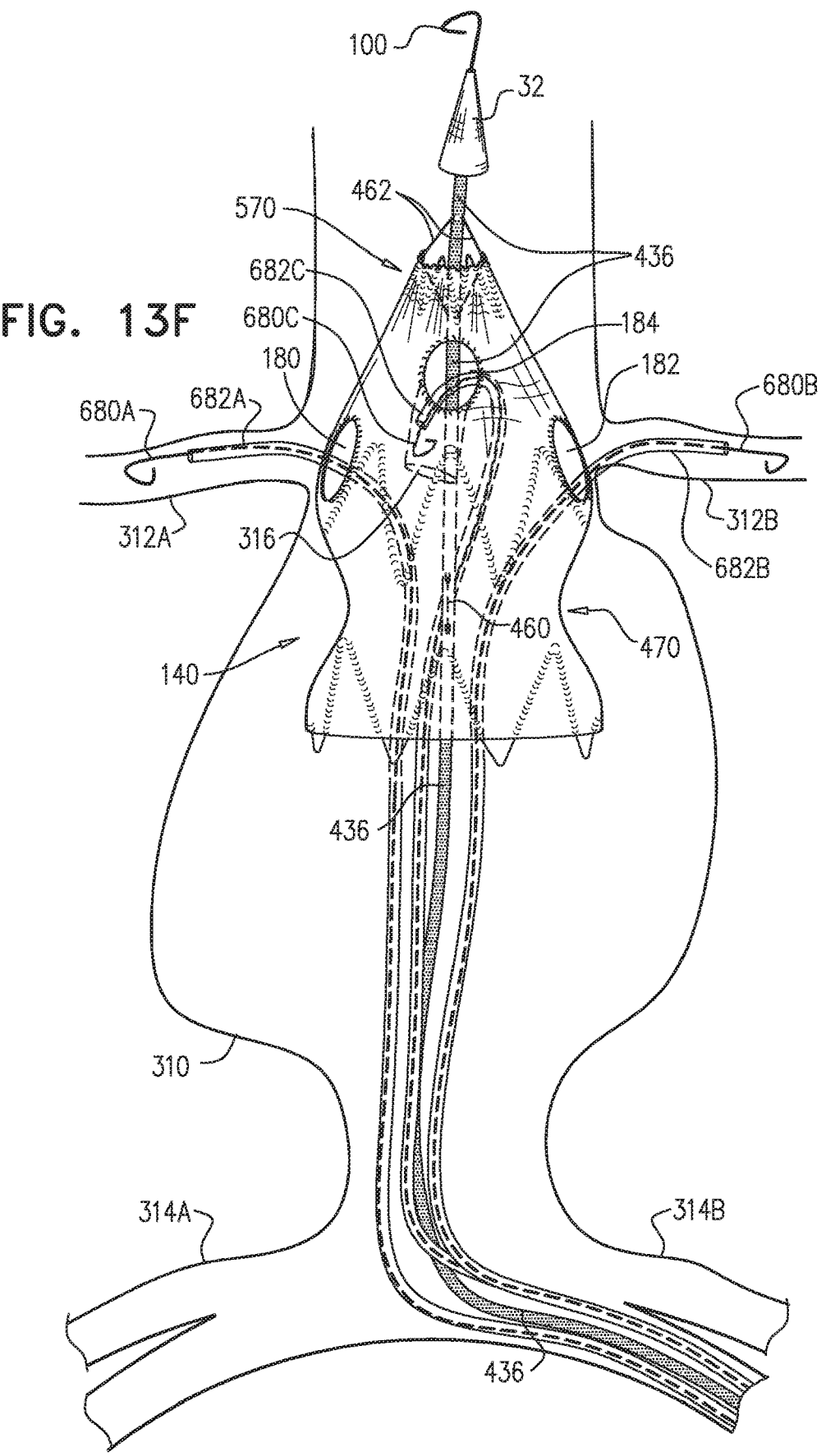
Figure 13G:
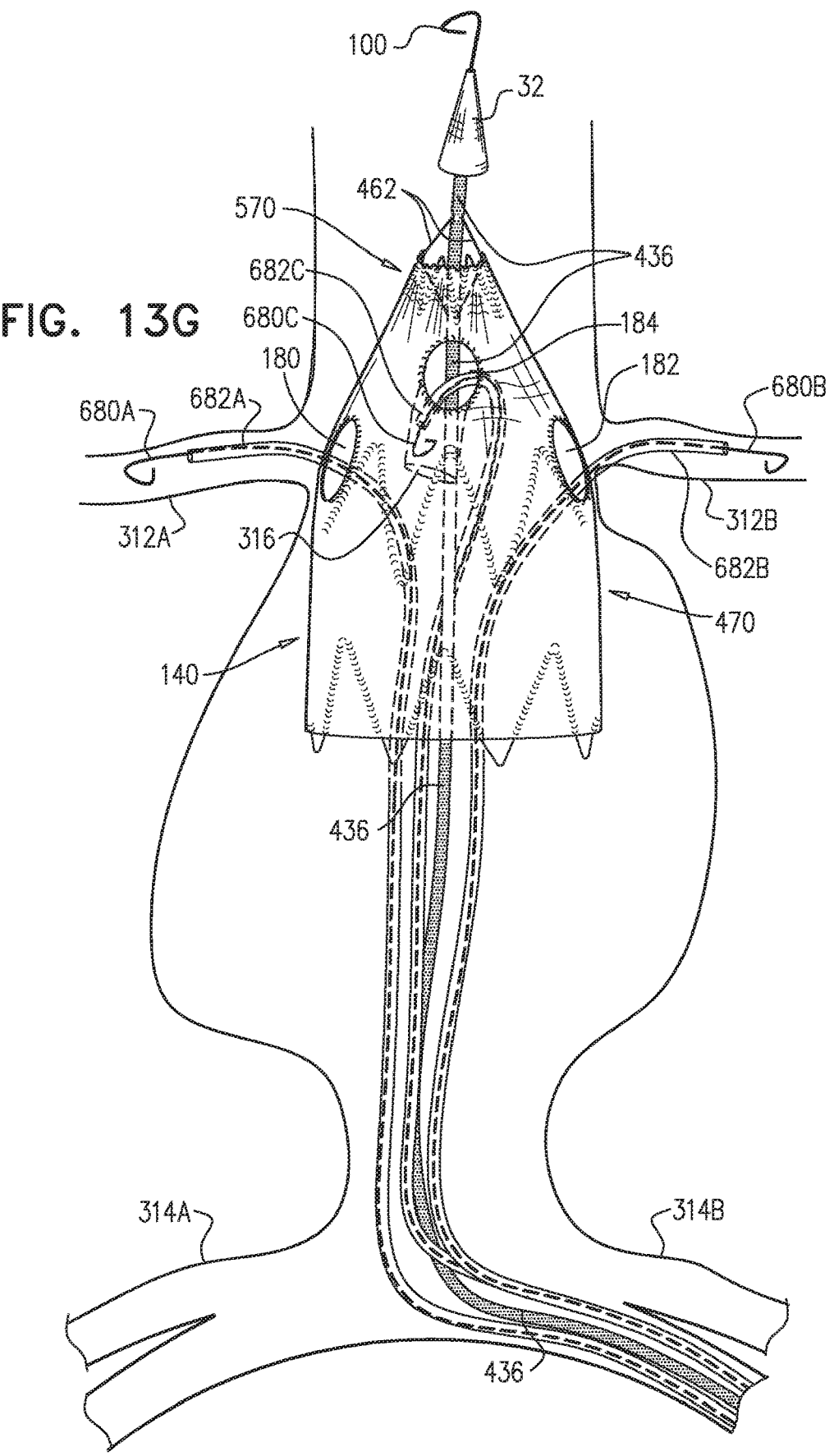
Figure 13H:
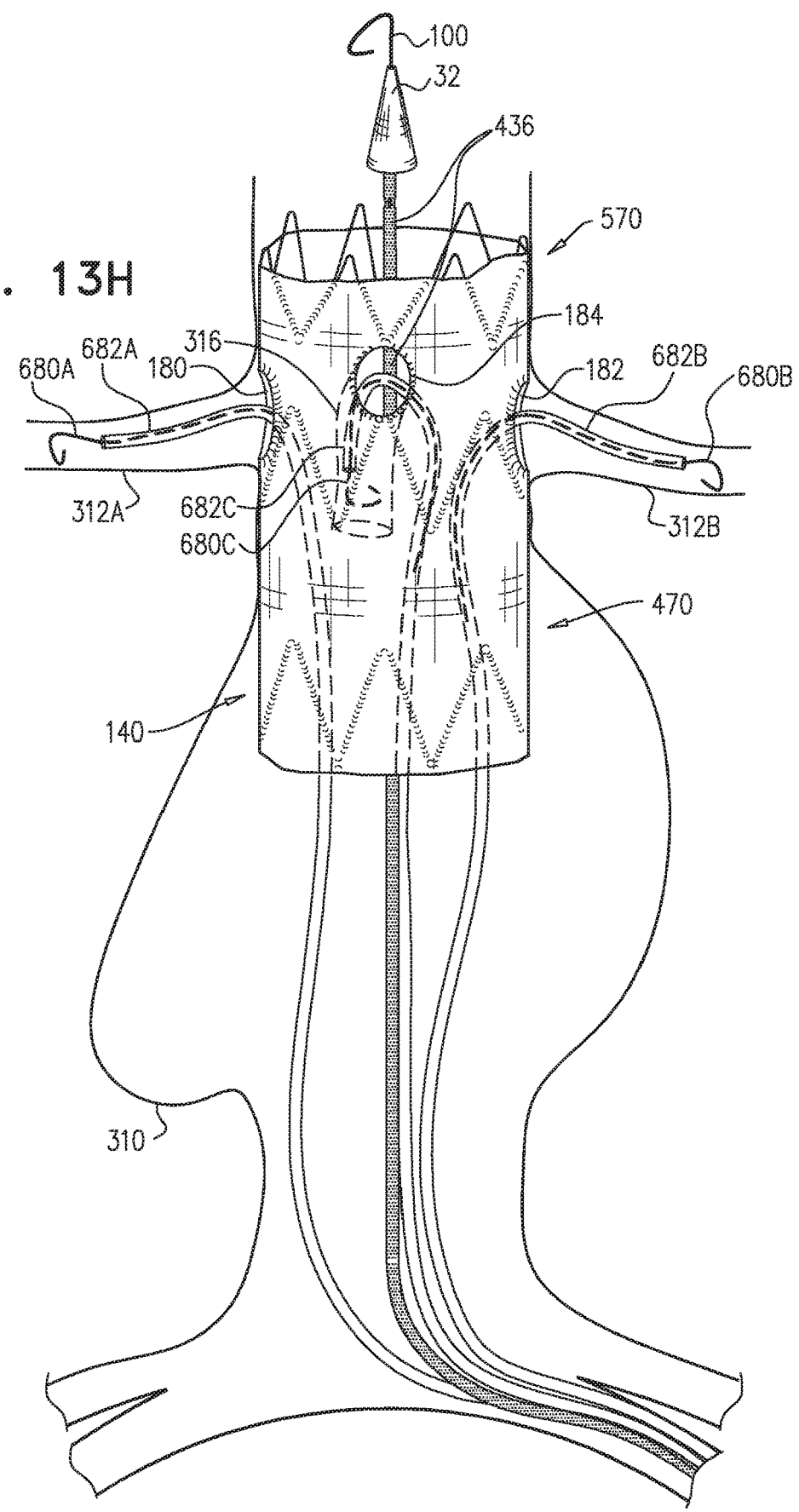

Typically, deployment system 410 is configured such that:
when the at least one restraining wire 460 is removably disposed in first and second enclosed longitudinal segments 452 and 454, such as shown in FIGS. 11, 12A-C, and 13D-F, a portion 463 of restraining wire 460 disposed alongside first restraining longitudinal portion 456 of inner shaft 436 prevents full radial expansion of first longitudinal portion 470 of stent-graft 40 by physically engaging first longitudinal portion 470 of stent-graft 40,
when the at least one restraining wire 460 has been withdrawn from at least first enclosed longitudinal segment 452 (and, optionally, from alongside first restraining longitudinal portion 456), such as shown in FIG. 13G, restraining wire 460 does not prevent the full radial expansion of first longitudinal portion 470 of stent-graft 40,
when the at least one second restraining wire 462 is removably disposed in third and fourth enclosed longitudinal segments 482 and 484, such as shown in FIGS. 11, 12A-C, and 13C-G, a portion 465 of second restraining wire 462 disposed alongside second restraining longitudinal portion 486 of inner shaft 436 prevents full radial expansion of second longitudinal portion 570 of stent-graft 40 by physically engaging second longitudinal portion 570 of stent-graft 40, and
when the at least one second restraining wire 462 has been withdrawn from at least third enclosed longitudinal segment 482 (and, optionally, from alongside second restraining longitudinal portion 486), such as shown in FIG. 13H, second restraining wire 462 does not prevent the full radial expansion of second longitudinal portion 570 of stent-graft 40.

(It is to be understood that when the at least one first restraining wire 460 is removably disposed in first and second enclosed longitudinal segments 452 and 454, the at least one restraining wire is not necessarily disposed along the entire lengths of the first and second enclosed longitudinal segments, and when the at least one second restraining wire 462 is removably disposed in third and fourth enclosed longitudinal segments 482 and 484, the at least one second restraining wire is not necessarily disposed along the entire lengths of the third and fourth enclosed longitudinal segments.)

Typically, a proximal portion 472A of the at least one first restraining wire 460 is coupled to a first withdrawal actuator 800 of control handle 20, such as described hereinbelow with reference to FIGS. 15A-B. A distal end 474A of the at least one first restraining wire 460 is not fixed to delivery shaft 430, and is free to be proximally withdrawn from first enclosed longitudinal segment 452, and thus to free first longitudinal portion 470 of stent-graft 40. Typically, a proximal portion 472B of the at least one second restraining wire 462 is coupled to a second withdrawal actuator 802 of control handle 20, such as described hereinbelow with reference to FIGS. 15A-B. A distal end 474B of the at least one second restraining wire 462 is not fixed to delivery shaft 430, and is free to be proximally withdrawn from third enclosed longitudinal segment 482, and thus to free second longitudinal portion 570 of stent-graft 40.

For some applications, a longitudinal distance between longitudinally-closest ends of first and second longitudinal portions 470 and 570 of stent-graft 40 equals at least 10% of an average of (a) a perimeter of first longitudinal portion 470 of stent-graft 40 and (b) a perimeter of second longitudinal portion 570 of stent-graft 40, such as least 20% of the average, when the stent-graft is unconstrained in a fully radially-expanded state, i.e., no forces are applied to the stent-graft by deployment system 410 (such as outer sheath 34), walls of a blood vessel, or otherwise (including that no forces are applied to longitudinally-adjacent portions of the stent-graft, which forces would reduce the perimeters of first and second longitudinal portions 470 and 570). Alternatively or additionally, for some applications, the longitudinal distance is at least 10 mm, such as at least 20 mm, e.g., at least 30 mm.

For some applications, the at least one second restraining wire 462, when removably disposed in physical engagement with third longitudinal portion 670 of stent-graft 40, prevents full radial expansion of third longitudinal portion, and the at least one first restraining wire 460 does not engage third longitudinal portion 670 of stent-graft 40. Third longitudinal portion 670 does not longitudinally overlap first or second longitudinal portions 470 and 570, and first longitudinal portion 470 is longitudinally disposed between second and third longitudinal portions 570 and 670.

Reference is now made to FIGS. 13A-J, which are schematic illustrations of an exemplary method of using stent-graft deployment system 410, described hereinabove with reference to FIGS. 11-12C, to deploy stent-graft 140, described hereinabove with reference to FIGS. 7A-C and 9, three branching stent-grafts 390A, 390B, and 390C, and a second main stent-graft 392, in the vicinity of sub-renal (e.g., juxtarenal) abdominal aortic aneurysm 310 of the abdominal aorta, in accordance with an application of the present invention. Stent-graft deployment system 410 may also be used to treat a blood vessel suffering from a dissection. In this particular exemplary deployment, deployment system 410 is not configured such that the at least one second restraining wire 462 engages third longitudinal portion 670 of stent-graft 140. Stent-graft deployment system 410 may alternatively be used to deploy other stent-grafts, such as stent-graft 40.

As shown in FIG. 13A, during a first stage of the implantation procedure, guidewire 100 is transvascularly (typically percutaneously) advanced into the aorta e.g., via one of iliac arteries 314A or 314B.

As shown in FIG. 13B, delivery shaft 430 is transvascularly (typically percutaneously) advanced into the aorta e.g., via one of iliac arteries 314A or 314B, while stent-graft 140 is held in its first, highly radially-compressed state within outer sheath 34. In this exemplary deployment, delivery shaft 430 and distal tip 32 are advanced over guidewire 100 until the distal tip is positioned at or slightly above renal arteries 312A and 312B. Typically, during advancement of delivery shaft 430 (including inner shaft 436), little or no tensile force (e.g., less than 10 N of tensile force, such as zero N of tensile force) is applied to the proximal portion of the restraining wires, such that the restraining wires are loose, such as described hereinbelow with reference to FIGS. 15B and 16B. If the restraining wires were instead held taut during advancement of delivery shaft 430 through blood vessels, this would reduce the flexibility of the delivery system when advancing through tortuous blood vessels.

As shown in FIG. 13C, outer sheath 34 is partially withdrawn proximally, releasing a longitudinal portion of stent-graft 140, including second longitudinal portion 570 of the stent-graft. At this stage of deployment, outer sheath 34 no longer holds second longitudinal portion 570 of stent-graft in the first radially-compressed state, and allows partial radial expansion of second longitudinal portion 570 of stent-graft 140 to a second radially-compressed state in which second longitudinal portion 570 of stent-graft 140 is less radially compressed than in the first radially-compressed state. The at least one second restraining wire 462 still prevents the full radial expansion of second longitudinal portion 570 of stent-graft 140 by physically engaging second longitudinal portion 570 of stent-graft 140.

FIG. 13D shows delivery shaft 430 and stent-graft 140 after outer sheath 34 has been entirely proximally withdrawn from stent-graft 140. At this stage of deployment, outer sheath 34 no longer holds first longitudinal portion 470 or second longitudinal portion 570 of stent-graft 140 in first radially-compressed states, and allows partial radial expansion of both first and second longitudinal portions 470 and 570 to second radially-compressed states in which the longitudinal portions are less radially compressed than in the first radially-compressed states. The at least one first restraining wire 460 still prevents the full radial expansion of first longitudinal portion 470, and the at least one second restraining wire 462 still prevents the full radial expansion of second longitudinal portion 570, and, optionally, a longitudinal portion of the stent-graft between the first and second longitudinal portions, as explained above with reference to FIG. 6D regarding first and second longitudinal portions 70 and 170 of stent-graft 40.

As shown in FIG. 13E, three guidewires 680A, 680B, and 680C are introduced through the proximal end of stent-graft 140, out of lateral fenestrations 180, 182, and 184, respectively, and into right renal artery 312A, left renal artery 312B, and superior mesenteric artery (SMA) 316, respectively.

As shown in FIG. 13F, three cannulae 682A, 682B, and 682C are advanced over guidewires 680A, 680B, and 680C, respectively through the proximal end of stent-graft 140, out of lateral fenestrations 180, 182, and 184, respectively, and into right renal artery 312A, left renal artery 312B, and superior mesenteric artery (SMA) 316, respectively. These cannulae help accurately position the lateral fenestrations opposite the ostia of the renal and superior mesenteric arteries. The use of these cannulae is optional.

As mentioned above, first longitudinal portion of 470 of stent-graft 140 is still constrained when the guidewires and cannulae are advanced through the lateral fenestrations and into the branching arteries. This allows the operator to adjust the longitudinal and/or rotational disposition of the stent-graft as necessary to best align the fenestrations with the ostia of the branching arteries, because the non-expanded first longitudinal portion of 470 is not constrained by the wall of the aorta.

As shown in FIG. 13G, after the fenestrations have been properly positioned with respect to the ostia of the branching arteries, the at least one first restraining wire 460 is proximally withdrawn from first enclosed longitudinal segment 452 (and first restraining longitudinal portion 456) (shown in FIG. 11). The at least one first restraining wire 460 thus does not prevent the full radial expansion of first longitudinal portion 470 of stent-graft 140, which self-expands (typically, until expansion is at least partially inhibited by the wall of the aorta).

At this stage of the deployment, the at least one second restraining wire 262 is still removably disposed in third and fourth enclosed longitudinal segments 482 and 484, and thus continues to prevent the full radial expansion of second longitudinal portion 570. This permits adjustment of the longitudinal and/or rotational disposition of the distal portion of the stent-graft if necessary.

FIG. 13H shows delivery shaft 430 after the at least one second restraining wire 462 has been proximally withdrawn from third enclosed longitudinal segment 482 (and from alongside second restraining longitudinal portion 486), thus allowing the self-expansion of second longitudinal portion 570 until expansion is at least partially inhibited by the wall of the aorta. Typically, until the withdrawal of the restraining wires, little or no tensile force is applied to the proximal portions of the restraining wires, such that the restraining wires are loose, such as described hereinbelow with reference to FIGS. 15B and 16B.

Figure 13I:
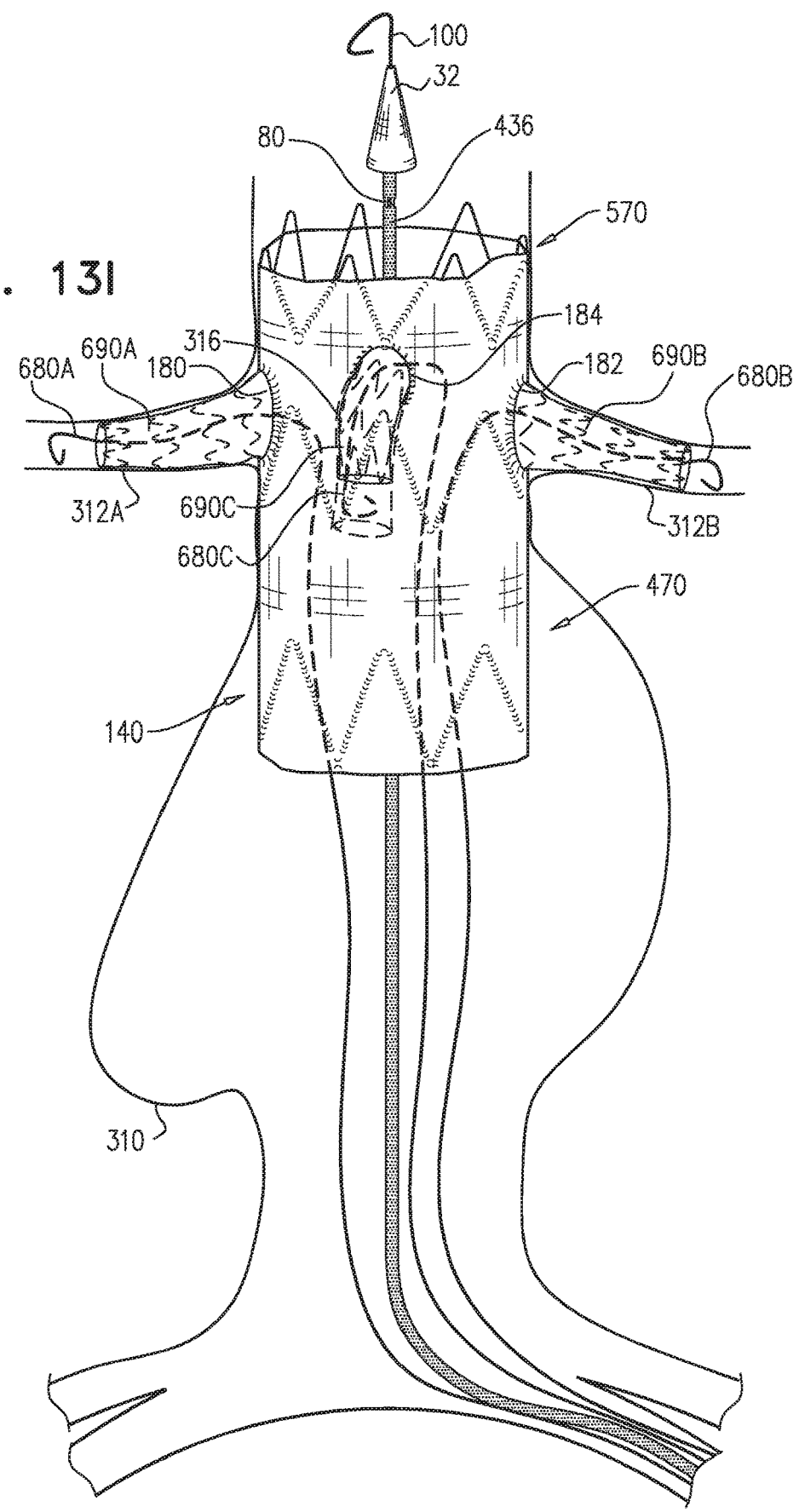

Cannulae 682A, 682B, and 682C are withdrawn from the body over their respective guidewires. As shown in FIG. 13I, first, second, and third branching stent-grafts 690A, 690B, and 690C are introduced over guidewires 680A, 680B, and 680C, and are radially expanded in their respective branching arteries, so as to form respective blood-tight seals with fenestrations 180, 182, and 184. For some applications, respective balloons are used to expand the branching stent-grafts by plastically deformation of the stent-grafts. Alternatively, the branching stent-grafts are self-expanding, which case they are introduced in respective outer sheaths, which are subsequently withdrawn to release the stent-grafts.

Figure 13J:
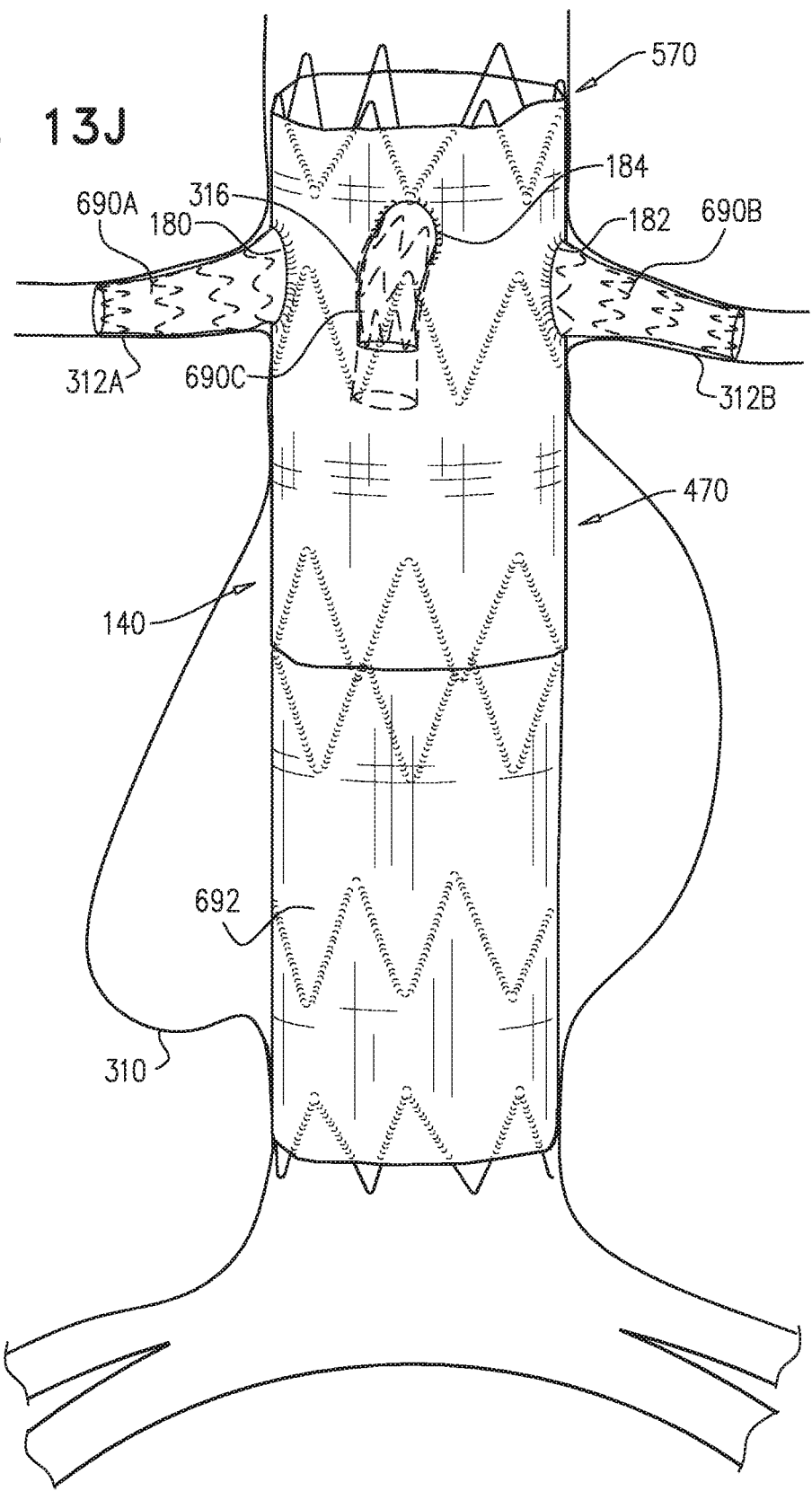

As shown in FIG. 13J, second main stent-graft 392 is deployed and blood-tightly sealingly coupled to a proximal end of stent-graft 140. As a result, main stent-graft 392, stent-grafts 140, and branching stent-grafts 690A, 690B, and 690C together define a fluid flow path past aortic aneurysm 310 to the ascending aorta and the renal arteries and SMA.

Although second conduits 480 are shown in FIGS. 13C-I as defining first and second openings 80 and 82, such as described hereinabove with reference to FIG. 5, second conduits 480 may also be open along second restraining longitudinal portion 486 of inner shaft 436, such as described hereinabove with reference to FIGS. 11-12C.

Reference is now made to FIGS. 14A-E, which are schematic illustrations of a portion of control handle 20, in accordance with an application of the present invention. One configuration of the entire control handle 20 is shown in FIG. 1. The control handle is coupled to a proximal portion of inner shaft 36. Control handle 20 comprises a withdrawal actuator 700, which is coupled to proximal portion 72 of the at least one restraining wire 60. Withdrawal actuator 700 is configured, upon actuation thereof, to withdraw the at least one restraining wire 60 in a proximal direction, thereby withdrawing the at least one restraining wire 60 from at least first enclosed longitudinal segment 52, and releasing and allowing radial expansion of the one or more longitudinal portions of stent-graft 40 that are restrained by the at least one restraining wire 60. For applications in which the at least one restraining wire 60 comprises a plurality of restraining wires 60, respective proximal portions 72 of the wires are coupled to withdrawal actuator 700.

Figure 14A:
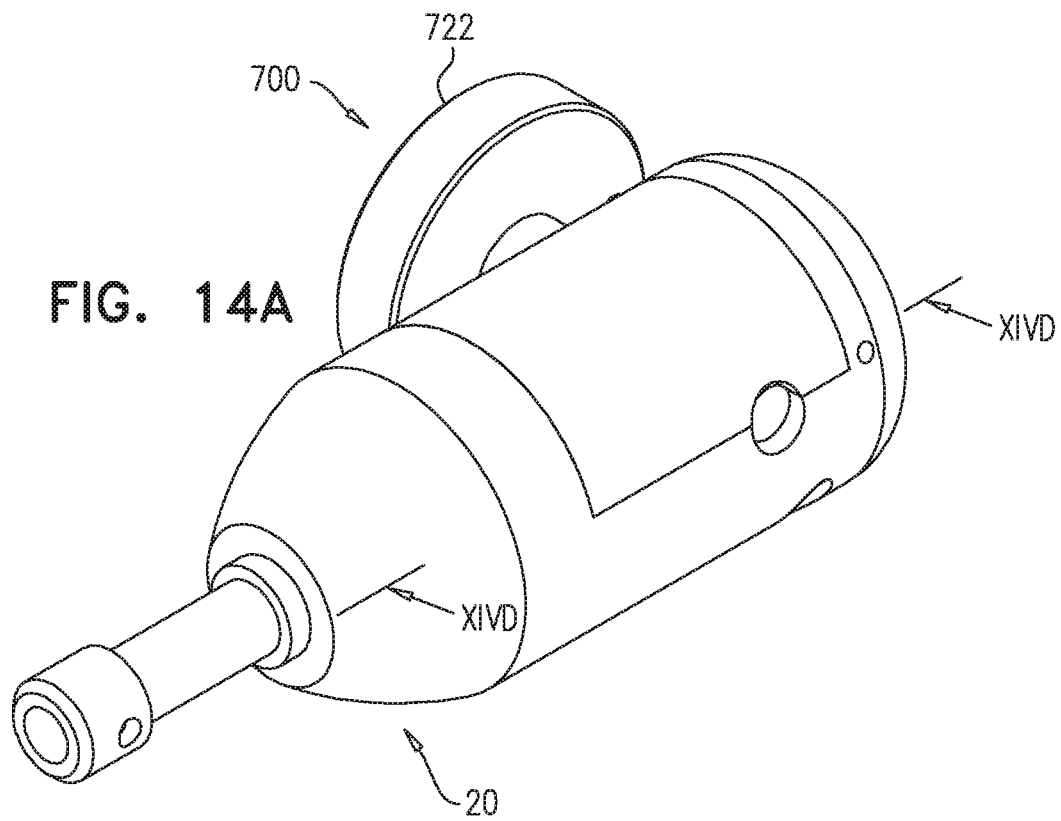
FIGS. 14A-E are schematic illustrations of a portion of a control handle, in accordance with an application of the present invention.
Figure 14B:
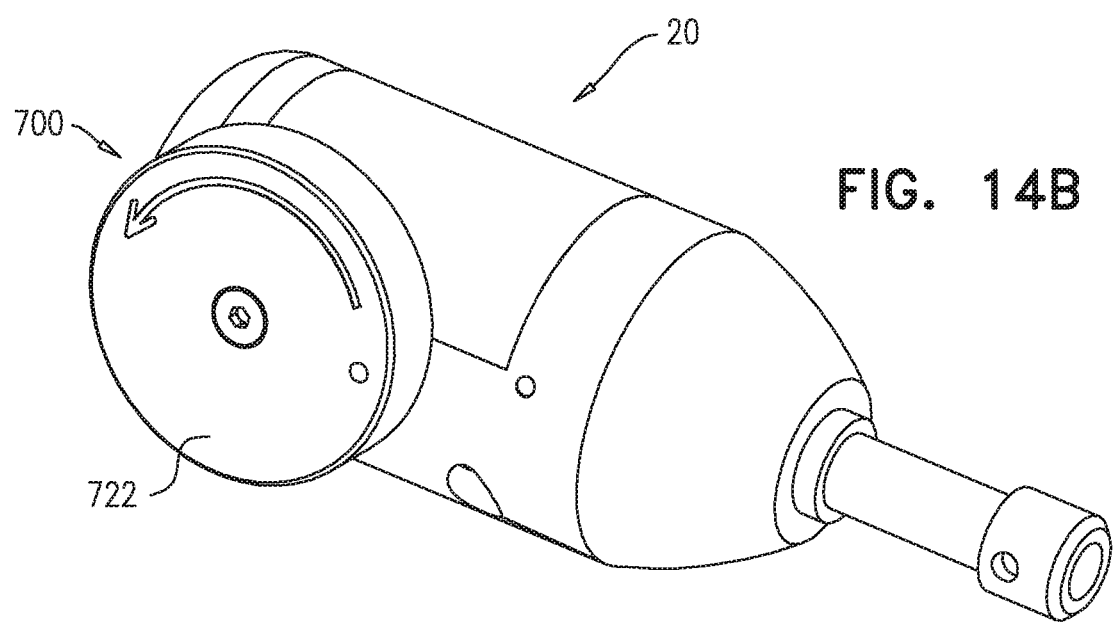
Figure 14C:
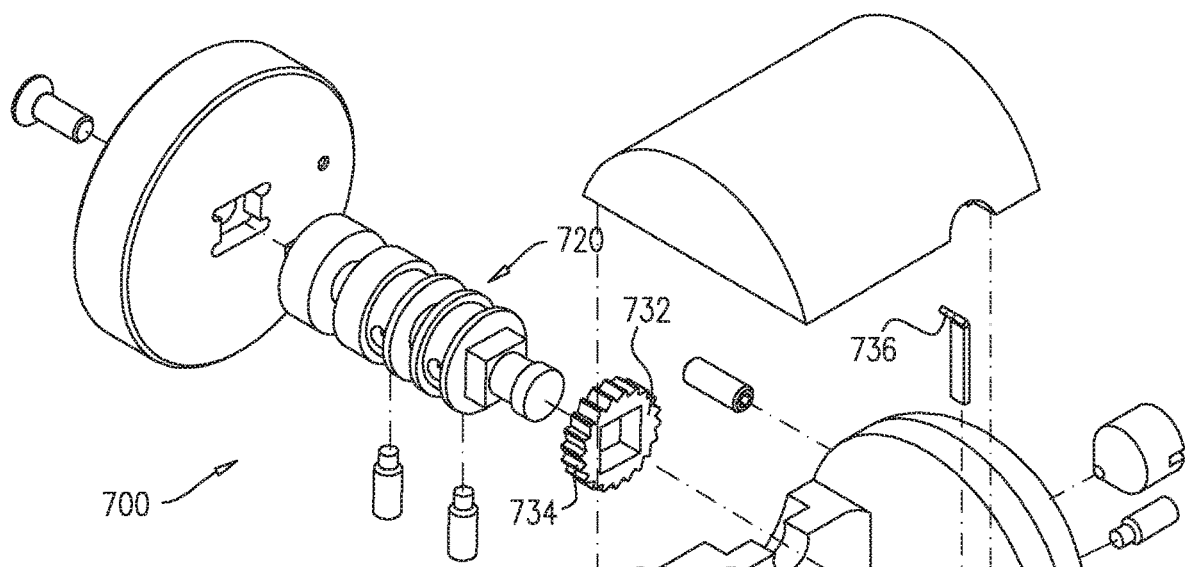
Figure 14D:
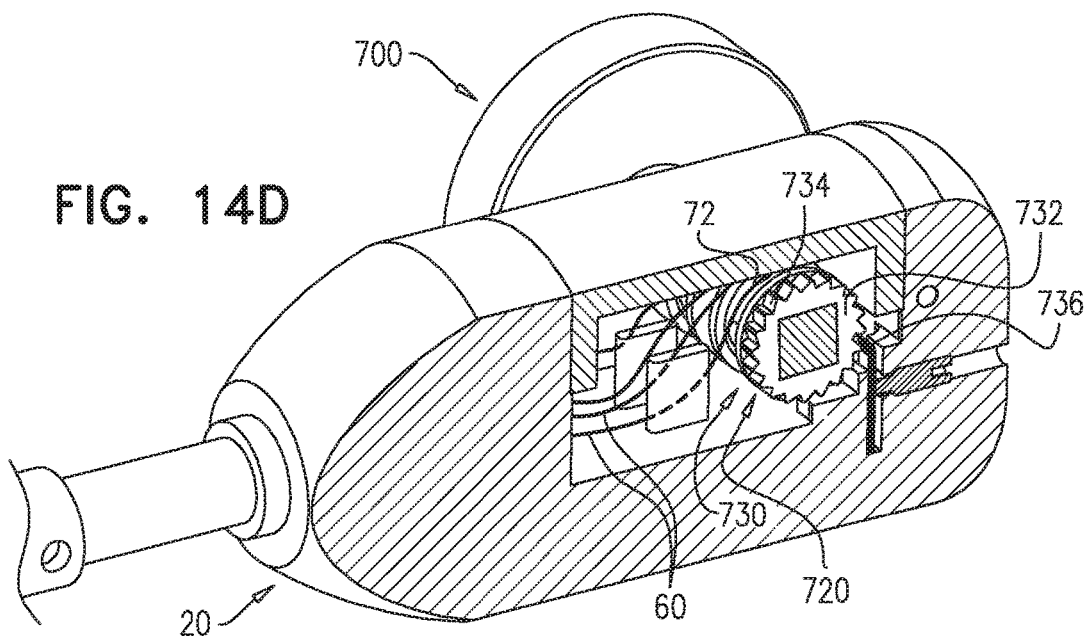
Figure 14E:
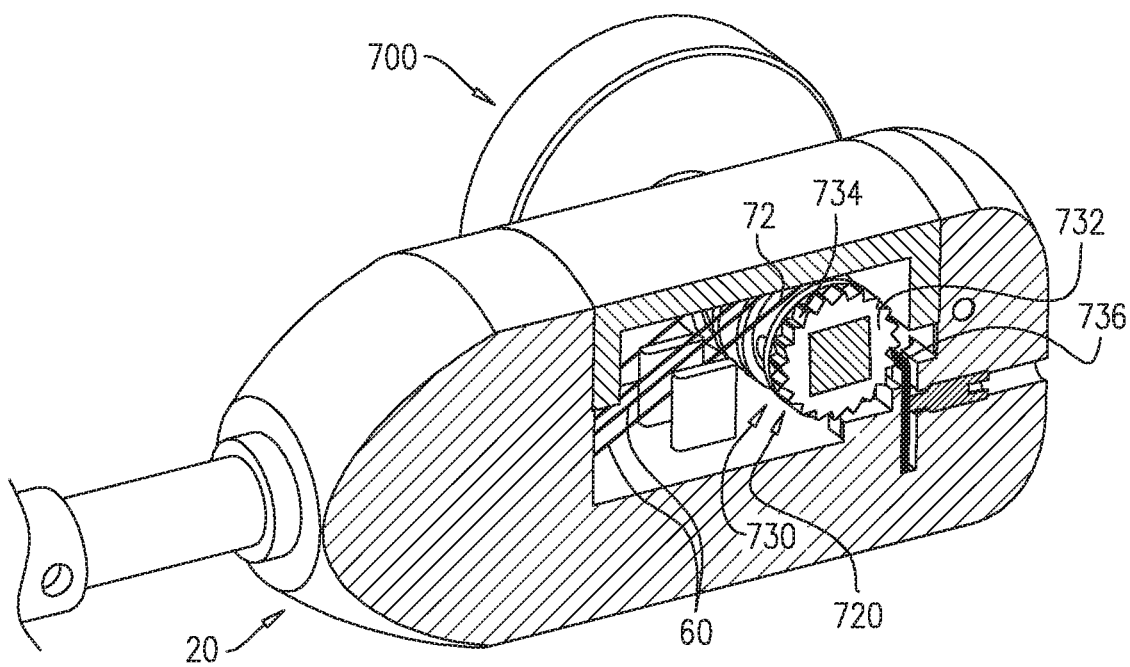

For some applications, as can be seen in FIGS. 14C-E, withdrawal actuator 700 comprises a spool 720 to which proximal portion(s) 72 of restraining wire(s) 60 are coupled.

Spool 720 is arranged such that rotation thereof withdraws restraining wire(s) 60 in the proximal direction. For these applications, withdrawal actuator 700 typically further comprises a knob 722, which is fixed to spool 720, such that rotation of the knob rotates the spool. Withdrawal actuator 700 thus provides a convenient way for the operator to withdraw the restraining wire(s) without needing to draw them a distance from the subject's body. For some applications in which the at least one restraining wire 60 comprises a plurality of restraining wires 60, withdrawal actuator 700 withdraws all of the wires simultaneously.

For some applications, withdrawal actuator 700 comprises a mechanism other than a spool, such as a slider.

For some applications, spool 720 is configured to be rotatable only in one direction, in order to allow only proximal withdrawal of restraining wire(s) 60, and to prevent accidental distal promotion of the restraining wire(s). Because the restraining wire(s) may have a small diameter, accidental distal advancement of the wire(s) might puncture covering element 44 of the stent-graft and/or the vascular wall. For some applications, spool 720 comprises a ratchet assembly 730, which, for some applications, comprises a saw-toothed gear 732 and a pawl 736. Gear 732 is mounted on the same axis as spool 720. Gear 732 and pawl 736 are arranged such that the pawl interlocks with teeth 734 of saw-toothed gear 732, allowing rotation of the gear, and thus spool 720, in only one direction.

For some applications, the spools described hereinbelow with reference to FIGS. 15A-B and 16A-B implement these unidirectional rotation techniques.

As described hereinabove with reference to FIGS. 2, 3, 4A-B, 10B, and 10F, during advancement of delivery shaft 30 through blood vessels, little or no tensile force (e.g., less than 10 N of tensile force, such as zero N of tensile force) is applied to proximal portion(s) 72 of restraining wire(s) 60, such that the restraining wire(s) are loose, as shown in FIG. 14D. As shown in FIG. 14E, after the stent-graft is properly positioned at a desired location in a blood vessel, tensile force is applied to restraining wire(s) 60 by withdrawal actuator 700, so as to withdraw the restraining wire(s) in a proximal direction.

Figure 15A:
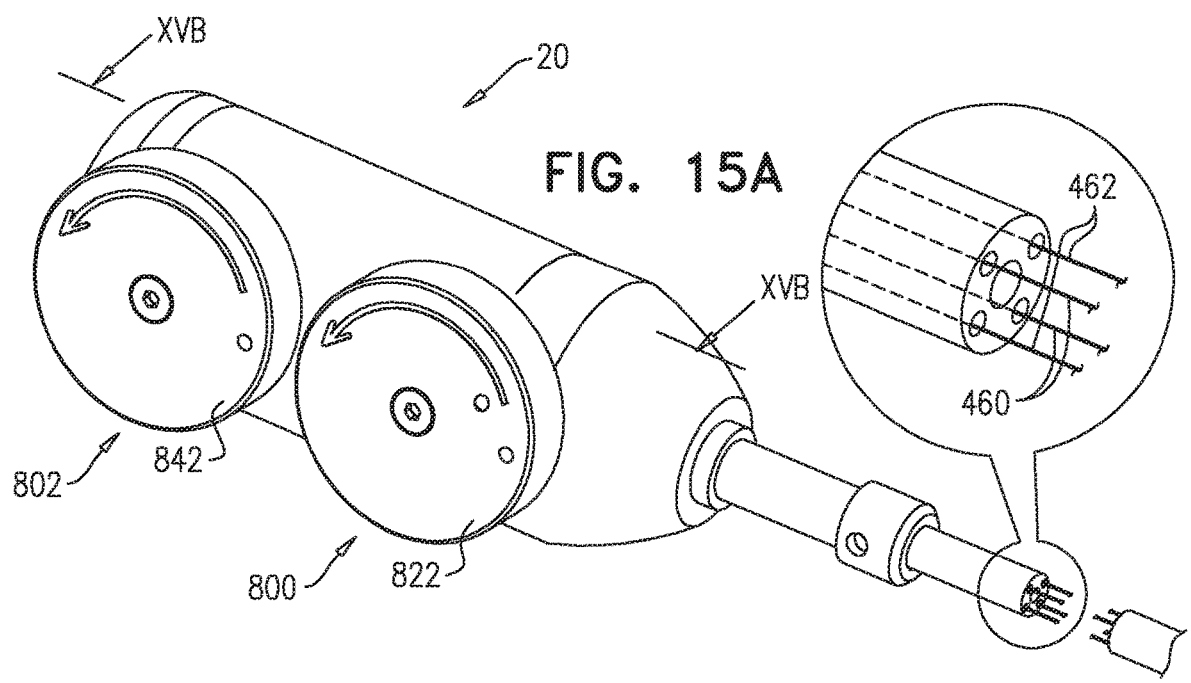
FIGS. 15A-B are schematic illustrations of another configuration of a portion of a control handle, in accordance with an application of the present invention.
Figure 15B:
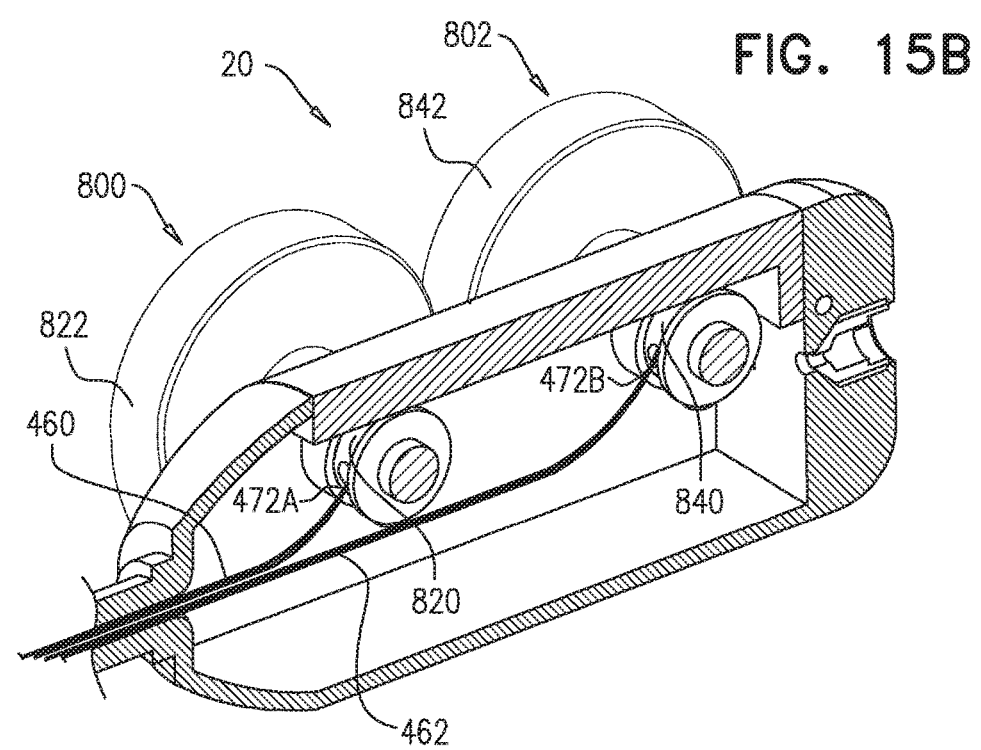

Reference is made to FIGS. 15A-B, which are schematic illustrations of another configuration of a portion of control handle 20, in accordance with an application of the present invention. In this configuration, control handle 20 comprises:
  a first withdrawal actuator 800 to which proximal portion 472A of the at least one first restraining wire 460 is coupled. First withdrawal actuator 800 is configured, upon actuation thereof, to withdraw the at least one first restraining wire 460 in a proximal direction, thereby withdrawing the at least one first restraining wire 460 from at least first enclosed longitudinal segment 452, and releasing and allowing radial expansion of first longitudinal portion 470 of stent-graft 40. For applications in which the at least one first restraining wire 460 comprises a plurality of first restraining wires 460, respective proximal portions 472A of the wires are coupled to first withdrawal actuator 800; and
  a second withdrawal actuator 802 to which proximal portion 472B of the at least one second restraining wire 462 is coupled. Second withdrawal actuator 802 is configured, upon actuation thereof, to withdraw the at least one second restraining wire 462 in the proximal direction, thereby withdrawing the at least one second restraining wire 462 from at least third enclosed longitudinal segment 482, and releasing and allowing radial expansion of second longitudinal portion 570 of stent-graft 40. For applications in which the at least one second restraining wire 462 comprises a plurality of second restraining wires 462, respective proximal portions 472B of the wires are coupled to second withdrawal actuator 802. For applications in which the at least one second restraining wire 462 also restrains third longitudinal portion 670 of stent-graft 40, second withdrawal actuator 802 is configured to also withdraw the at least one second restraining wire 462 from fourth enclosed longitudinal segment 484, thereby releasing and allowing radial expansion of third longitudinal portion 670 of stent-graft 40.

For some applications, first and second withdrawal actuators 800 and 802 comprise first and second spools 820 and 840, respectively, to which proximal portion(s) 472A of first restraining wire(s) 460 and proximal portions 472B or second restraining wires(s) 462, respectively, are coupled. Spools 820 and 840 are arranged such that rotation thereof withdraws first and second restraining wire(s) 460 and 462, respectively, and in the proximal direction. For these applications, first and second withdrawal actuators 800 and 702 typically further comprise first and second knobs 822 and 842, respectively, which are fixed to first and second spools 820 and 840, respectively, such that rotation of the knobs rotates the spools, respectively. First and second withdrawal actuators 800 and 802 thus provides a convenient way for the operator to withdraw first restraining wire(s) 460 separately (e.g., before) from second restraining wire(s) 462, without needing to draw them a distance from the subject's body. Thus, first withdrawal actuator 800 is used to withdraw one subset of the restraining wires, and second withdrawal actuator 802 is used to withdrawn another subset of the restraining wires.

For some applications, first and second withdrawal actuators 800 and 802 comprise respective mechanisms other than spools, such as sliders.

As described hereinabove with reference to FIGS. 2, 3, 4A-B, 13B, and 13H, during advancement of delivery shaft 30 through blood vessels, little or no tensile force (e.g., less than 10 N of tensile force, such as zero N of tensile force) is applied to proximal portion(s) 472 of restraining wires 460 and 462, such that the restraining wires are loose, as shown in FIG. 15B. After the stent-graft is properly positioned at a desired location in a blood vessel, tensile force is applied to restraining wires 460 and 462 by first and second withdrawal actuators 800 and 802, respectively, so as to withdraw the restraining wires in a proximal direction.

Figure 16A:
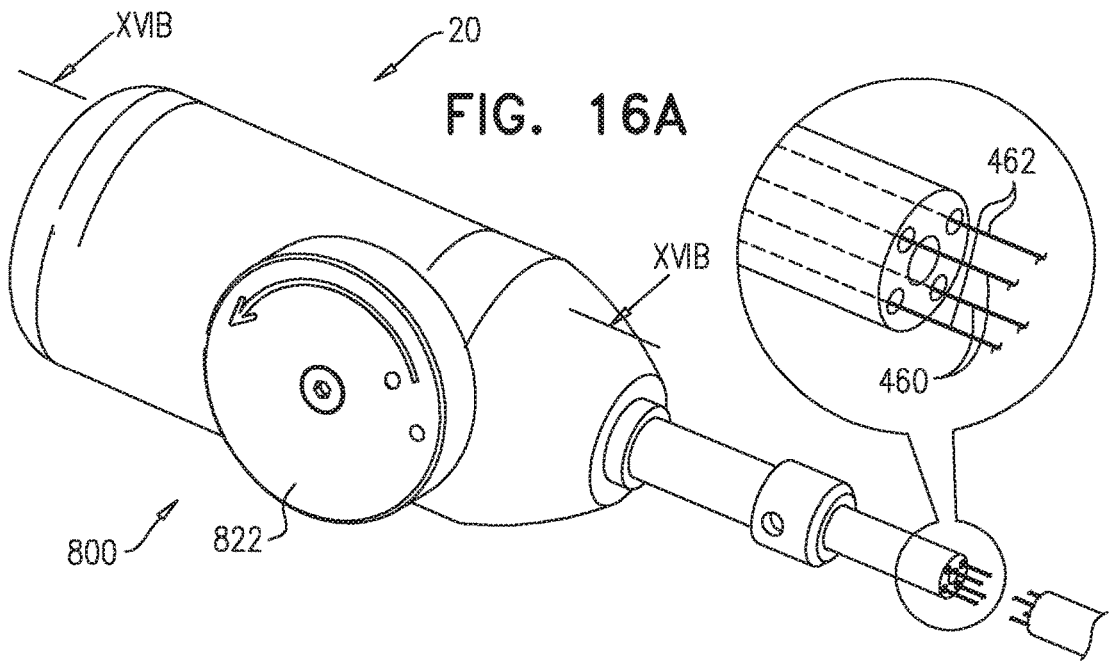
FIGS. 16A-B are schematic illustrations of yet another configuration of a portion of a control handle, in accordance with an application of the present invention.
Figure 16B:
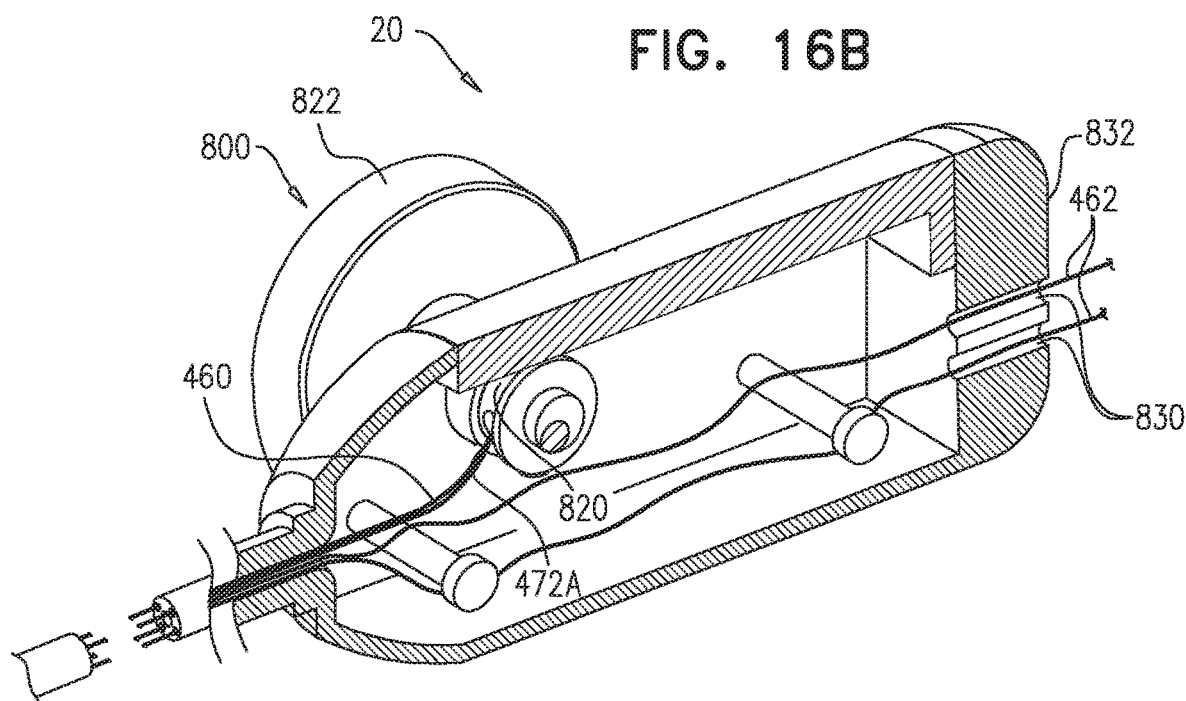

Reference is made to FIGS. 16A-B, which are schematic illustrations of yet another configuration of a portion of control handle 20, in accordance with an application of the present invention. This is configuration is like the configuration described hereinabove with reference to FIGS. 15A-C, except that control handle 20 comprises only first withdrawal actuator 800, which may comprise, for example, spool 820 and, optionally, knob 822. The at least one second restraining wire 462 is withdrawn longitudinally, typically by the operator pulling the at least one second restraining wire 462. For some applications, control handle 20 is shaped so as to define one or more lumens 830 open to an external surface 832 of control handle 20, through which lumen(s) 830 the at least one second restraining wire passes. Thus, withdrawal actuator 800 is used to withdraw one subset of the restraining wires, and another subset of the restraining wires, which pass through the lumen(s), is withdrawn by the operator pulling on the another subset from outside the control handle.

Optionally, the control handle comprises another actuating mechanism for withdrawing the at least one second restraining wire 462, such as a slider (configuration not shown).

The use of only a single withdrawal actuator 800 may potentially prevent (a) confusion that might arise between the two actuators 800 and 802 in the configuration described with reference to FIGS. 15A-B, and/or (b) accidental rotation of one knob while the second knob is being rotated in the configuration described with reference to FIGS. 15A-B. In addition, the configuration shown in FIGS. 16A-B may be less expensive to manufacture than the configuration shown in FIGS. 15A-B, and may be potentially easier to use from an ergonomic point of view.

As described hereinabove with reference to FIGS. 2, 3, 4A-B, 13B, and 13H, during advancement of delivery shaft 30 through blood vessels, little or no tensile force (e.g., less than 10 N of tensile force, such as zero N of tensile force) is applied to proximal portion(s) 472 of restraining wires 460 and 462, such that the restraining wires are loose, as shown in FIG. 15B. After the stent-graft is properly positioned at a desired location in a blood vessel, tensile force is applied to restraining wires 460 and 462, by first withdrawal actuator 800 and the operator, respectively, so as to withdraw the restraining wires in a proximal direction.

Although the techniques described herein have been generally described for implanting a stent-graft in a blood vessel, the techniques maybe used to implant other implantable medical devices that are introduced into the body in a relatively compact state and used within the body in a relatively expanded state. Non-limiting examples of such implantable medical devices include stents, coil stents and filters, catheters, cannulae, intrauterine contraceptive devices (IUDs), bone plates, marrow nails, dental arch wires, filters, bone staples, heart valves, and clips.

The scope of the present invention includes embodiments described in the following applications, which are assigned to the assignee of the present application and are incorporated herein by reference. In an embodiment, techniques and apparatus described in one or more of the following patent applications are combined with techniques and apparatus described herein. In particular, the techniques described herein may be used to deliver any of the radially-compressible stent-grafts and stents described in the following patent applications.

U.S. Pat. No. 8,317,856 to Shalev et al.
U.S. Pat. No. 8,574,287 to Benary et al.
U.S. Provisional Application 60/892,885, filed Mar. 5, 2007
U.S. Provisional Application 60/991,726, filed Dec. 2, 2007
U.S. Provisional Application 61/219,758, filed Jun. 23, 2009
U.S. Provisional Application 61/221,074, filed Jun. 28, 2009
U.S. application Ser. No. 13/031,871, filed Feb. 22, 2011, which published as US Patent Application Publication 2011/0208289
U.S. Provisional Application 61/496,613, filed Jun. 14, 2011
U.S. Provisional Application 61/499,195, filed Jun. 21, 2011
U.S. Provisional Application 61/505,132, filed Jul. 7, 2011
U.S. Provisional Application 61/529,931, filed Sep. 1, 2011
U.S. Provisional Application 61/553,209, filed Oct. 30, 2011
U.S. application Ser. No. 13/380,278, filed Dec. 22, 2011, which published as US Patent Application Publication 2012/0150274
U.S. application Ser. No. 13/384,075, filed Jan. 13, 2012, which published as US Patent Application Publication 2012/0179236
U.S. application Ser. No. 13/505,996, filed May 3, 2012, which published as US Patent Application Publication 2012/0310324
U.S. application Ser. No. 13/513,397, filed Jun. 1, 2012, which published as US Patent Application Publication 2012/0330399
U.S. application Ser. No. 13/514,240, filed Jun. 6, 2012, which published as US Patent Application Publication 2013/0013051
U.S. Provisional Application 61/678,182, filed Aug. 1, 2012
U.S. application Ser. No. 13/577,161, filed Aug. 3, 2012, which published as US Patent Application Publication 2013/0035751
U.S. application Ser. No. 13/512,778, filed Sep. 24, 2012, which published as US Patent Application Publication 2013/0013050
U.S. application Ser. No. 13/807,880, filed Dec. 31, 2012, which published as US Patent Application Publication 2013/0131783
PCT Application PCT/IL2012/000095, filed Mar. 1, 2012, which published as PCT Publication WO 2012/117395
PCT Application PCT/IL2012/000148, filed Apr. 4, 2012, which published as PCT Publication WO 2013/030818
PCT Application PCT/IL2012/000190, filed May 15, 2012, which published as PCT Publication WO 2013/171730
PCT Application PCT/IL2012/000269, filed Jul. 2, 2012, which published as PCT Publication WO 2013/005207
PCT Application PCT/IL2012/050424, filed Oct. 29, 2012, which published as PCT Publication WO 2013/065040
PCT Application PCT/IL2012/050506, filed Dec. 4, 2012, which published as PCT Publication WO 2013/084235
U.S. Provisional Application 61/749,965, filed Jan. 8, 2013, entitled, "Minimization of stent-graft migration during implantation"
U.S. application Ser. No. 13/807,906, filed Feb. 8, 2013, which published as US Patent Application Publication 2013/0204343
U.S. Provisional Application 61/775,964, filed Mar. 11, 2013, entitled, "Multi-component stent-graft system for aortic dissections"
U.S. Provisional Application 61/826,544, filed May 23, 2013
U.S. application Ser. No. 13/979,551, filed Jul. 12, 2013, which published as US Patent Application Publication 2013/0289587
PCT Application PCT/IL2013/050656, filed Jul. 31, 2013, entitled, which published as PCT Publication WO 2014/020609

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating a blood vessel suffering from an aneurysm or a dissection, the method comprising:

advancing an inner shaft of a deployment system through a body lumen of a subject to the blood vessel, while the inner shaft is removably disposed in a self-expanding stent-graft that is shaped so as to define one or more lateral fenestrations, wherein the inner shaft is shaped so as to define one or more conduits therealong, which conduits are not coaxial with the inner shaft, wherein advancing comprises advancing the inner shaft while one or more restraining wires of the deployment system (a) are at least partially removably disposed in the conduits, and (b) prevent full radial expansion of one or more longitudinal portions of the self-expanding stent-graft by physically engaging the one or more longitudinal portions of the self-expanding stent-graft;

introducing one or more guidewires into a proximal end of the self-expanding stent-graft, out of the one or more lateral fenestrations, respectively, and into one or more branching blood vessels, respectively, wherein the one or more branching blood vessels branch from the blood vessel;

aligning the one or more fenestrations with respective ostia of the one or more branching arteries;

after aligning the one or more fenestrations, at least partially withdrawing the one or more restraining wires, such that the one or more restraining wires do not prevent the full radial expansion of the one or more longitudinal portions of the self-expanding stent-graft;

introducing one or more branching stent-grafts over the one or more guidewires, respectively, into the proximal end of the self-expanding stent-graft, out of the one or more lateral fenestrations, respectively, and into the one or more branching blood vessels, respectively; and radially expanding the one or more branching stent-grafts so that the one or more branching stent-grafts form respective blood-tight seals with the one or more lateral fenestrations, respectively, wherein the one or more restraining wires include first and second restraining wires, and the one or more longitudinal portions of the self-expanding stent-graft include first and second longitudinal portions of the self-expanding stent-graft, wherein advancing the inner shaft comprises advancing the inner shaft while:

the inner shaft is removably disposed in the self-expanding stent-graft, the first restraining wire (a) physically engages the first longitudinal portion of the self-expanding stent-graft, thereby preventing full radial expansion of the first longitudinal portion, and (b) does not engage the second longitudinal portion of the self-expanding stent-graft, which second longitudinal portion does not longitudinally overlap the first longitudinal portion, and the second restraining wire (a) physically engages the second longitudinal portion of the self-expanding stent-graft, thereby preventing full radial expansion of the second longitudinal portion, and (b) does not engage the first longitudinal portion of the self-expanding stent-graft, wherein at least partially withdrawing the one or more restraining wires comprises at least partially withdrawing the first restraining wire, wherein the method further comprises:

after at least partially withdrawing the first restraining wire, adjusting a disposition of the second longitudinal portion of the self-expanding stent-graft; and thereafter, at least partially withdrawing the second restraining wire, and wherein the deployment system further includes a control handle, which (a) includes a withdrawal actuator, which includes a spool to which a proximal portion of a spool-coupled restraining wire is coupled, and (b) is shaped so as to define one or more lumens open to an external surface of the control handle, through which lumen an externally-accessible restraining wire passes, wherein the spool-coupled restraining wire is one of the first and the second restraining wires and the externally-accessible restraining wire is the other of the first and the second restraining wires, wherein at least partially withdrawing the first and the second restraining wires comprises rotating the spool to at least partially withdraw the spool-coupled restraining wire in a proximal direction, and pulling on the externally-accessible restraining wire from outside the control handle.

2. The method according to claim 1, wherein each of the one or more conduits is shaped so as to define (a) at least first and second enclosed longitudinal segments, each of which has a length of at least 30 mm, and (b) a restraining longitudinal portion that is longitudinally disposed between the first and the second enclosed longitudinal segments, and wherein advancing comprises advancing the inner shaft while one of the restraining wires is removably disposed in the first and the second enclosed longitudinal segments, and a portion of the one restraining wire disposed alongside the restraining longitudinal portion of the inner shaft prevents the full radial expansion of one of the one or more longitudinal portions of the self-expanding stent-graft by physically engaging the one longitudinal portion of the self-expanding stent-graft.

3. The method according to claim 2, wherein the deployment system further includes:

a first ring, which is longitudinally fixed to and surrounds the inner shaft at a first longitudinal border between the first enclosed longitudinal segment and the restraining longitudinal portion defined by the one or more conduits; and a second ring, which is longitudinally fixed to and surrounds the inner shaft at a second longitudinal border between the second enclosed longitudinal segment and the restraining longitudinal portion defined by the one or more conduits.

4. The method according to claim 1, wherein the second longitudinal portion is disposed more distal than the first longitudinal portion.

5. The method according to claim 1, wherein withdrawing the one or more restraining wires comprises withdrawing the one or more restraining wires in the proximal direction, and wherein advancing the inner shaft comprises applying no tensile force or less than 10 N of tensile force to respective proximal portions of the one or more restraining wires while advancing the inner shaft.

6. The method according to claim 1, wherein the one or more restraining wires terminate at respective free distal ends thereof.

7. The method according to claim 1, wherein each of the one or more restraining wires has at least one property selected from the group consisting of: a moment of inertia of at least 0.0002 mm$^4$, and a Young's modulus of at least 60 GPa.

8. The method according to claim 1, wherein advancing the inner shaft comprises:
- advancing the inner shaft while the inner shaft is removably disposed in the self-expanding stent-graft, and while one or more longitudinal portions of the self-expanding stent-graft are held in respective first radially-compressed states within an outer sheath, and
- proximally withdrawing the outer sheath from the self-expanding stent-graft, such that the outer sheath no longer holds the one or more longitudinal portions in the respective first radially-compressed states, and allows partial radial expansion of the one or more longitudinal portions to respective second radially-compressed states in which the one or more longitudinal portions are less radially compressed than in the first radially-compressed states.

9. The method according to claim 1,
- wherein the one or more lateral fenestrations include three lateral fenestrations,
- wherein the one or more branching blood vessels include and a right renal artery, a left renal artery, and a superior mesenteric artery,
- wherein introducing the one or more guidewires comprises introducing three guidewires into the proximal end of the self-expanding stent-graft, out of the lateral fenestrations, respectively, and into the right renal artery, the left renal artery, and the superior mesenteric artery, respectively, and
- wherein introducing the one or more branching stent-grafts comprises introducing the three branching stent-grafts over the three guidewires, respectively, into the proximal end of the self-expanding stent-graft, out of the three lateral fenestrations, respectively, and into the right renal artery, the left renal artery, and the superior mesenteric artery, respectively.

10. The method according to claim 1, wherein aligning comprises aligning, after introducing the one or more guidewires, the one or more fenestrations with the respective ostia of the one or more branching arteries.

11. The method according to claim 1, further comprising:
- after introducing the one or more guidewires, advancing one or more cannulae over the guidewires, respectively, into the proximal end of the self-expanding stent-graft, out of the one or more lateral fenestrations, respectively, and into the one or more branching blood vessels, respectively,
- using the one or more cannulae to help accurately position the one or more lateral fenestrations, respectively, opposite the respective ostia of the one or more branching blood vessels, and
- after at least partially withdrawing the one or more restraining wires and before introducing the one or more branching stent-grafts, withdrawing the one or more cannulae from the body over the one or more respective guidewires.

* * * * *